United States Patent
Dirisio et al.

(10) Patent No.: US 9,498,259 B2
(45) Date of Patent: Nov. 22, 2016

(54) DYNAMIC SPINAL PLATING SYSTEM

(75) Inventors: Darryl Dirisio, Slingerlands, NY (US);
M. Parvez Shaikh, Kentwood, MI (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 95 days.

(21) Appl. No.: 14/129,116

(22) PCT Filed: Jun. 29, 2012

(86) PCT No.: PCT/US2012/045023
§ 371 (c)(1),
(2), (4) Date: Mar. 28, 2014

(87) PCT Pub. No.: WO2013/003765
PCT Pub. Date: Jan. 3, 2013

(65) Prior Publication Data
US 2014/0200613 A1 Jul. 17, 2014

Related U.S. Application Data

(60) Provisional application No. 61/502,538, filed on Jun. 29, 2011.

(51) Int. Cl.
*A61B 17/70* (2006.01)
*A61B 17/80* (2006.01)

(52) U.S. Cl.
CPC ....... *A61B 17/7059* (2013.01); *A61B 17/8047* (2013.01); *A61B 17/702* (2013.01); *A61B 17/8004* (2013.01); *A61B 17/8061* (2013.01)

(58) Field of Classification Search
CPC ............ A61B 17/7059; A61B 17/8047; A61B 17/702; A61B 17/8004; A61B 17/8061
See application file for complete search history.

(56) References Cited

U.S. PATENT DOCUMENTS 6,106,527 A 8/2000 Wu et al.
6,280,445 B1 8/2001 Morrison et al.
(Continued)

OTHER PUBLICATIONS

International Search Report for PCT/US2012/045023 dated Sep. 25, 2012.
(Continued)

*Primary Examiner* — Ellen C Hammond
(74) *Attorney, Agent, or Firm* — Heslin Rothenberg Farley & Mesiti P.C.; John W. Boger

(57) ABSTRACT

Dynamic spinal plating systems that can be placed on the anterior aspect of the spine to aid in spinal fusion and surgical methods for using the dynamic spinal plating systems are disclosed. The dynamic spinal plating systems including a plate and at least one bone attachment mechanism. The plate including a superior end with at least one screw hole, an inferior end, and two lateral sides forming an opening that is transverse by the bone attachment mechanism. The dynamic spinal plating systems also include at least one screw plate with a center screw hole and two passageways that mate with two transverse members of the bone attachment mechanism. When implanted the vertebral stabilization devices may provide a degree of movement in the superior-inferior direction providing for a minimal change in length as the patient moves and as vertebral body height decreases.

19 Claims, 51 Drawing Sheets

(56) References Cited

U.S. PATENT DOCUMENTS

| | | | |
|---|---|---|---|
| 6,312,431 B1* | 11/2001 | Asfora | A61B 17/7068 606/263 |
| 2002/0111630 A1 | 8/2002 | Ralph et al. | |
| 2005/0004573 A1 | 1/2005 | Abdou | |
| 2005/0010218 A1 | 1/2005 | Dalton | |
| 2005/0010221 A1 | 1/2005 | Dalton | |
| 2005/0085814 A1* | 4/2005 | Sherman | A61B 17/7026 606/257 |
| 2005/0177160 A1* | 8/2005 | Baynham | A61B 17/8009 606/282 |
| 2005/0273105 A1 | 12/2005 | Konieczynski et al. | |
| 2005/0277931 A1* | 12/2005 | Sweeney | A61B 17/1671 606/264 |
| 2005/0288669 A1 | 12/2005 | Abdou | |
| 2006/0167457 A1* | 7/2006 | Suddaby | A61B 17/7059 606/70 |
| 2007/0276371 A1* | 11/2007 | Baynham | A61B 17/7059 606/86 A |
| 2007/0293863 A1* | 12/2007 | Reimels | A61B 17/8004 606/291 |
| 2008/0234681 A1* | 9/2008 | Baynham | A61B 17/8009 606/71 |
| 2008/0306528 A1 | 12/2008 | Winslow et al. | |
| 2009/0024165 A1* | 1/2009 | Ferree | A61B 17/7022 606/246 |
| 2009/0275988 A1* | 11/2009 | Baynham | A61B 17/7059 606/282 |
| 2010/0057128 A1 | 3/2010 | Bullard | |
| 2010/0268279 A1 | 10/2010 | Gabelberger et al. | |
| 2011/0098757 A1 | 4/2011 | Schelling | |
| 2011/0118784 A1* | 5/2011 | Baynham | A61B 17/7059 606/264 |
| 2011/0152941 A1* | 6/2011 | Graf | A61B 17/7007 606/277 |
| 2015/0257803 A1* | 9/2015 | Sampath | A61B 17/8023 606/71 |

OTHER PUBLICATIONS

International Preliminary Report on Patentability for international application No. PCT/US2012/045023, mailed on Jan. 16, 2014.
Oct. 15, 2015: European Search Report for European Application No. 12803862.7 / PCT/US2012/045023.

* cited by examiner

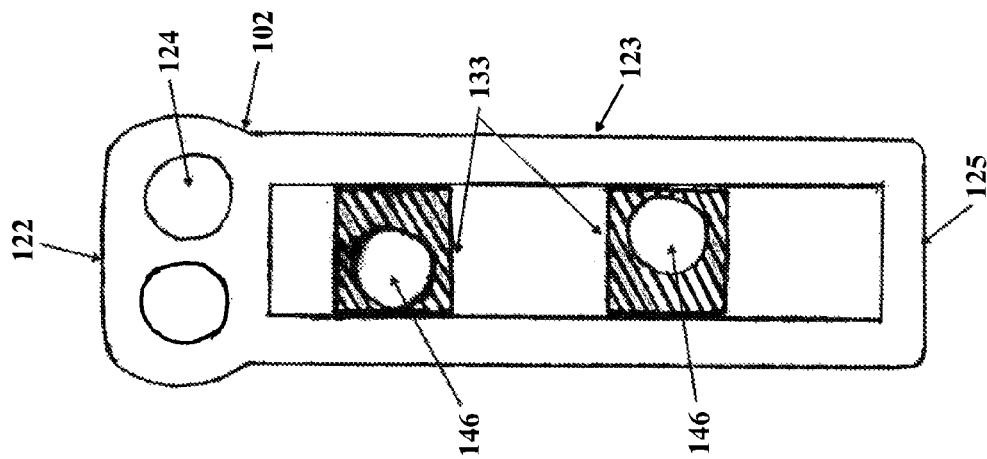
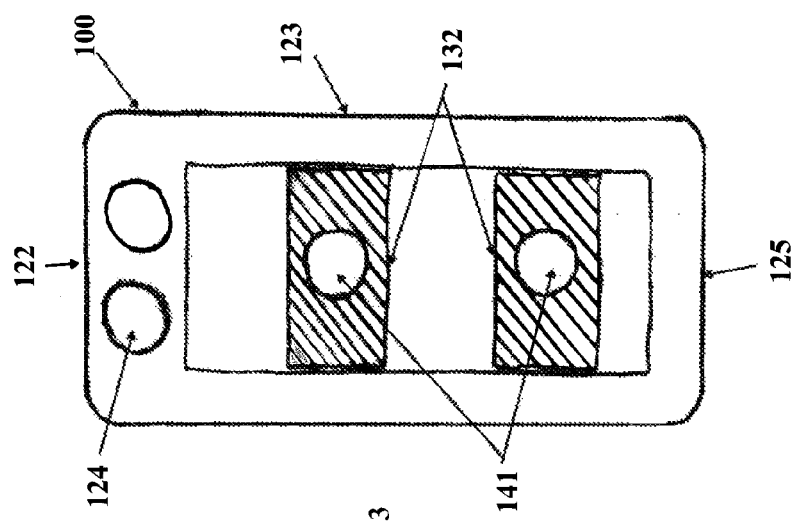
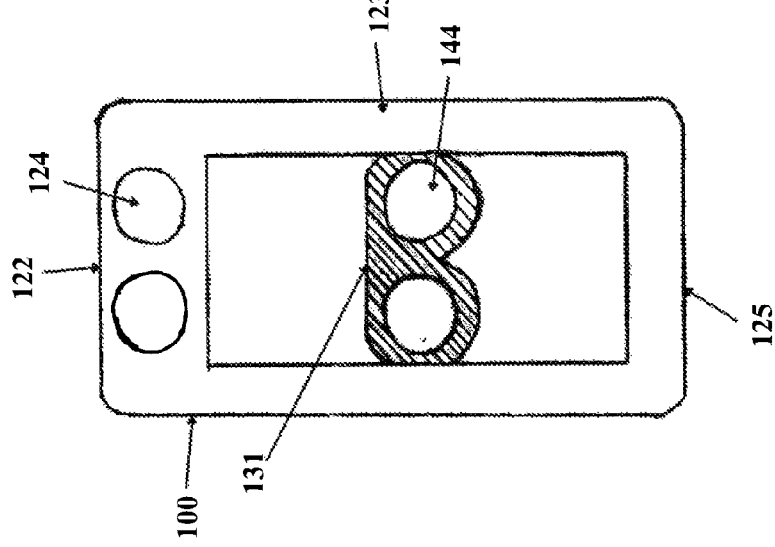
FIG. 1h
FIG. 1g
FIG. 1f

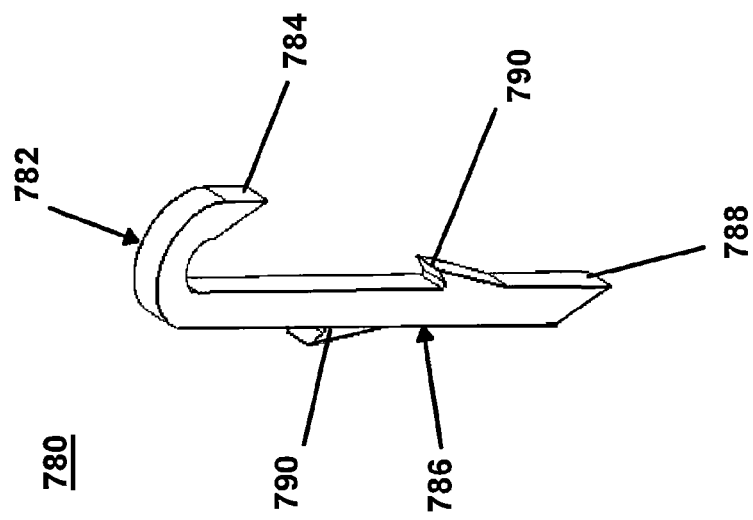
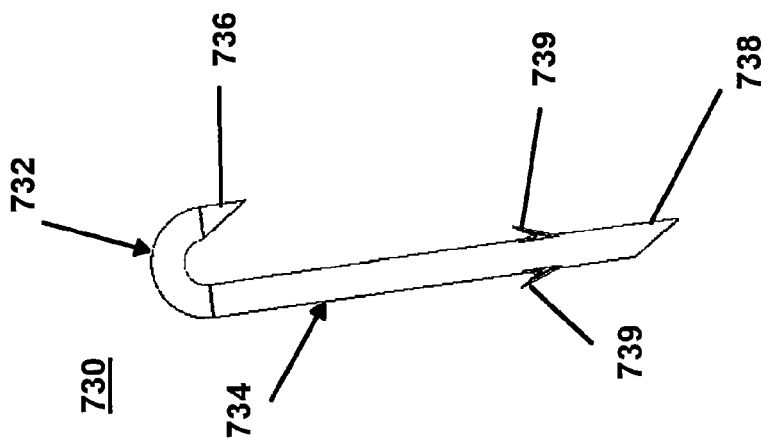

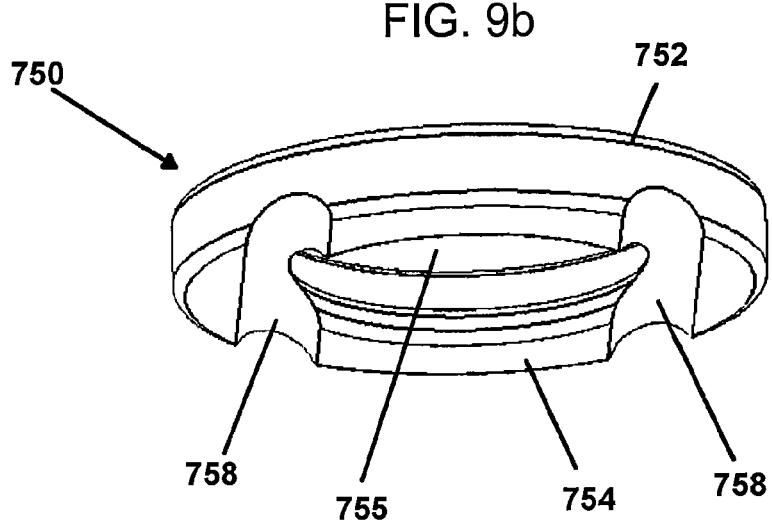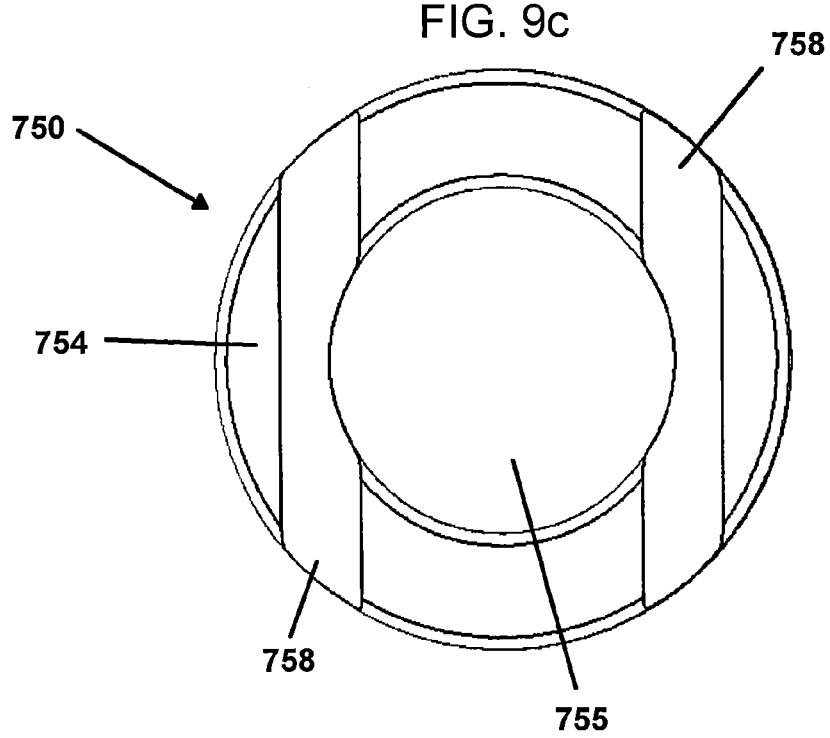

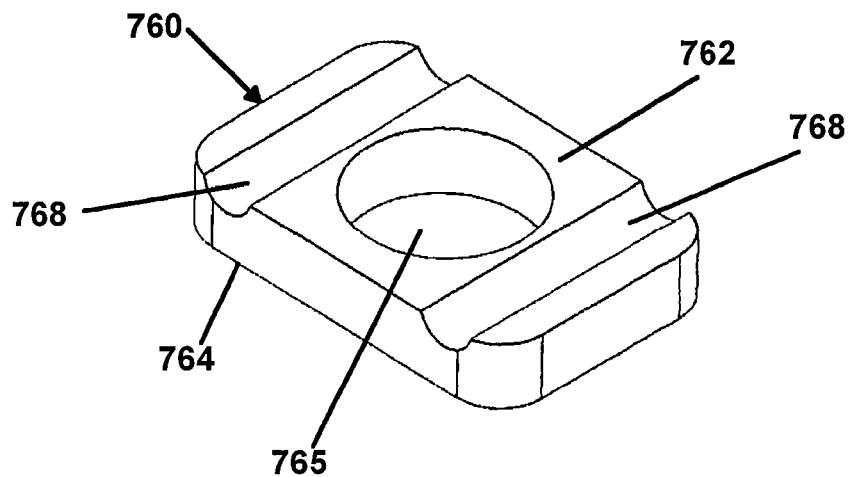
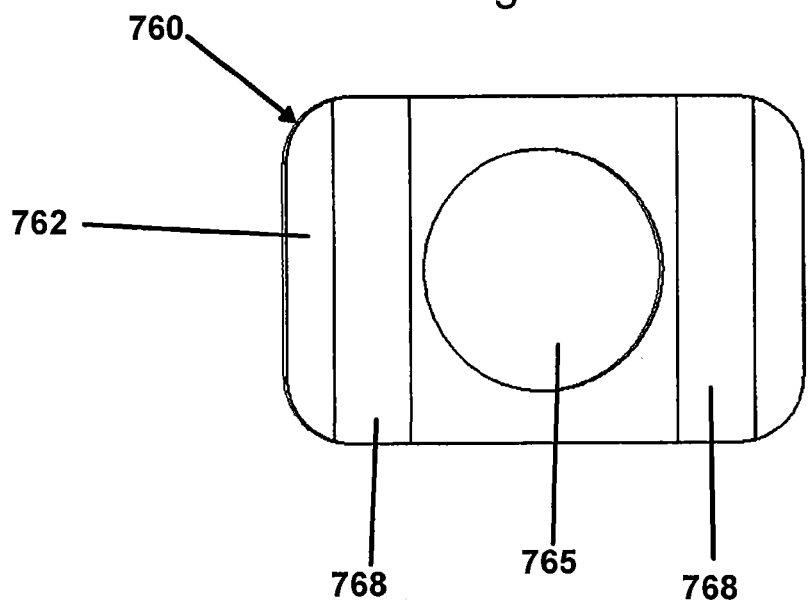

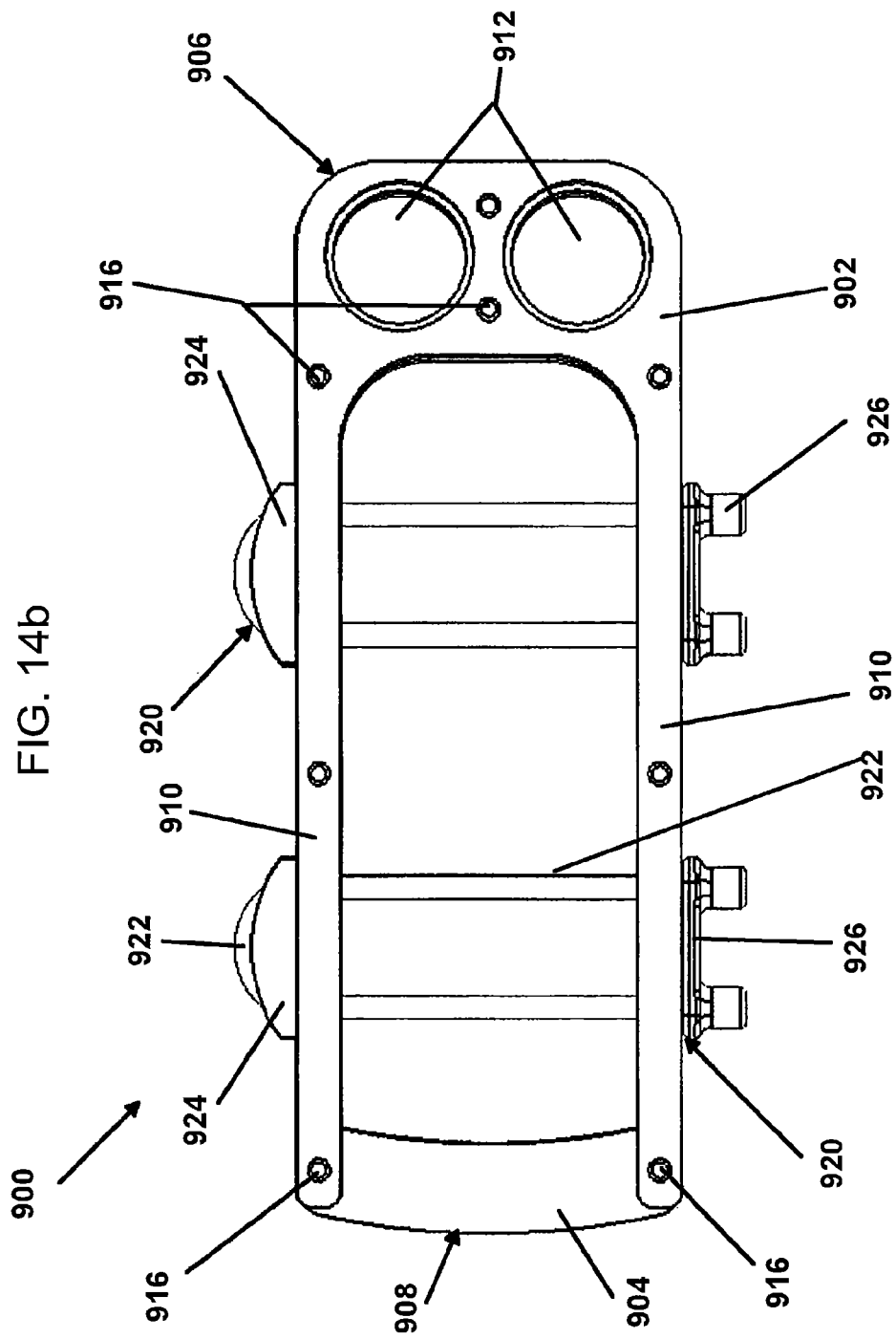

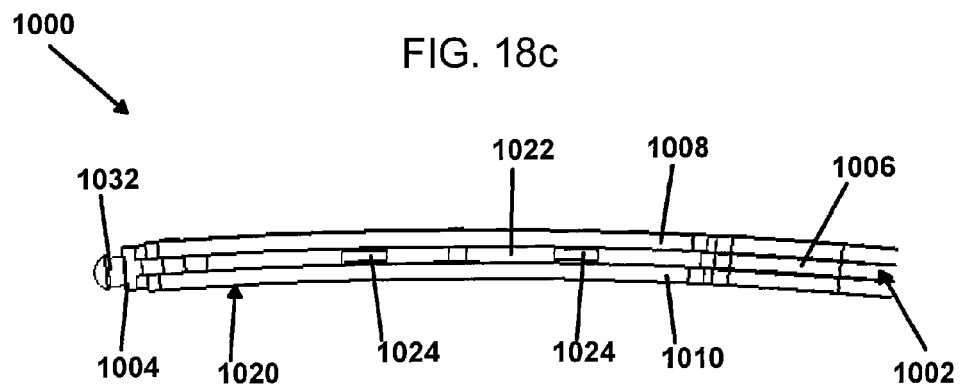
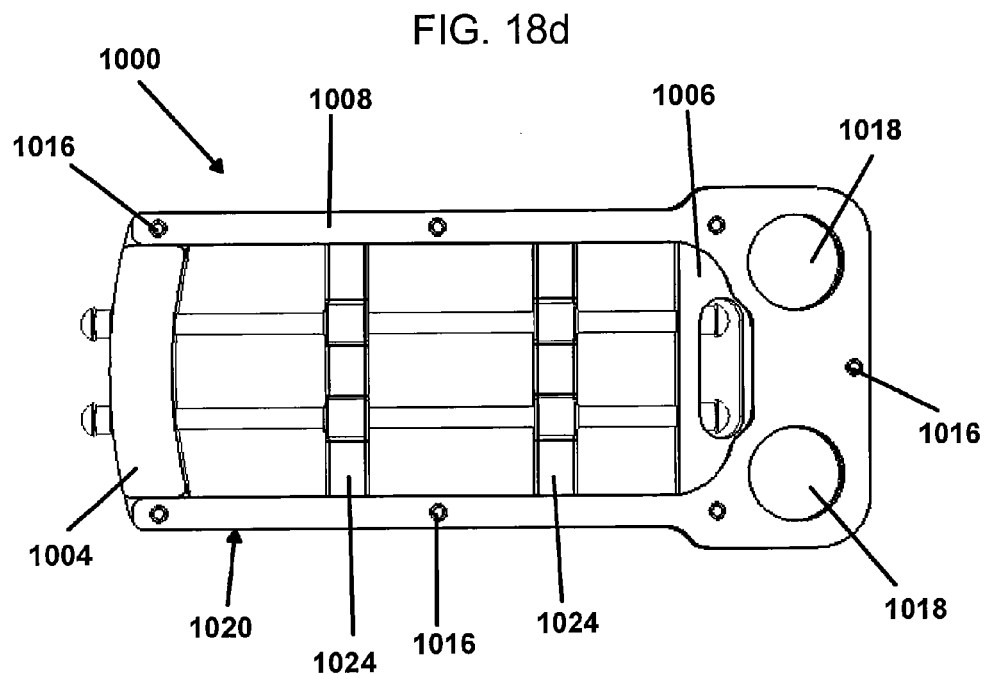

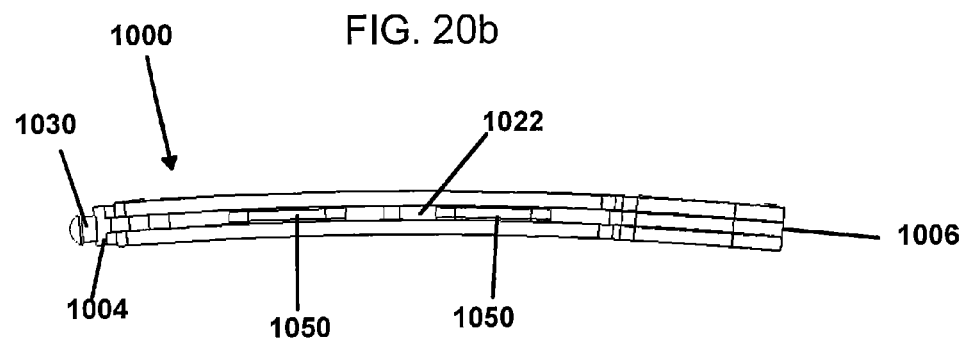
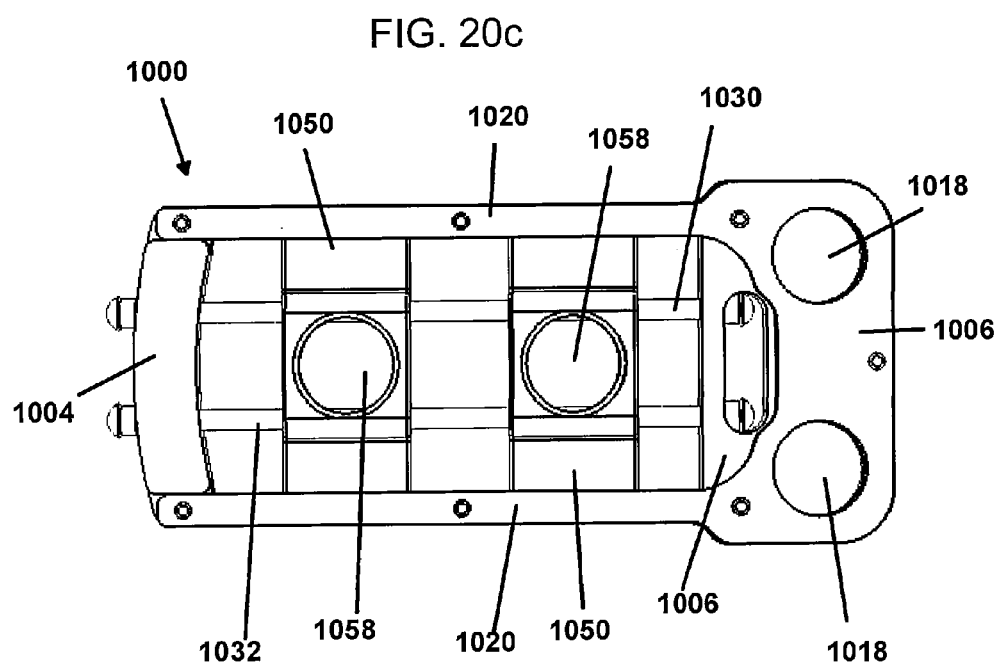

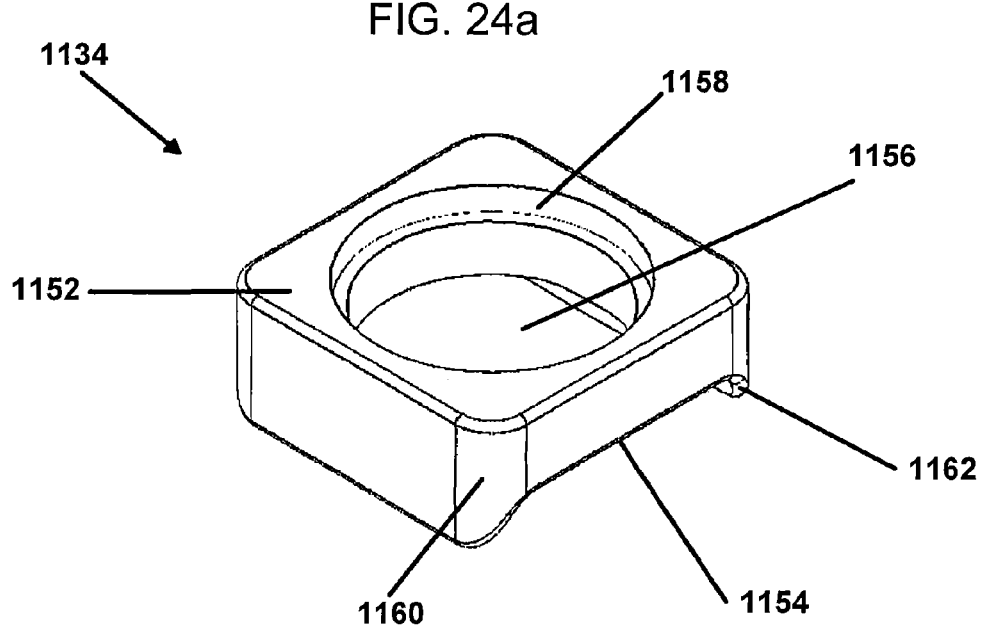
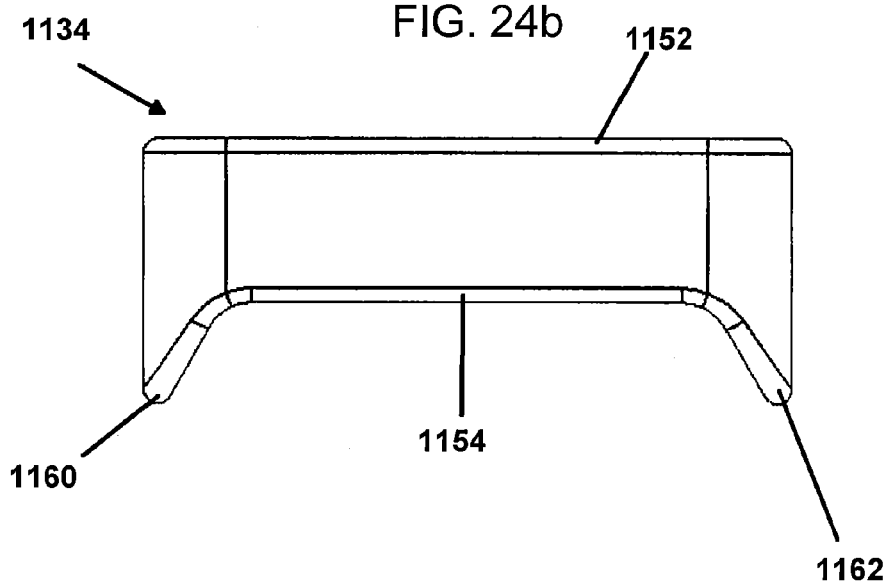

DYNAMIC SPINAL PLATING SYSTEM

CROSS REFERENCE TO RELATED APPLICATIONS

This application is a 371 National Phase of PCT International Application No. PCT/US2012/045023 filed on Jun. 29, 2012, and published in English as WO 2013/003756 A1 on Jan. 3, 2013, which claims priority benefit under 35 U.S.C. §119(e) of U.S. provisional patent application No. 61/502,538 filed Jun. 29, 2011, the entire disclosures of which are incorporated herein by reference.

BACKGROUND OF THE INVENTION

The present invention relates generally to a spinal plate and, in particular, to a dynamic cervical plate. The human spine is made of 7 cervical, 12 thoracic, 5 lumbar vertebrae and the sacrum. Between each vertebral body is the intervertebral disc that connects the two adjacent vertebrae. The very first and the second vertebrae, C1 and C2 respectively, connect to the skull superiorly and the last lumbar vertebrae, L5, connects to the sacrum inferiorly. The cervical portion of the spine is made of 7 vertebrae C1 through C7. The intervertebral disc can become damaged with age or trauma resulting in degenerative disc disease, disc herniation, loss of disc height which ultimately can lead to nerve or spinal cord impingement causing neurologic symptoms, such as radiating pain, numbness, tingling and motor weakness. Degenerative disc disease can also cause chronic neck pain. Various treatment modalities are used to remedy this problem including a surgical procedure called anterior cervical discectomy and fusion (ACDF). In this procedure the disc is removed, then an interbody spacer consisting of a bone or cage is placed to enhance the fusion process as well as to maintain the disc space height. A cervical plate may then be fixed to the anterior aspect of the spine with screws to maintain the lordotic sagittal alignment. Cervical plates can be static or dynamic. Static plates are rigid, and do not allow settling of the vertebrae. Dynamic plates have some degree of movement in the superior inferior direction such that its length changes to a limited degree. This movement allows the dynamic cervical plate to adjust its height as the vertebral body height decreases over time. This helps to load the interbody graft during normal postures, and avoids overloading the interbody graft in extension positions. Some needs, however, remain. For one, visibility of the spine while placing dynamic plates is difficult because of the increased width of these types of plates. Therefore, intermediate screw fixation of the plate becomes a challenge. Often, the intermediate points on the plate cannot be easily moved to accommodate a screw position directly over the vertebra. Finally, because of the lack of visualization, it often becomes difficult to assess whether the vertebrae have been properly aligned with the plate.

SUMMARY OF THE INVENTION

A dynamic spinal plating system is disclosed that can be placed on the anterior aspect of the spine to aid in spinal fusion. This device, although described here for cervical spine, can be easily adapted to plate any of the other spinal levels. The plate invention maximizes dynamism without sacrificing ease of implantation, increases visibility around and through the plate and minimizes assembly requirements. In one aspect of the present invention provided herein, is a dynamic spinal plating system including a plate with superior and inferior ends, two lateral sides connecting the superior and inferior ends to form an opening, and at least one bone attachment mechanism transverse the opening. The superior end also including one screw hole. The two lateral sides each including a slot which allow for bone attachment mechanisms to pass through and to slide along in a direction relatively perpendicular to the at least two lateral sides. The platforms may include screw holes that allow it to be fixed to the vertebral body or connect to another plate. The vertebral platform may be fixed to the vertebral body through its own screw holes. The dynamism may be achieved by any of the multiple possible designs that are described in the following drawings. Several possible embodiments of this plate design are shown in the following diagrams.

The disclosed invention may also work well for other spinal levels including in the anterior thoracic and lumbar spine regions. Appropriate sizing of the device and the fixation screws will be necessary to account for the resultant larger forces and, off-center placement that are typically seen in these spine regions. Further the disclosed plating system may also be used in a ligamentous repair. When multiple disc replacements are performed the anterior longitudinal ligament is sacrificed and the spine becomes more kyphotic with time. The disclosed plating system may be used in motion sparing procedures when the ligaments are sacrificed to help maintain a more lordotic position after the longitudinal ligament has been sacrificed.

The invention may also include a screw that has two or more vertical tabs of metal such that the tabs have a cantilever type resistance to forces perpendicular to it. The screw hole which may be on any part of the inventive plate may have a stop at the anterior portion of the screw hole such that the stop forms a circular lip protruding inwardly. In operation, the screw is placed through the screw hole with the inner edges of the screw hole pushing the vertical tabs of the screw and then as soon as the anterior edge passes through a lip on the screw, the vertical tabs may snap outward and prevent any backing out of the screw to occur. Unlike currently used plating systems the dynamic spinal plating system of the present invention lacks a hard stop, in other words as the spine settles with currently used plating systems the plates suddenly stop at certain points, whereas with the present invention the dynamic spinal plating system continues to slide with the patient's movements. Finally, the invention includes a method of implantation and a method of fabricating the dynamic spinal plating system.

BRIEF DESCRIPTION OF THE DRAWINGS

FIG. 1*f* shows another embodiment of the head plate and a screw plate of the dynamic cervical plating system from a top view, in accordance with an aspect of the present invention;

FIG. 1*g* shows another embodiment of the head plate and two screw plates of the dynamic cervical plating system from a top view, in accordance with an aspect of the present invention;

FIG. 1*h* shows another embodiment of the head plate and two screw plates of the dynamic cervical plating system from a top view, in accordance with an aspect of the present invention;

FIG. 8a is a side view of one of the fastener embodiments of FIG. 7d, in accordance with an aspect of the present invention;

FIG. 8b is a side perspective view of another fastener embodiment, in accordance with an aspect of the present invention;

FIG. 9b is a bottom perspective view of the fastener seat of FIG. 9a, in accordance with an aspect of the present invention;

FIG. 9c is a bottom view of the fastener seat of FIG. 9a, in accordance with an aspect of the present invention;

FIG. 10a is a top perspective view of another embodiment fastener seat of another one of the fastener embodiments of FIG. 7d, in accordance with an aspect of the present invention;

FIG. 10b is a top view of the fastener seat of FIG. 10a, in accordance with an aspect of the present invention;

FIG. 14b is a top view of the plating system of FIG. 14a, in accordance with an aspect of the present invention;

FIG. 18c is a side view of the embodiment of FIG. 18b, in accordance with an aspect of the present invention;

FIG. 18d is a top view of the embodiment of FIG. 18b, in accordance with an aspect of the present invention;

FIG. 20b is a side view of the embodiment of FIG. 20a, in accordance with an aspect of the present invention;

FIG. 20c is a top view of the embodiment of FIG. 20a, in accordance with an aspect of the present invention;

FIG. 24a is a top perspective view of a fastener seat of FIG. 15b, in accordance with an aspect of the present invention;

FIG. 24b is a side view of the fastener seat of FIG. 17a, in accordance with an aspect of the present invention;

DETAILED DESCRIPTION FOR CARRYING OUT THE INVENTION

In this application, the words proximal, distal, anterior, posterior, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body.

Figure 1A:
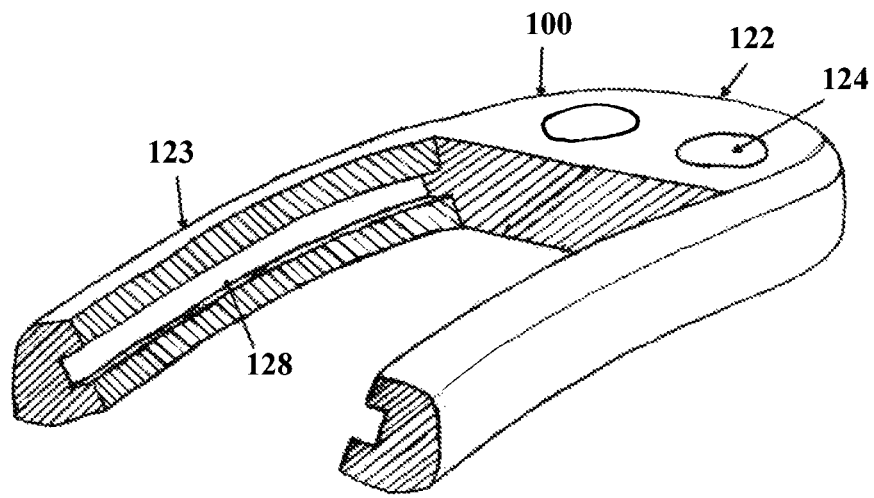
FIG. 1a shows one embodiment of the head plate of the dynamic cervical plating system from a top perspective view, in accordance with an aspect of the present invention.

Referring to the drawings, wherein like reference numerals are used to indicate like or analogous components throughout the several views, FIG. 1a shows one embodiment of the partial head plate 100 of the dynamic cervical plating system. The head plate 100 has a proximal end 122 with two proximal end screw holes 124 and a distal end (not shown), and two lateral shafts 123. There is also a groove or slot 128 along the inner aspect of the lateral shafts.

Figure 1B:
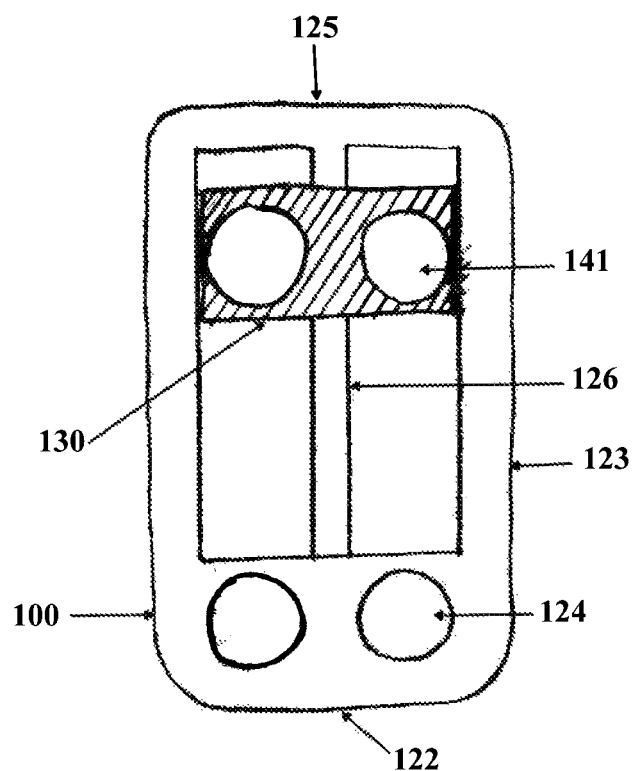
FIG. 1b shows another embodiment of the dynamic cervical plating system from a top view, in accordance with an aspect of the present invention.

FIG. 1b shows another embodiment of the dynamic cervical plating system including a head plate 101, two lateral shafts 123 and an intervening shaft 126. The distal end 125 and the proximal end 122 with the proximal end screw holes 124 are also shown. A slidable screw plate 130 is also shown with the screw plate screw holes 141.

Figure 1C:
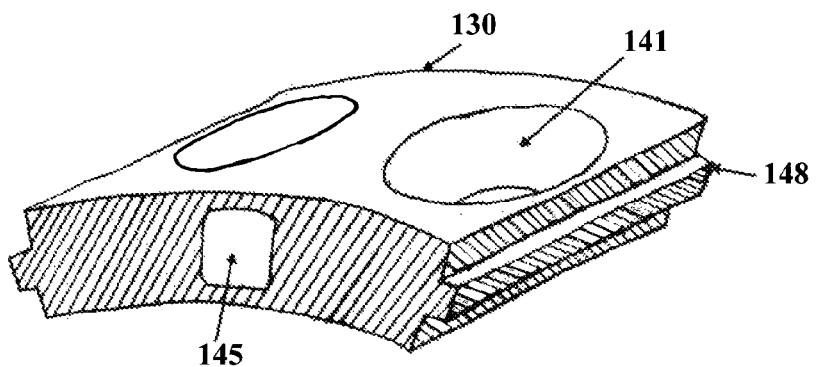
FIG. 1c shows one embodiment of the screw plate of the dynamic cervical plating system from a top perspective view, in accordance with an aspect of the present invention.

FIG. 1c shows one embodiment of the screw plate 130 of the dynamic cervical plating system from the top angled view. It has two screw plate screw holes 141, two lateral flanges or tabs 148 that may slide along the slots of the head plate (128 in FIG. 1a). Also seen is an intervening shaft tunnel 145 that may accommodate an intervening shaft similar to the one shown in FIG. 1b.

Figure 1D:
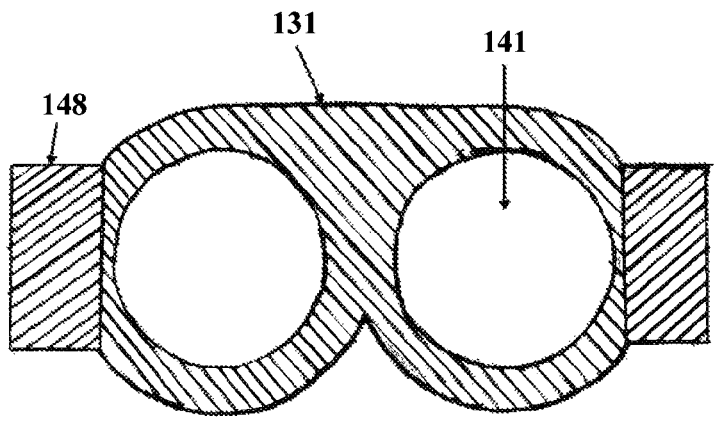
FIG. 1d shows another embodiment of the screw plate of the dynamic cervical plating system from a top view, in accordance with an aspect of the present invention.

FIG. 1d shows another embodiment of the screw plate 131 of the dynamic cervical plating system. Screw plate 131 may include two screw plate screw holes 141, two lateral flanges or tabs 148 that can slide along the slots of the head plate (128 in FIG. 1a).

Figure 1E:
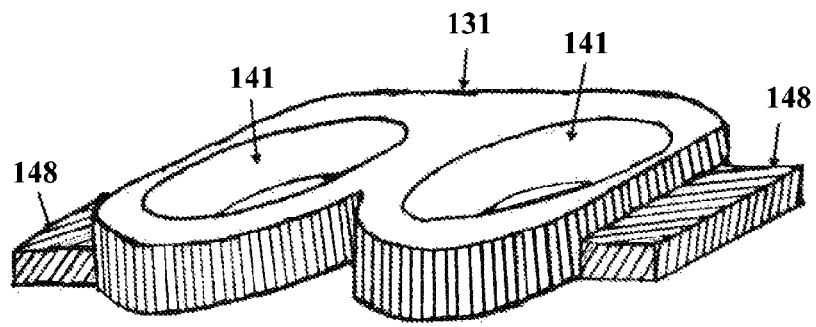
FIG. 1e shows the screw plate of FIG. 1d, from a top perspective view, in accordance with an aspect of the present invention.

FIG. 1e shows the screw plate 131 of FIG. 1d. Screw plate 131 may include two screw plate screw holes 141 and two lateral flanges or tabs 148 that are sized to slide along the slots of the head plate (128 in FIG. 1a).

FIG. 1f shows another embodiment of the head plate 100 and a screw plate 131 of the dynamic cervical plating system with the head plate 100 having two lateral shafts 123. The distal end 125 and the proximal end 122 that includes two proximal end screw holes 124 are also shown. The slidable screw plate 131, as shown in FIG. 1d and FIG. 1e, is also seen with the screw plate screw holes 141.

FIG. 1g shows another embodiment of the head plate 100 and two screw plates 132 of the dynamic cervical plating system. The head plate 100 has two lateral shafts 123, a distal end 125 and a proximal end 122 with two proximal end screw holes 124. A slidable screw plate 132 that has one central screw hole 141 is also shown.

FIG. 1h shows another embodiment of the head plate 102 and two screw plates 133 of the dynamic cervical plating system from the top view. The head plate 102 has two lateral shafts 123, a distal end 125 and a proximal end 122 with two proximal end screw holes 124. The slidable screw plates 133 each having one screw hole 146 are located eccentrically towards one of the lateral shafts 123.

Figure 2A:
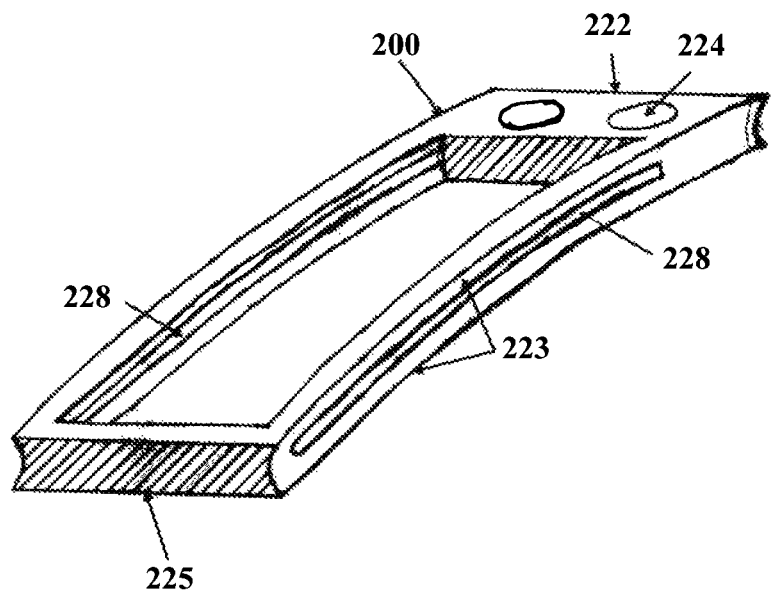
FIG. 2*a* shows another embodiment of the head plate of the dynamic cervical plating system having continuous lateral shaft slots along the lateral shafts, as seen from a top perspective view, in accordance with an aspect of the present invention.

FIG. 2a shows another embodiment of the head plate 200 of the dynamic cervical plating system having continuous lateral shaft slits or slots 228 along the lateral shafts 223. The head plate 200 may include two lateral shafts 223, a distal end 225 and a proximal end 222 with two proximal end screw holes 224.

Figure 2B:
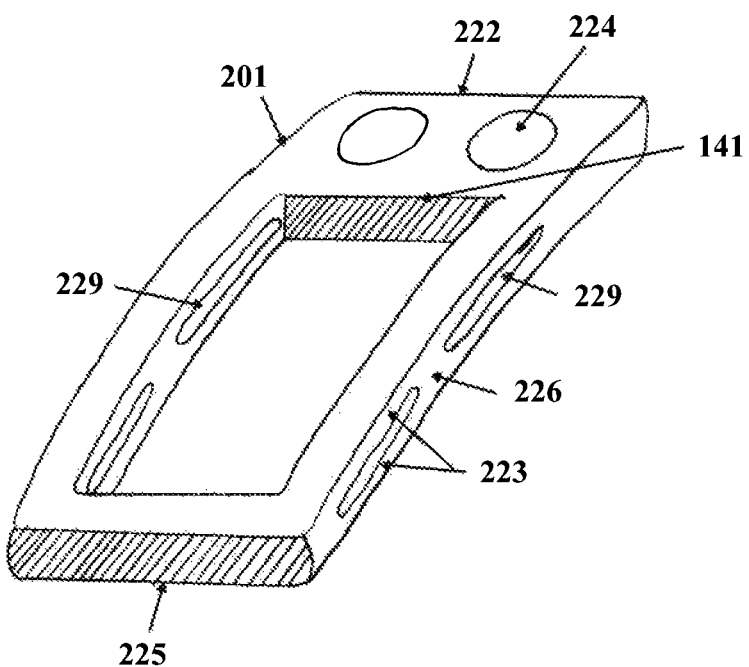
FIG. 2*b* shows another embodiment of the head plate of the dynamic cervical plating system having discontinuous lateral shaft slots along the lateral shafts, as seen from a top perspective view, in accordance with an aspect of the present invention.

FIG. 2b shows another embodiment of the head plate 201 of the dynamic cervical plating system having discontinuous lateral shaft slots 229 along the lateral shafts. The head plate 201 generally has two lateral shafts 223, a distal end 225 and a proximal end 222 with two proximal end screw holes 224. The lateral shaft slots 229 are discontinuous and are interrupted by lateral shaft bridges 226 connecting the anterior and posterior parts of the lateral shafts 223.

Figure 2C:
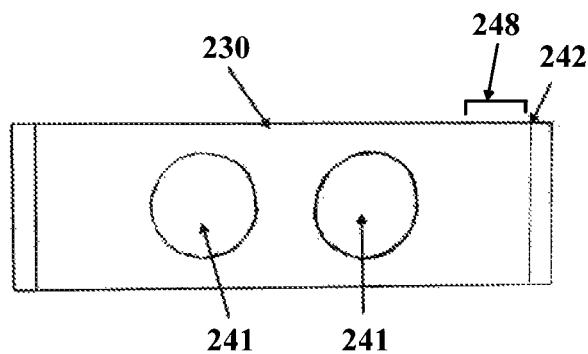
FIG. 2*c* shows another embodiment of the screw plate of the dynamic cervical plating system from a top view, in accordance with an aspect of the present invention.

FIG. 2c shows another embodiment of the screw plate 230 of the dynamic cervical plating system. It has at least two screw holes 241, two lateral tabs 248 that can slide along the slots on the lateral shafts of the head plate (228 in FIGS. 2a and 229 in FIG. 2b). It also includes two lateral lips 242 that allow the screw plate 230 to slide in a proximal-distal direction at the interface of its tab 248 and the lateral slots of the head plate (228 in FIG. 2a or 229 in FIG. 2b) while allowing for limited lateral sliding movement.

Figure 2D:
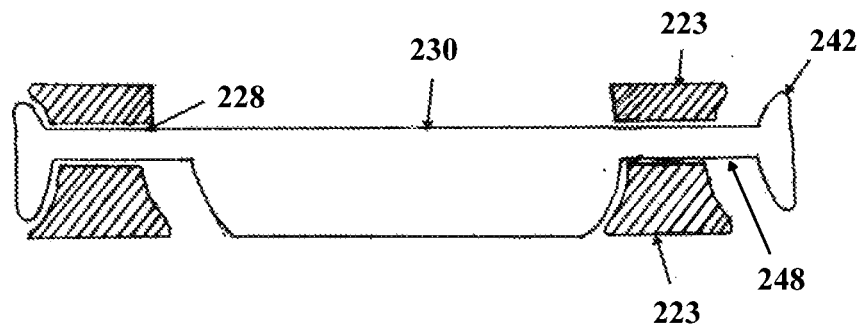
FIG. 2*d* shows a sectional view of the screw plate shown in FIG. 2*c* that may be slidably attached to the head plates shown in FIG. 2*a* or FIG. 2*b*, in accordance with an aspect of the present invention.

FIG. 2d shows the screw plate of FIG. 2c. It is shown to have two lateral tabs 248 that can slide along the slots on the lateral shafts of the head plate (228 in FIGS. 2a and 229 in FIG. 2b). It also shows two lateral lips or stops 242 that allow the screw plate 230 to slide in the proximal-distal direction at the interface of its tab 248 and the lateral slots of the head plate (228 in FIG. 2a or 229 in FIG. 2b) while also allowing for limited lateral sliding or translational movement.

Figure 2E:
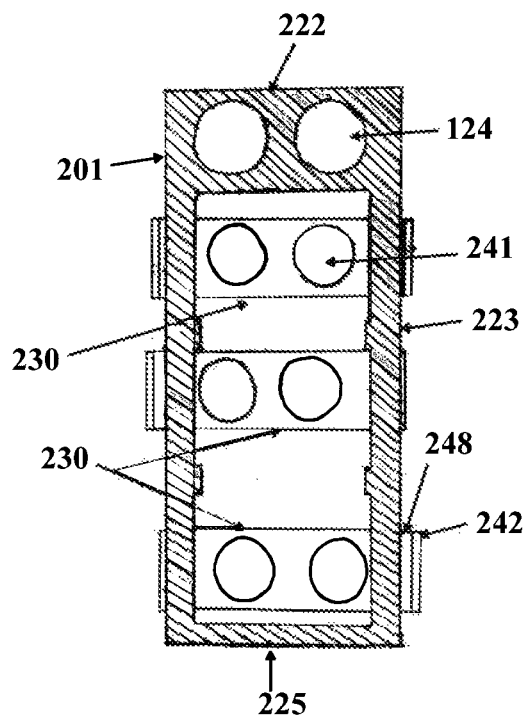
FIG. 2*e* shows the head plate, as shown in FIG. 2*b* with three screw plates, as shown in FIG. 2*c* and FIG. 2*d*, as seen from a top perspective view, in accordance with an aspect of the present invention.

FIG. 2e shows the head plate 201, as shown in FIG. 2b with three screw plates 230. The head plate 201 has two lateral shafts 223, a distal end 225 and a proximal end 222 with two proximal end screw holes 124. The slidable screw plates 230 each have two screw holes 241, two lateral tabs 248 and lateral lips 242 which are attached to lateral aspects of each tab 248. The relative positions of the three screw plates 230 with respect to the head plate 201 exhibit the proximal-distal and lateral slidability allowed by the design of FIG. 2e.

Figure 2F:
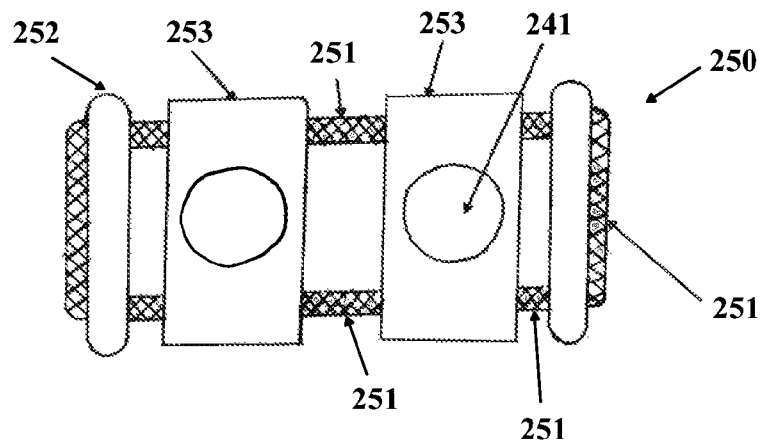
FIG. 2*f* shows another embodiment of the screw plate of the dynamic cervical plating system from top a view, in accordance with an aspect of the present invention.

FIG. 2f shows another embodiment of the screw plate 250 of the dynamic cervical plating system. It has two screw sub-plates 253 (although it is contemplated for some embodiments to include a single subplate) with screw holes 241 that are slidebly connected to a wire or other flexible wire like construct 251. The wire 251 which is shown for example purposes, is in the shape of a rectangular loop and passes twice through two lateral tension bars 252, once from a medial to lateral direction at one end of a lateral tension bar 252 then lateral to medial distally at the other end of the lateral tension bar 252. The wire 251 also passes through slots in the head plate (not shown here, for example 228 in FIG. 2a) such that the shafts (not shown here, for example 223 of FIG. 2a) of the head plate (not shown here, for example, 200 in FIG. 2a) separate the lateral tension bar 252 from the screw sub-plate 253 to assist in keeping the two lateral tension bars separated and relatively taut while allowing for movement of the screw plate 250 in the proximal-distal direction following implantation.

Figure 2G:
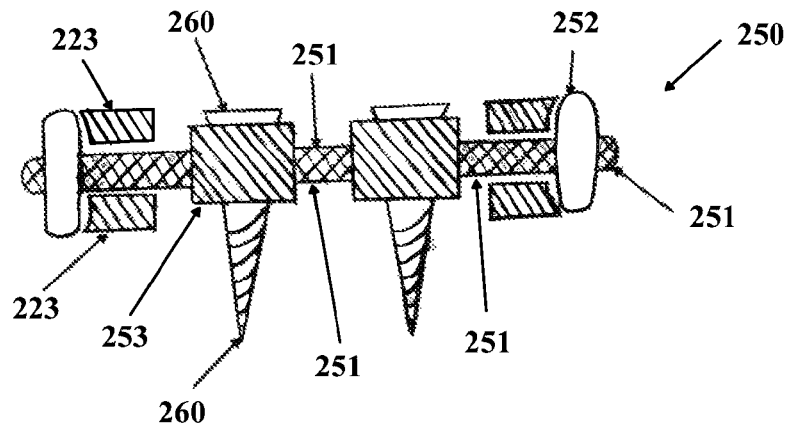
FIG. 2*g* is a cross-sectional view of the screw plate seen in FIG. 2*f* of the dynamic cervical plating system, in accordance with an aspect of the present invention.

FIG. 2g shows the screw plate 250 (also seen in FIG. 2f) of the dynamic cervical plating system from a cross-sectional view. For example purposes two screw sub-plates 253 are seen with a screw 260 in place in each and that are slidebly connected to a wire 251 or other similar construct. The wire 251 is in a shape of a rectangular loop and passes twice (only one wire passing through the lateral tension bars is seen from this view) through two lateral tension bars 252, once from medial to lateral direction at one end of a lateral tension bar 252 then from a lateral to medial direction distally at the other end of the lateral tension bar 252. The wire also passes through slots (not shown here, for example 228 in FIG. 2a) in the head plate (not shown here, for example, 200 in FIG. 2a) such that the shafts 223 of the head plate separate the lateral tension bars 252 from the screw sub-plate 253 and also the shaft 223 of the head plate keep the two lateral tension bars separated and relatively taut while allowing for movement of the screw plate 250 in the proximal-distal direction following placement on the spine.

Figure 2H:
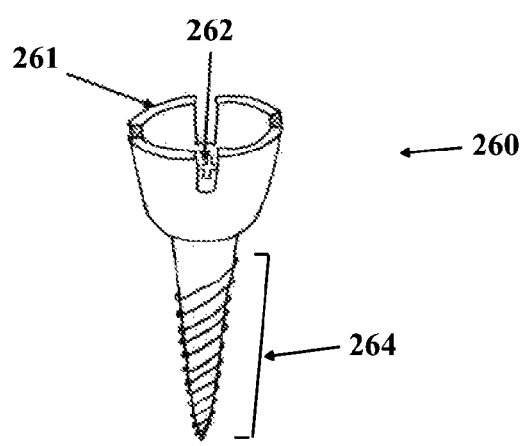
FIG. 2*h* is a perspective view of a fixation screw, to be used with the dynamic cervical plating system, in accordance with an aspect of the present invention.

FIG. 2h shows an embodiment of the fixation screw 260 that has a slotted head 262, a body or threaded shaft 264 and four vertical flaps or tabs 261. For example purposes, four flaps or tabs are shown but more or less may be used depending on the clinical situation. The flaps 261 are configured to provide some elastic resistance to applied forces.

Figure 2I:
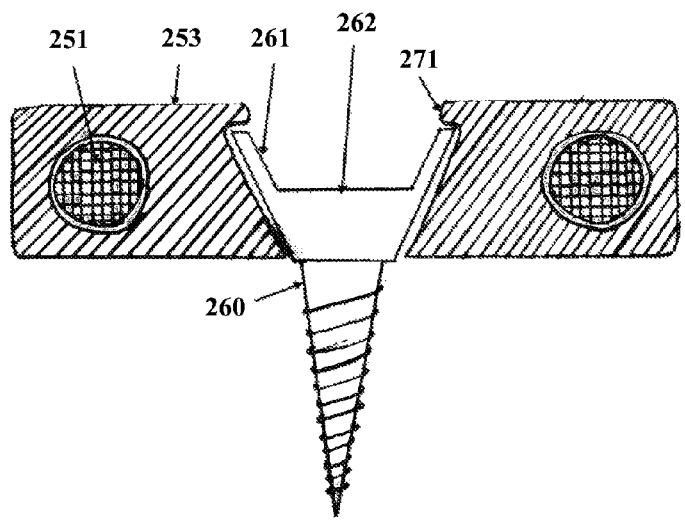
FIG. 2*i* is a cross-sectional view of the screw in FIG. 2*h* in place in the screw plate of FIG. 2*f*, in accordance with an aspect of the present invention.

FIG. 2i shows the screw 260 that has a head 262 with the four vertical tabs as described above. As seen, the screw 260 is in place in the screw hole of a screw sub-plate 253 (but it may be adapted to fit a screw hole on any of the devices, such as screw plates, head plates, etc.) and is protected against backing out by the combination of the vertical tab 261 and the stop 271 on the screw sub-plate 253. The screw sub-plate 253 is attached slidably to the wire 251. A possible method for removing the screw 260 may be to cut the wire 251 (see FIG. 2f also) to release the screw sub-plates 253 and then unscrew the screw 260 to remove it with the screw sub-plate 253 as a unit. The remaining parts of the screw plate, namely the wires 251 and the lateral tension bars 252 can then be removed easily through the slots in the lateral shafts of the head plate (see FIG. 2a).

Figure 3A:
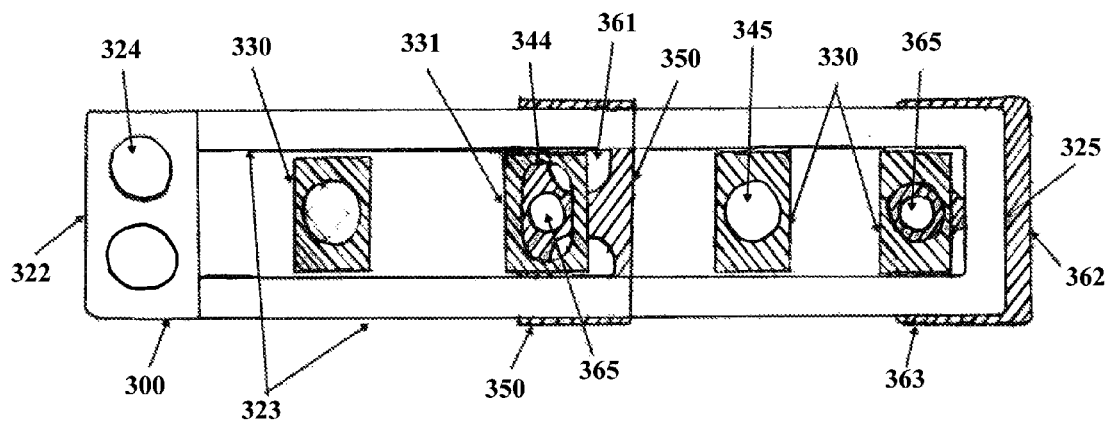
FIG. 3*a* shows another embodiment of the dynamic cervical plating system, as seen from a top view, in accordance with an aspect of the present invention.

FIG. 3a shows another embodiment of the dynamic cervical plating system with head plate 300, three screw plates 330 with circular screw hole 345, one elongated hole screw plate 331 with an elongated screw hole 344 and two vertebral platforms 350. The head plate 300 has two lateral shafts 323, a distal end 325 and a proximal end 322 with two proximal end screw holes 324. The vertebral platform 350 has two vertebral screw holes 361 that fixes the vertebral platform 350 to a vertebral body and, a device interface screw hole 365 that secures the vertebral platform 350 to the screw plate anteriorly and thus to the head plate 300. The slidable screw plate 330 has at least one screw hole 345, and the slidable elongated hole screw plate 331 has at least one elongate screw hole 344 that can be attached to the vertebral body or a vertebral platform 350 through its screw hole 365 such that the combination of the screw plate 330 or 331 and the vertebral body and/or the vertebral plate 350 can slide in the proximal-distal direction as a unit.

Figure 3B:
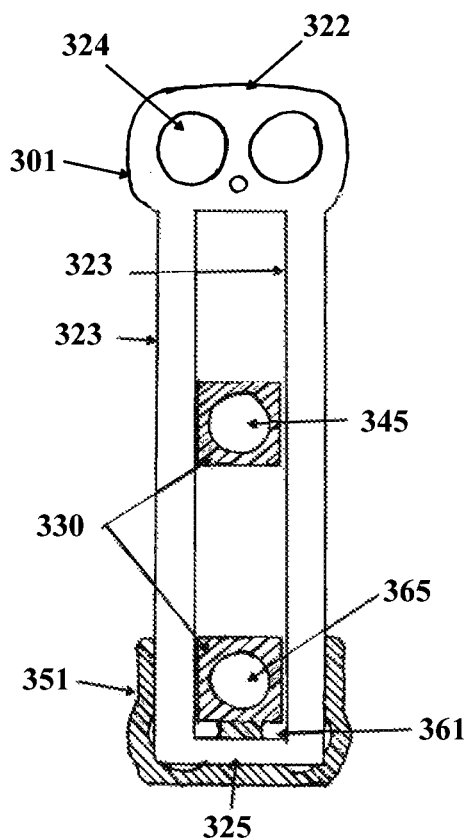
FIG. 3*b* shows another embodiment of the dynamic cervical plating system, as seen from a top view, in accordance with an aspect of the present invention.

FIG. 3b shows another embodiment of the dynamic cervical plating system with a narrower head plate 301, two screw plates 330 with circular screw hole 345 and at least one vertebral platform 351. The head plate 301 has two lateral shafts 323, a distal end 325 and a proximal end 322 with two proximal end screw holes 324. The at least one vertebral platform 351 has two vertebral screw holes 361 that attaches the vertebral platform 351 to the vertebral body and, a device interface screw hole 365 that attaches the vertebral platform 351 to a screw plate 330 anteriorly. The slidable screw plate 330 having one screw hole 345 can be attached to the vertebral body or a vertebral platform 351 through its device interface screw hole 365 such that the combination of the screw plate 330 and the vertebral body or the vertebral plate 351 can slide in the proximal-distal direction.

Figure 3C:
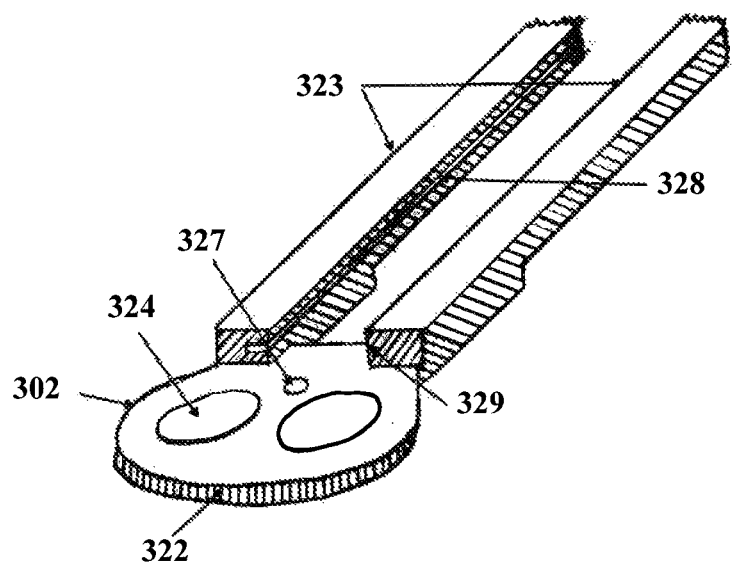
FIG. 3*c* shows another embodiment of the head plate of the dynamic cervical plating system, as seen from the top perspective view, in accordance with an aspect of the present invention.

FIG. 3c shows another embodiment of the dynamic cervical plating system with the head plate 302, to add or remove screw plates (330 in FIGS. 3a, 3b, 3e and 3f) from the system. The head plate 302 has two lateral shafts 323, a distal end (not shown) and a proximal end 322 with two proximal end screw holes 324. The lateral shafts 323 have grooves or slots along the inner aspect that proximally end in an opening 329 which allows for the adding of screw plates (330 in FIGS. 3a, 3b, 3e and 3f). There is also a stop screw hole 327 or other mechanism on the proximal end of the head plate that prevents the screw plates (330 in FIGS. 3a, 3b, 3e and 3f) from disengaging from the assembly once added to the construct.

Figure 3D:
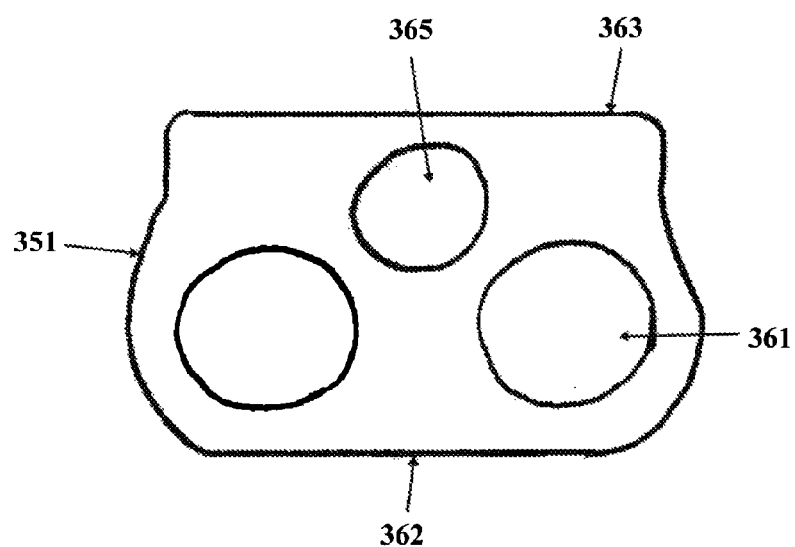
FIG. 3*d* is a top view of one embodiment of the vertebral platform of the dynamic cervical plating system, that attaches to the head plate of FIG. 3*a* and FIG. 3*b*, in accordance with an aspect of the present invention.

FIG. 3d shows an embodiment of the vertebral platform 351 of the dynamic cervical plating system. The vertebral platform 351 includes a head part 362 and a tail part 363, two vertebral screw holes 361 that attaches the vertebral platform 351 to a vertebral body and, a device interface screw hole 365 that is used to attach the vertebral platform 351 to the screw plate (330 or 331 in FIGS. 3a, 3b, 3e and 3f) anteriorly and also to the head plate (300, 301 and 302 in FIGS. 3a, 3b and 3c respectively). The slidable screw plate (330 or 331 in FIGS. 3a, 3b, 3e and 3f) can be attached to the vertebral body or a vertebral platform 351 through its device interface screw hole 365 such that the combination can slide in the proximal-distal direction as a unit.

Figure 3E:
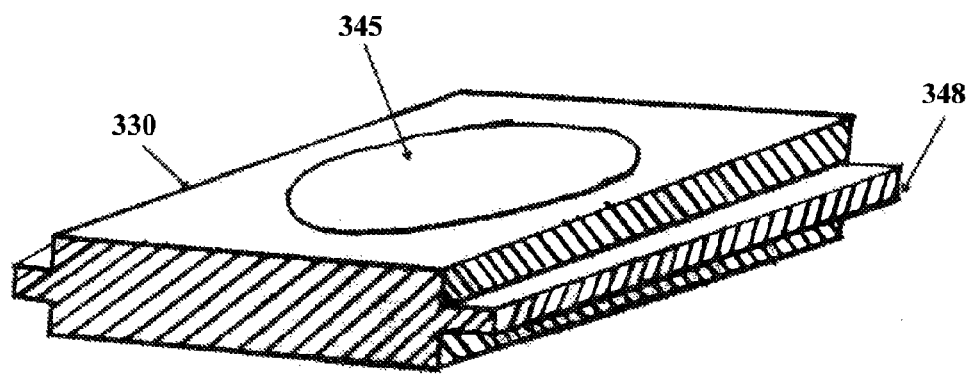
FIG. 3*e* is a top view of one embodiment of the screw plate of the dynamic cervical plating system, that attaches to the head plate of FIG. 3*a* and FIG. 3*b*, in accordance with an aspect of the present invention.

FIG. 3e shows another embodiment of the slidable screw plate 330 of the dynamic cervical plating system that movingly attaches to the head plate (300, 301 and 302 in FIGS. 3a, 3b and 3c respectively). The screw plate 330 also includes at least one through screw hole 345 and outward projecting tabs 348 for slidable engagement with a head plate.

Figure 3F:
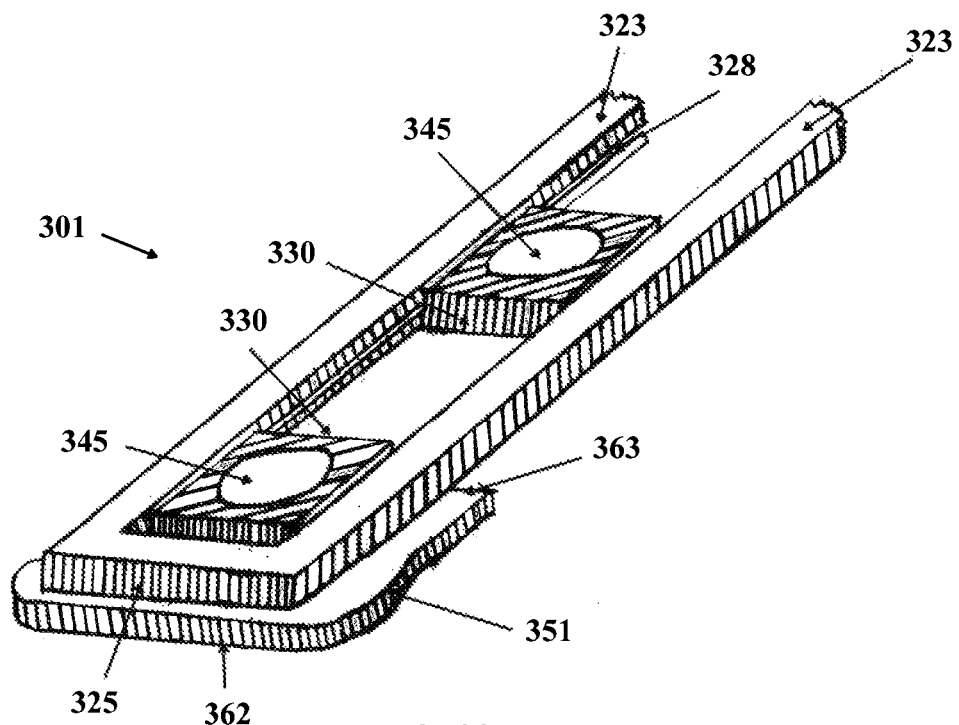
FIG. 3*f* shows another embodiment of the head plate, two screw plates and a vertebral platform of the dynamic cervical plating system, as seen from a top perspective view, in accordance with an aspect of the present invention.

FIG. 3f shows another view of a distal part of the device shown in FIG. 3c. Seen is the distal portion of the head plate 301, two screw lateral shafts 323, a vertebral platform 351 and two screw plates 330. The head plate 301 includes two grooves or slots 328 on the inner aspect of the lateral shafts 323 for engaging the screw plates 330.

Figure 4A:
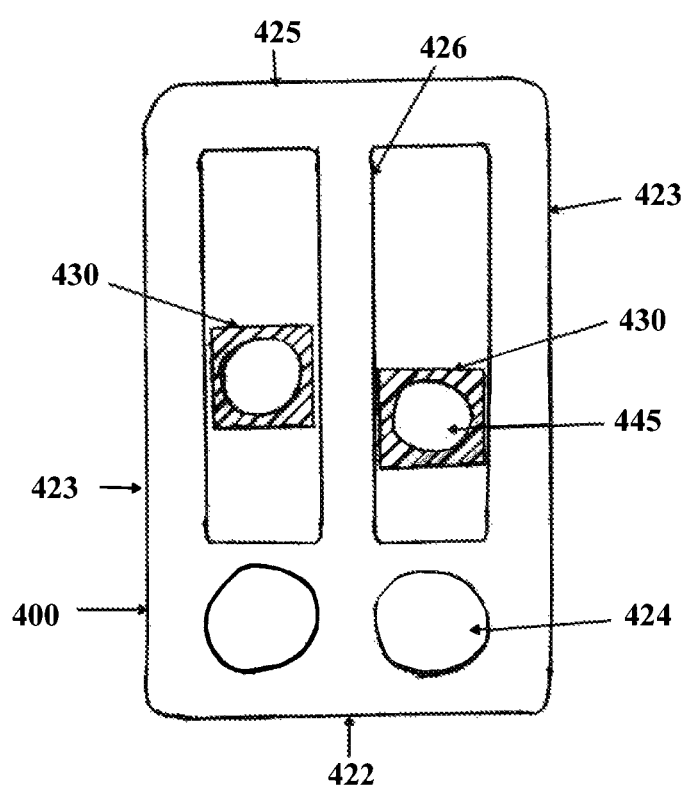
FIG. 4*a* is a top view of another embodiment of the dynamic cervical plating system having a head plate with three shafts and two independently slidable screw plates, in accordance with an aspect of the present invention.

FIG. 4a shows another embodiment of the device, with head plate 400 having three shafts with two lateral shafts 423 and one middle shaft 426 as well as two independently slidable screw plates 430 positioned there between. The distal end 425 and the proximal end 422 with the proximal end screw holes 424 are also shown. The slidable screw plates 430 include screw plate screw holes 445 for bone fixation.

Figure 4B:
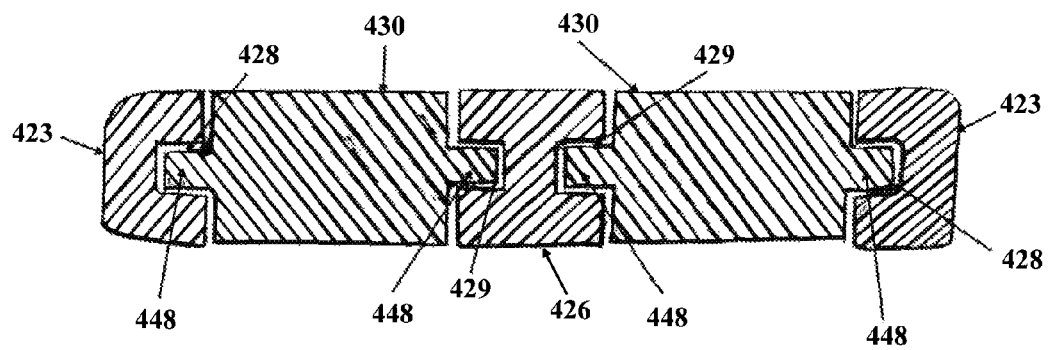
FIG. 4*b* is a cross-sectional view of the device in FIG. 4*a*, through the three shafts and two independently slidable screw plates, in accordance with an aspect of the present invention.

FIG. 4b shows the device in FIG. 4a, from a sectional view through the two lateral shafts 423, one middle shaft 426 and one independently slidable screw plate 430. Flanges or tabs 448 are seen which slidably fit into the lateral shaft grooves or slots 428 on the inner aspect of at least one of the lateral shaft 423 and the opposing middle shaft groove or slot 429 disposed within the middle shaft 426.

Figure 5A:
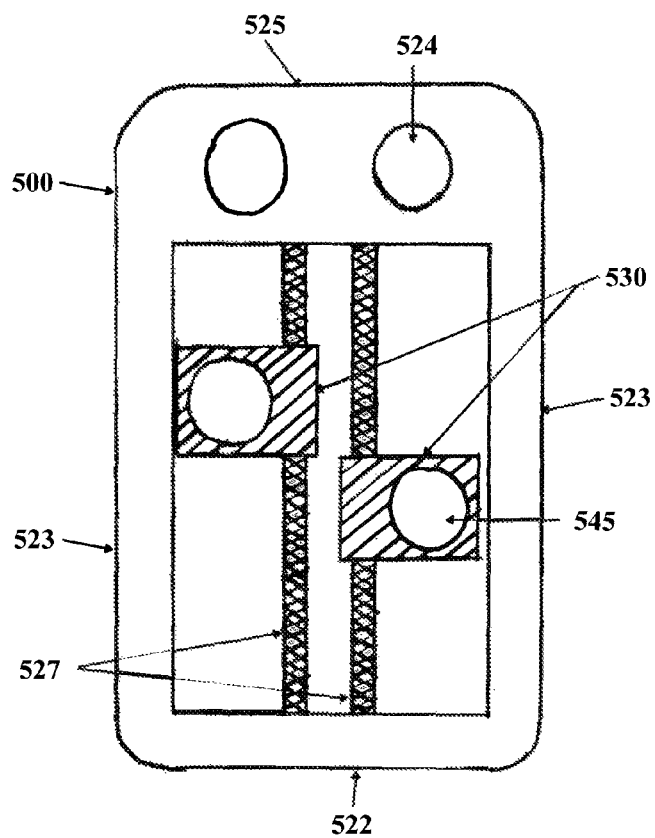
FIG. 5*a* is a top view of another embodiment of the device, with head plate having two shafts and two wires with two independently slidable screw plates, in accordance with an aspect of the present invention.

FIG. 5a shows another embodiment of the device, with a head plate 500 having two shafts 523 and two wires or flexible wire-like constructs 527 with two independently slidable screw plates 530. A distal end 525 and a proximal end 522 with proximal end screw holes 524 are also shown. The slidable screw plate 530 includes screw plate screw holes 545. The screw plates 530 are configured to allow for translational movement along the axis of wires 527.

Figure 5B:
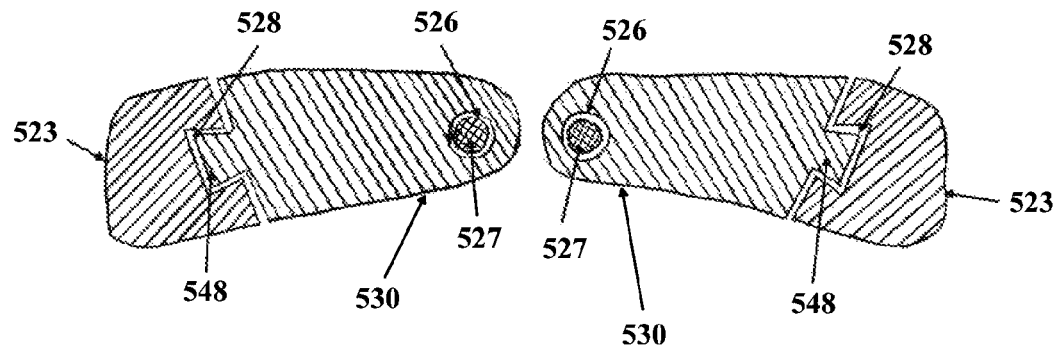
FIG. 5*b* is a cross-sectional view of the device in FIG. 5*a*, through the two shafts, two flexible members and two independently slidable screw plates, in accordance with an aspect of the present invention.

FIG. 5b shows the device in FIG. 5a, from a sectional view through the two shafts 523, two wires 527 and the independently slidable screw plates 530. The screw plates 530 may have a wire tunnel or hole 526 that slidably surrounds the wire and tab or flange 548 on the lateral side which slidably fits into the lateral shaft grooves 528 on the inner aspect of the lateral shaft 523 which enables the screw plates 530 to move in the proximal-distal direction.

Figure 6A:
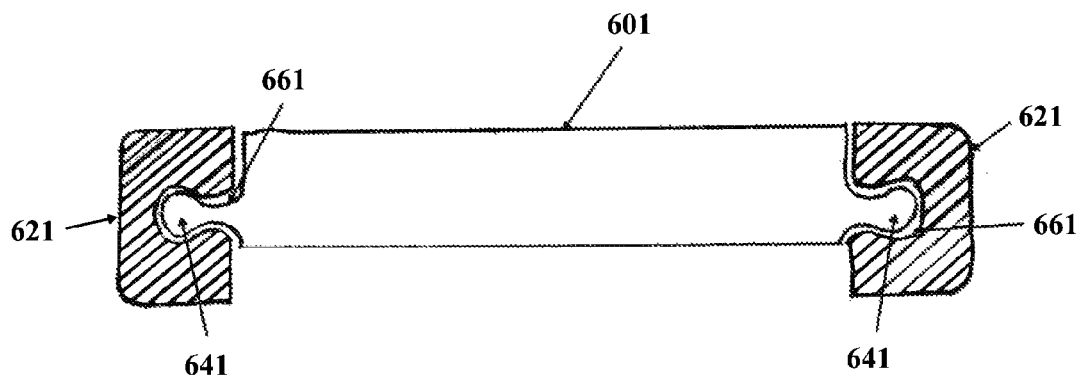
FIG. 6*a* is a cross-sectional view of another embodiment of the screw plate and the lateral shafts assembly of the dynamic cervical plating system through the screw plate and two lateral shafts, in accordance with an aspect of the present invention.
Figure 6B:
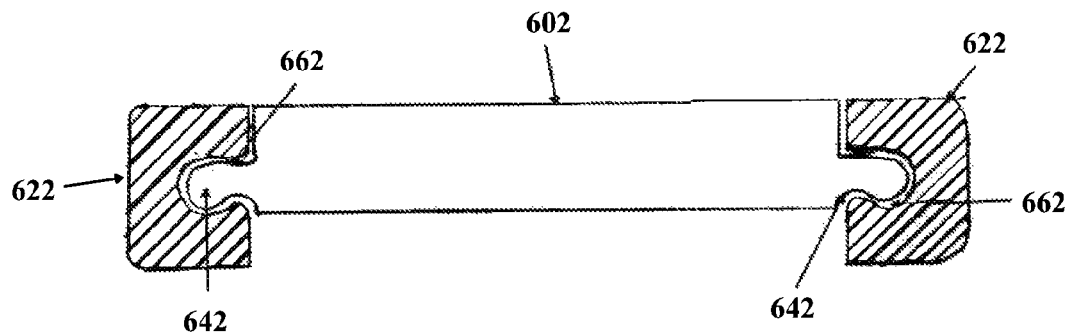
FIG. 6*b* is a cross-sectional view of another embodiment of the screw plate and the lateral shafts of the dynamic cervical plating system through the screw plate and two lateral shafts, in accordance with an aspect of the present invention.
Figure 6C:
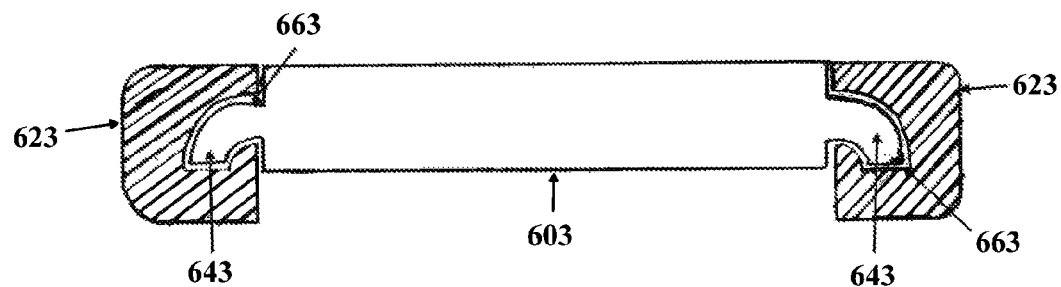
FIG. 6*c* is a cross-sectional view of another embodiment of the screw plate and the lateral shafts assembly of the dynamic cervical plating system through the screw plate and two lateral shafts, in accordance with an aspect of the present invention.
Figure 6D:
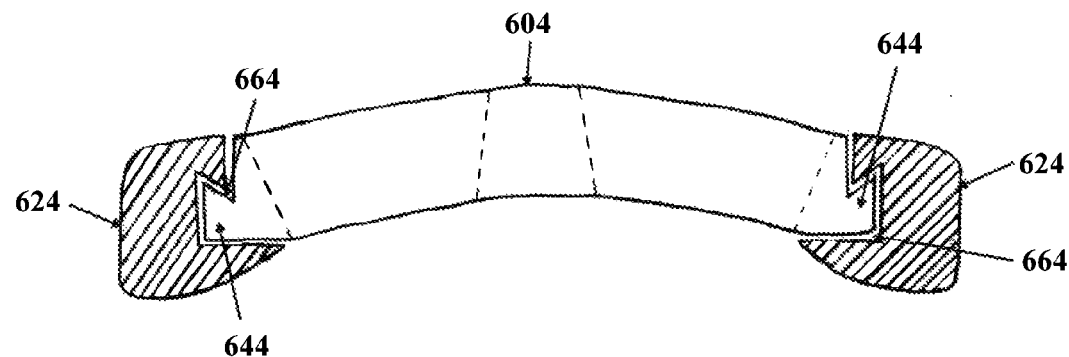
FIG. 6*d* is a cross-sectional view of another embodiment of the screw plate and the lateral shafts assembly of the dynamic cervical plating system through the screw plate and two lateral shafts, in accordance with an aspect of the present invention.
Figure 6E:
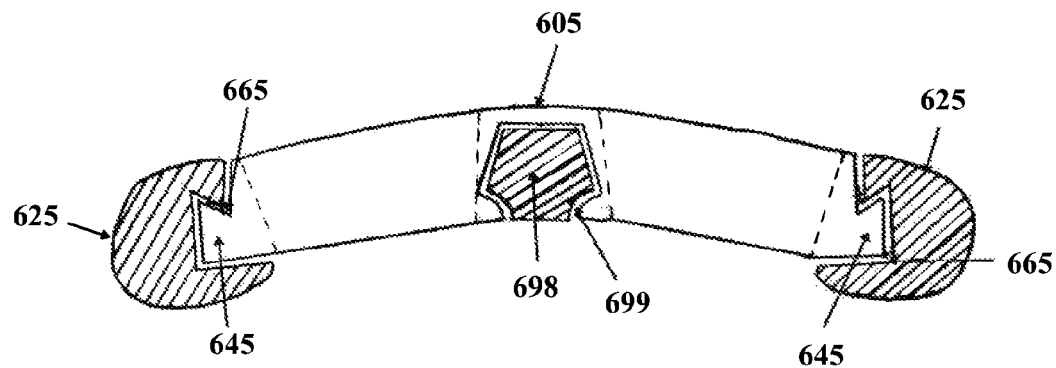
FIG. 6*e* is a cross-sectional view of another embodiment of the screw plate and the lateral shafts assembly of the dynamic cervical plating system through the screw plate and three lateral shafts, in accordance with an aspect of the present invention.
Figure 6F:
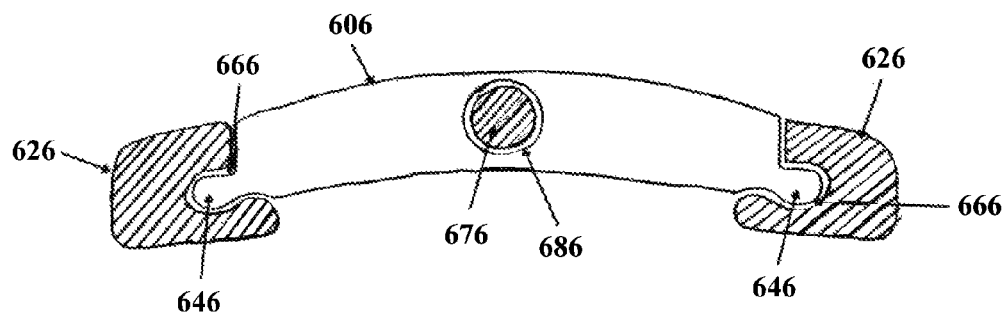
FIG. 6*f* is a cross-sectional view of another embodiment of the screw plate and the lateral shafts assembly of the dynamic cervical plating system through the screw plate and three lateral shafts; in accordance with an aspect of the present invention.
Figure 6G:
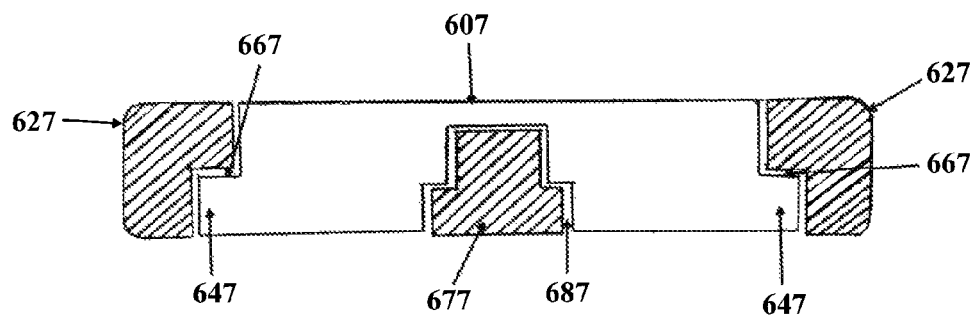
FIG. 6*g* is a cross-sectional view of another embodiment of the screw plate and the lateral shafts assembly of the dynamic cervical plating system through the screw plate and three lateral shafts, in accordance with an aspect of the present invention.
Figure 6H:
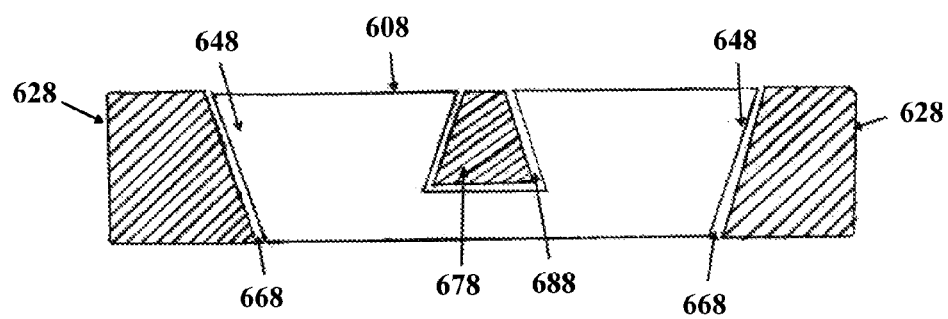
FIG. 6*h* is a cross-sectional view of another embodiment of the screw plate and the lateral shafts assembly of the dynamic cervical plating system through the screw plate and three lateral shafts, in accordance with an aspect of the present invention.
Figure 6I:
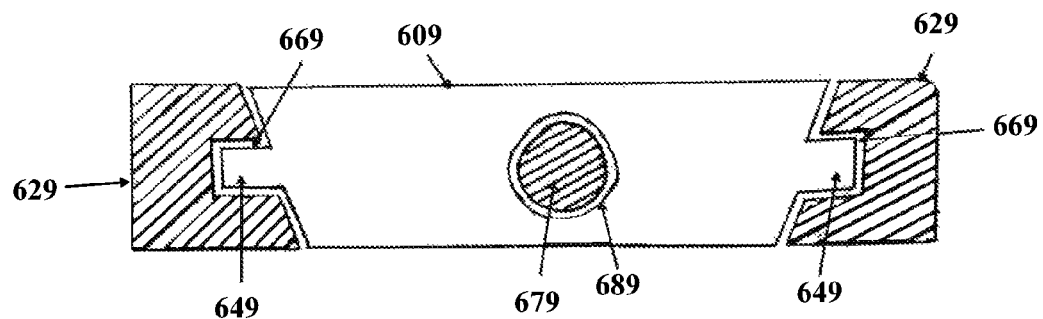
FIG. 6*i* is a cross-sectional view of another embodiment of the screw plate and the lateral shafts assembly of the dynamic cervical plating system through the screw plate and three lateral shafts, in accordance with an aspect of the present invention.
Figure 6J:
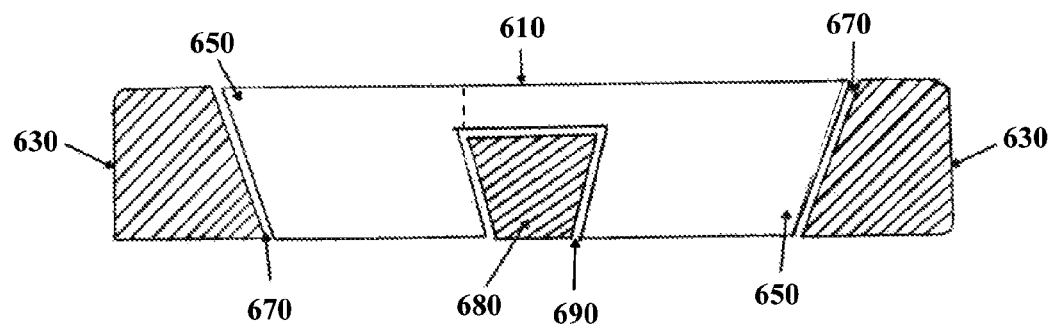
FIG. 6*j* is a cross-sectional view of another embodiment of the screw plate and the lateral shafts assembly of the dynamic cervical plating system through the screw plate and three lateral shafts, in accordance with an aspect of the present invention.
Figure 6K:
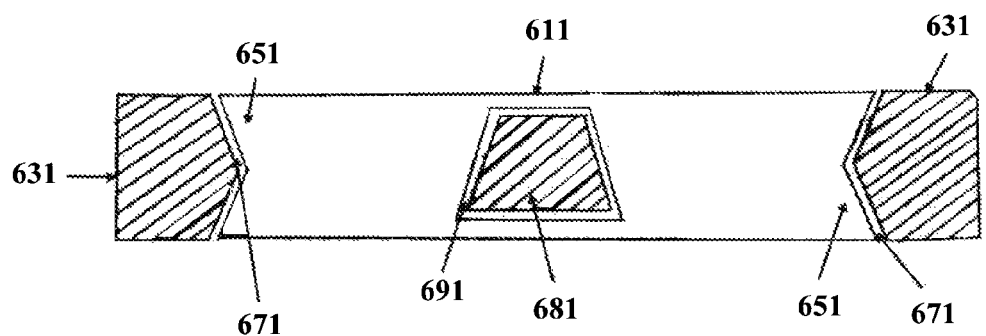
FIG. 6k is a cross-sectional view of another embodiment of the screw plate and the lateral shafts assembly of the dynamic cervical plating system through the screw plate and three lateral shafts, in accordance with an aspect of the present invention.
Figure 6L:
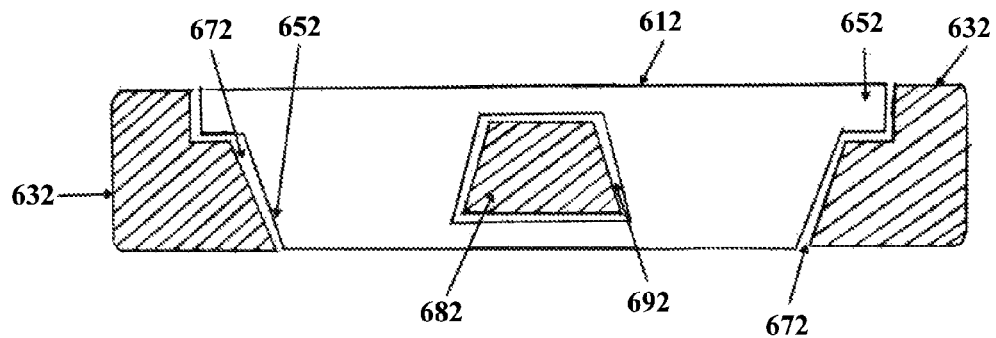
FIG. 6l is a cross-sectional view of another embodiment of the screw plate and the lateral shafts assembly of the dynamic cervical plating system through the screw plate and three lateral shafts, in accordance with an aspect of the present invention.
Figure 6N:
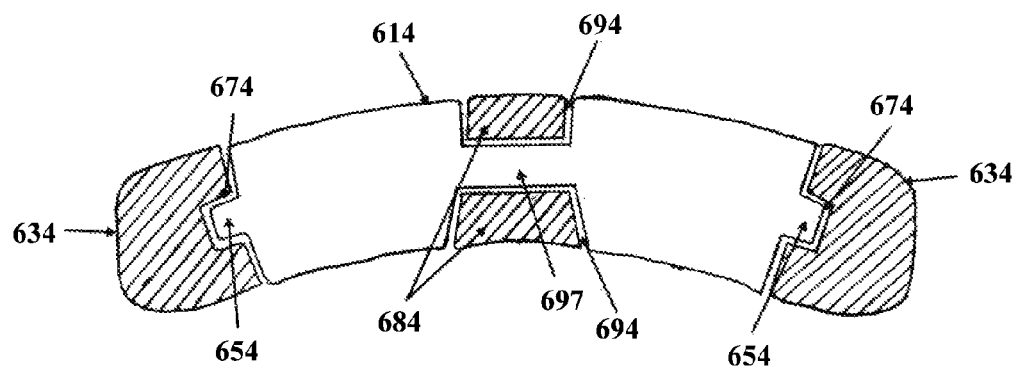
FIG. 6n is a cross-sectional view of another embodiment of the screw plate and the lateral shafts assembly of the dynamic cervical plating system through the screw plate and three lateral shafts, in accordance with an aspect of the present invention.
Figure 6O:
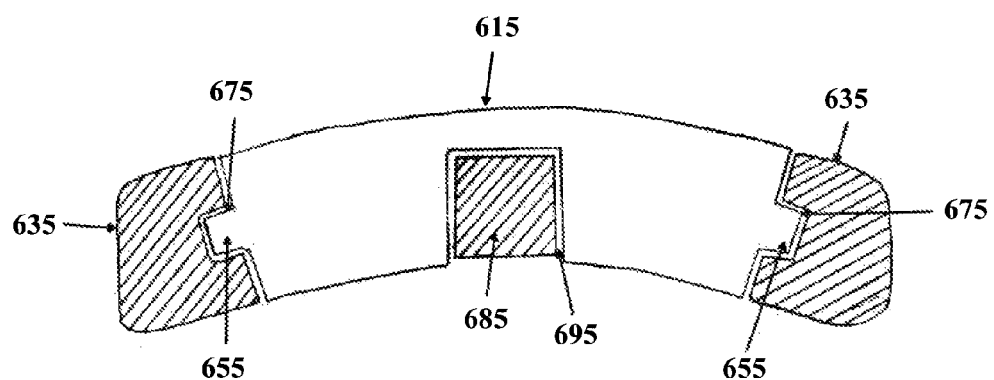
FIG. 6o is a cross-sectional view of another embodiment of the screw plate and the lateral shafts assembly of the dynamic cervical plating system through the screw plate and three lateral shafts, in accordance with an aspect of the present invention.

FIGS. 6a-6o are several different embodiments of the possible screw plate and lateral shaft engagement configurations. For these devices we define the anterior aspect of the figures as the part that is towards the top of the figure and the posterior aspect of the device as towards the bottom part of the figures.

FIG. 6a is a cross-section of one embodiment of the screw plate 601 and the lateral shafts 621 of the dynamic cervical plating system through the screw plate and two lateral shafts. The screw plate has a configured member 641 that fits into a corresponding shaped groove 661 on the inner aspects of the lateral shafts 621.

FIG. 6b is a cross-section view of another embodiment of the screw plate 602 and the lateral shafts 622 of the dynamic cervical plating system through the screw plate and two lateral shafts. The screw plate has a member 642 fits into a correspondingly shaped groove 662 on the inner aspects of the lateral shafts 622.

FIG. 6c is a cross-sectional view of another embodiment of the screw plate 603 and the lateral shafts 623 of the dynamic cervical plating system through the screw plate and two lateral shafts. The screw plate has a member 643 which is arcuately shaped and fits into a correspondingly shaped groove 663 on the inner aspects of the lateral shafts 623.

FIG. 6d is a cross-sectional view of another embodiment of the screw plate 604 and the lateral shafts 624 of the dynamic cervical plating system through the screw plate and two lateral shafts. The screw plate has a member 644 which is configured with a hook-like projection and fits into a correspondingly shaped groove 664 on the inner aspects of the lateral shafts 624 as shown.

FIG. 6e is a cross-sectional view of another embodiment of the screw plate 605 and the lateral shafts 625 and one T-shaped middle shaft 698 of the dynamic cervical plating system through the screw plate and the three shafts. The screw plate has a member 645 which is configured with a hook like projection and fits into a correspondingly shaped groove 665 on the inner aspects of the lateral shafts 625. The screw plate 605 also has a polygonal shaped groove 699 that slidably fits the correspondingly shaped middle shaft 698.

FIG. 6f is a cross-sectional view of another embodiment of the dynamic cervical plating system consisting of the screw plate 606, two lateral shafts 626 and a middle shaft 676. The screw plate 606 has a member 646 that slidingly engages a correspondingly shaped groove 666 on the inner aspects of the lateral shafts 626. The screw plate 606 also has a middle shaft tunnel 686 that slidably fits the middle shaft 676.

FIG. 6g is a cross-sectional view of another embodiment of the dynamic cervical plating system consisting of a screw plate 607, two lateral shafts 627 and middle shaft 677. The screw plate 607 has two members 647 laterally that slidingly engage two corresponding shaped grooves 667 on the inner aspects on the lateral shafts 627. The screw plate 607 also has an intermediate shaft tunnel 687 that slidably fits the correspondingly shaped middle shaft 677.

FIG. 6h is a cross-sectional view of another embodiment of the dynamic cervical plating system consisting of a screw plate 608, two lateral shafts 628 and a middle shaft 678. The screw plate 608 has an angled profile 648 such that the anterior surface may be wider than the posterior surface and also slidably apposes the inner surface 668 of the lateral shaft 628. The middle shaft 678 being polygonally shaped with its smaller edge positioned towards the anterior aspect of the device. The middle shaft 678 slidably fits in a similarly shaped groove in the screw plate 688.

FIG. 6i is a cross-sectional view of another embodiment of the device with the screw plate 609, two lateral shafts 629 and middle shaft 679. The screw plate 609 has an angled profile with members 649 that protrude along the angled lateral surface and fit into correspondingly shaped grooves 669 on the inner aspect on the lateral shafts 629 as shown. The screw plate 609 also has a middle shaft tunnel 689 that slidably engages the middle shaft 679.

FIG. 6j is a cross-sectional view of another embodiment of the dynamic cervical plating system with a screw plate 610, two lateral shafts 630 and a middle shaft 680. The screw plate 610 has an angled profile of its lateral surfaces 650 such that the anterior surface is wider than the posterior surface and this slidably apposes the inner surface 670 of the lateral shaft 630. Also, the middle shaft 680, for example, is in the shape of trapezoid with its smaller edge, being towards the posterior aspect of the device. The middle shaft 680 slidably engages with a similarly shaped groove in the screw plate 690.

FIG. 6k is a cross-sectional view of another embodiment of the dynamic cervical plating system with a screw plate 611, two lateral shafts 631 and a middle shaft 681. The screw plate 611 has a bi-angled shaped profile 651 with the anterior and the posterior edges of the lateral surface protruding and slidably opposing the inner surface 671 of the lateral shaft 631. Also, the middle shaft 681 for example, is in the shape of trapezoid with its smaller edge towards the anterior aspect of the device. The middle shaft 681 slidably fits in a similarly shaped middle shaft tunnel 691 in the screw plate 611.

FIG. 6*l* is a cross-sectional view of another embodiment of the dynamic cervical plating system with a screw plate 612, two lateral shafts 632 and a middle shaft 682. The screw plate 612 has two members 652 along the anterior edge of the lateral surfaces and these slidably appose similarly shaped grooves 672 on the inner surface of the lateral shafts 632. Also, the middle shaft 682 for example, is in the shape of trapezoid, with its smaller edge, positioned on the anterior aspect of the device. The middle shaft 682 may slidably fit into a correspondingly shaped middle shaft tunnel 692 in the screw plate 612.

Figure 6M:
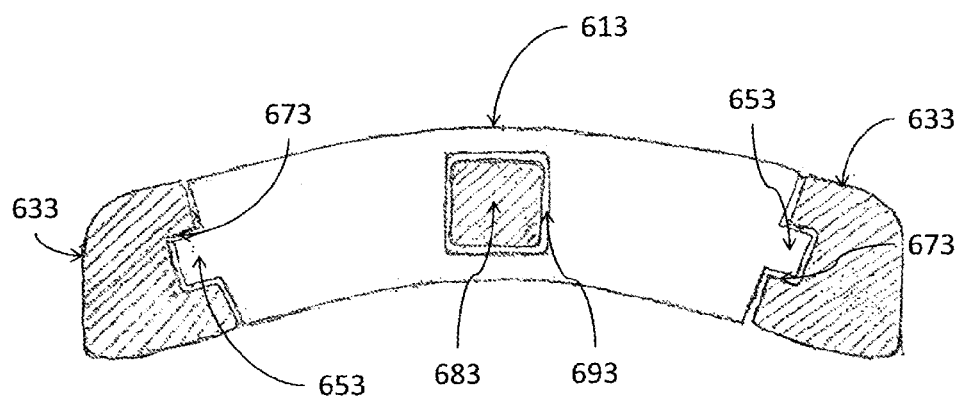
FIG. 6m is a cross-sectional view of another embodiment of the screw plate and the lateral shafts assembly of the dynamic cervical plating system through the screw plate and three lateral shafts, in accordance with an aspect of the present invention.

FIG. 6*m* is a cross-sectional view of another embodiment of the dynamic cervical plating system with a screw plate 613, two lateral shafts 633 and a middle shaft 683. The screw plate 613 has two members 653 along the lateral surface and these slidably engage similarly shaped grooves 673 on the inner surface of the lateral shafts 633. Also, for example, the middle shaft 683 has a rectangular cross section profile. The middle shaft 683 slidably fits in a similarly configured middle shaft tunnel 693 in the screw plate 613.

FIG. 6*n* is a cross-sectional view of another embodiment of the dynamic cervical plating system with a screw plate 614, two lateral shafts 634 and a middle shaft 684. The screw plate 614 has at least one member 654 along the lateral surface which slidably engages a similarly shaped groove 674 on the inner surface of the lateral shaft 634. Also, the middle shaft 684 has a slit 694 along its length. The screw plate 614 has its middle part 697 narrowed in profile to slidably fit into the slit 694 in the middle shaft 684.

FIG. 6*o* is a cross-sectional view of another embodiment of the dynamic cervical plating system with a screw plate 615, two lateral shafts 635 and a middle shaft 685. The screw plate 615 has at least one member 655 along the lateral surface and this slidably engages a similarly shaped groove 675 on the inner surface of the lateral shaft 635. Also, for example, the middle shaft 685 has a rectangular cross section profile. The middle shaft 685 may slidably fit into a similarly shaped middle shaft groove 695 in the screw plate 615.

Figure 7A:
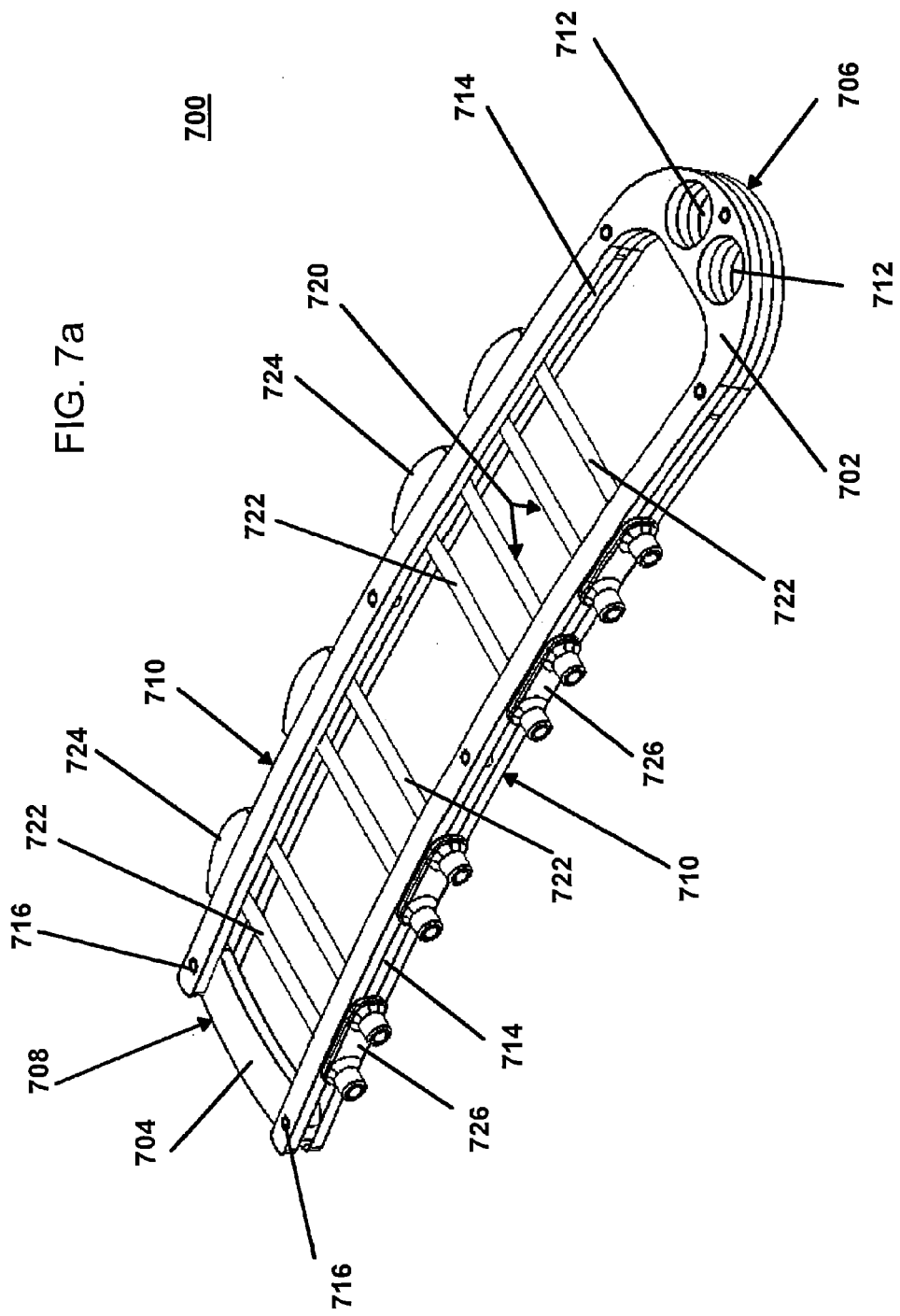
FIG. 7a is another embodiment of the dynamic cervical plating system from a top perspective view, in accordance with an aspect of the present invention.
Figure 7B:
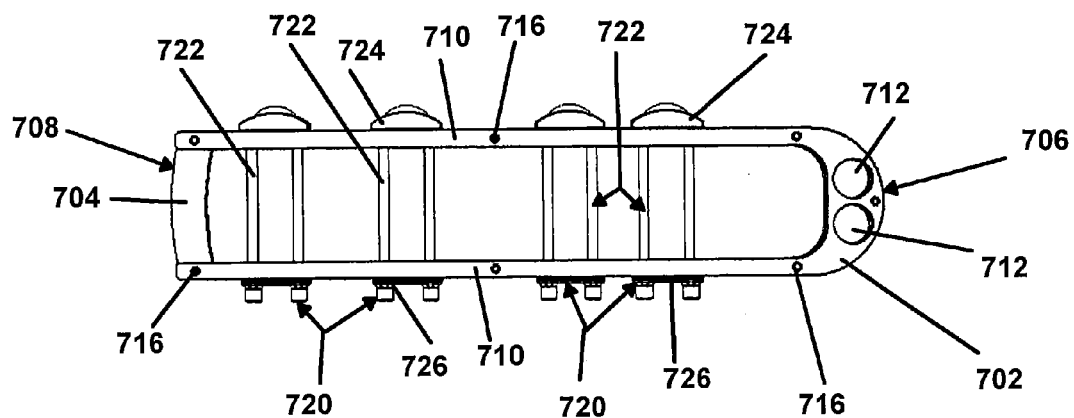
FIG. 7b is a top view of the embodiment of FIG. 7a, in accordance with an aspect of the present invention.
Figure 7C:
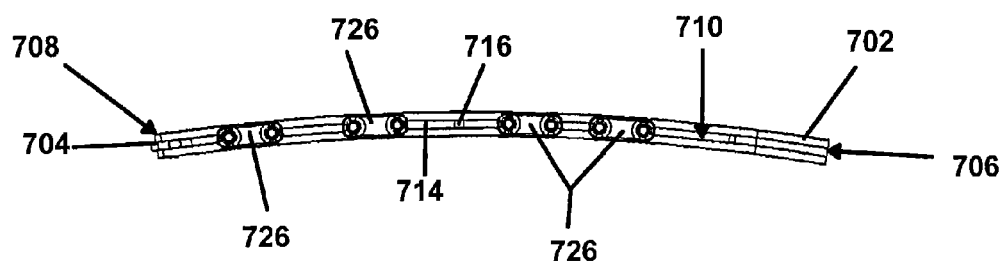
FIG. 7c is a side view of the embodiment of FIG. 7a, in accordance with an aspect of the present invention.
Figure 15A:
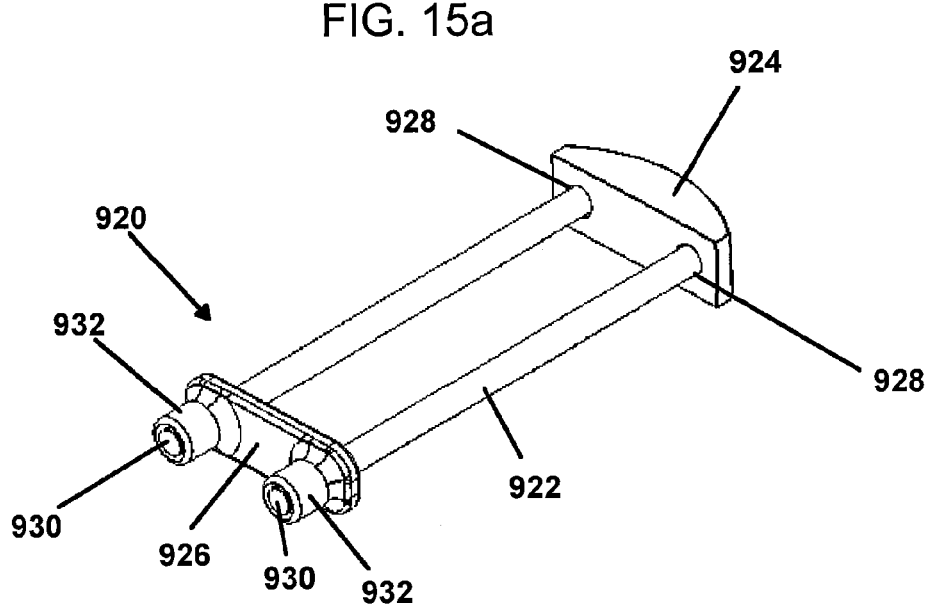
FIG. 15a is a top perspective view of the cable and crimp system of the dynamic cervical plating systems of FIGS. 7a and 14a, in accordance with an aspect of the present invention.
Figure 15B:
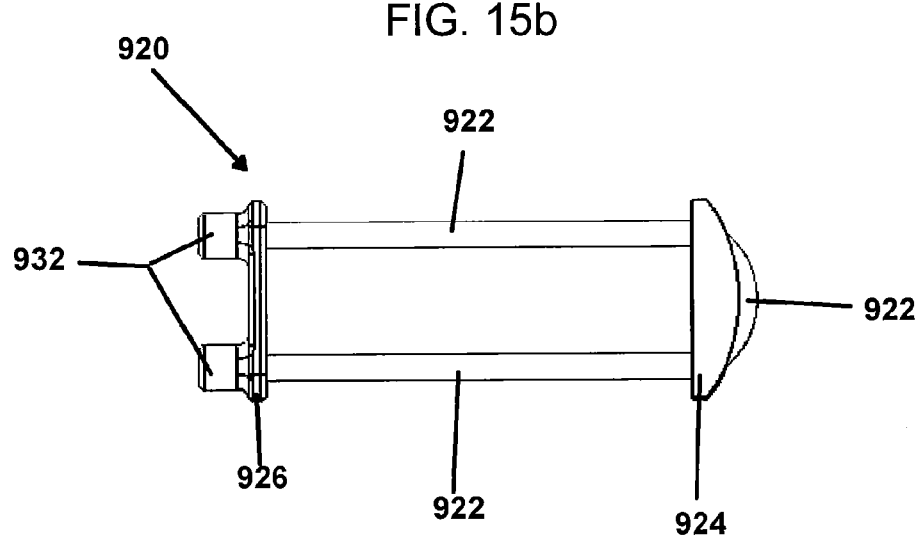
FIG. 15b is a top view of the cable and crimp system of FIG. 15a, in accordance with an aspect of the present invention.
Figure 16A:
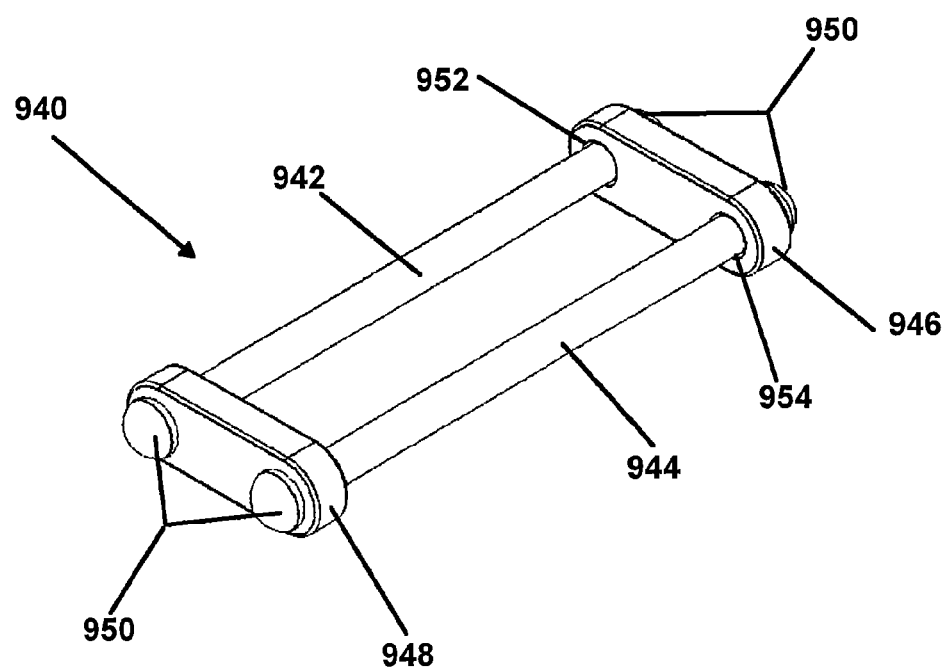
FIG. 16a is a top perspective view of the cable and crimp system of FIGS. 14e and 14f, in accordance with an aspect of the present invention.
Figure 16B:
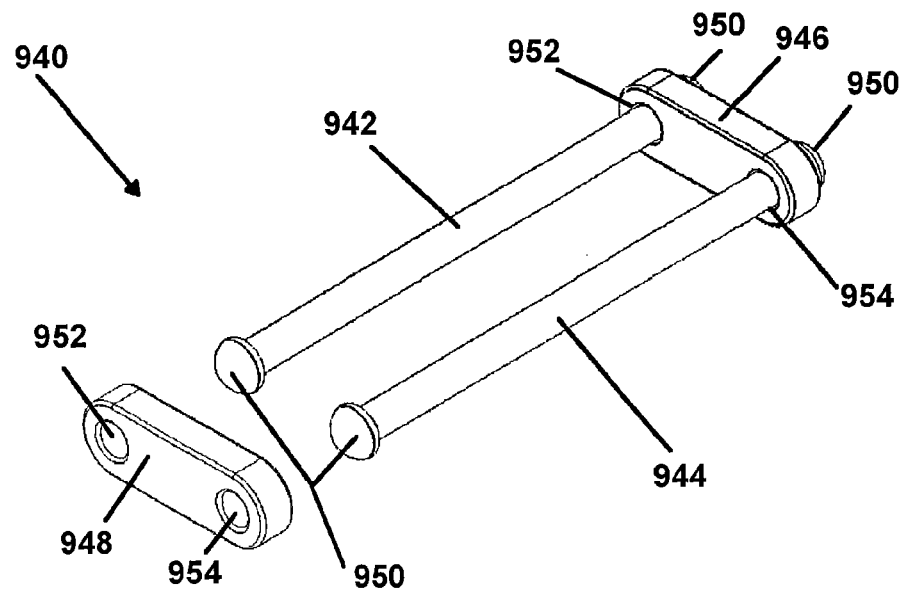
FIG. 16b is a partially exploded top perspective view of the cable and crimp system of FIG. 16a, in accordance with an aspect of the present invention.
Figure 16C:
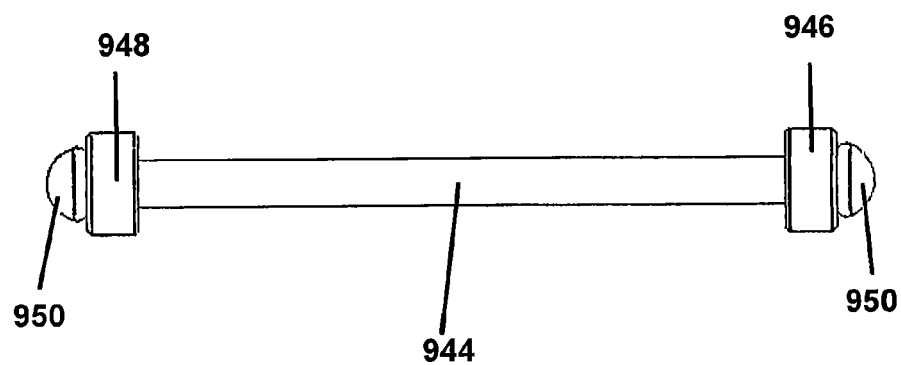
FIG. 16c is a side view of the cable and crimp system of FIG. 16a, in accordance with an aspect of the present invention.
Figure 16D:
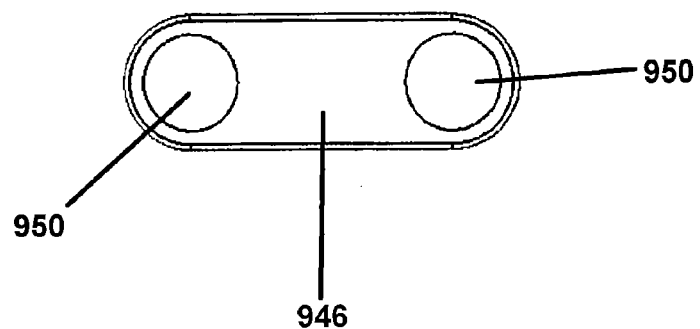
FIG. 16d is a front view of the cable and crimp system of FIG. 16a, in accordance with an aspect of the present invention.

Referring now to FIGS. 7*a*-7*d*, another embodiment of a dynamic cervical plating system 700 is shown. The dynamic cervical plating system 700 including a head plate 702, an end plate 704, and at least one attachment cable system 720. As best seen in FIG. 7*c*, the dynamic cervical plating system 700 is curved to mimic the lordotic curve of the spinal column. The head plate 702 has a proximal end 706 with two proximal end screw holes 712, a distal end 708, and two lateral shafts 710 that enable attachment of the end plate 704 at the distal end of the head plate 702 using fasteners 716. If the head plate 702 is comprised of multiple pieces rather than a single piece, additional fasteners 716 may be used to attach the pieces of the head plate 702. The fasteners 716 may be pins, screws, or the like. There is also a slot 714 along each of the lateral shafts 710. In the depicted embodiment there are four attachment cable systems 720. The attachment cable systems 720 mate with the slots 714 in the lateral shafts 710 allowing the attachment cable systems 720 to slide in a proximal-distal direction while allowing for limited lateral sliding movement. The attachment cable systems 720 having a cable 722, a first crimp 724, and a second crimp 726, as best depicted in FIGS. 15*a*-15*b*.

Figure 7D:
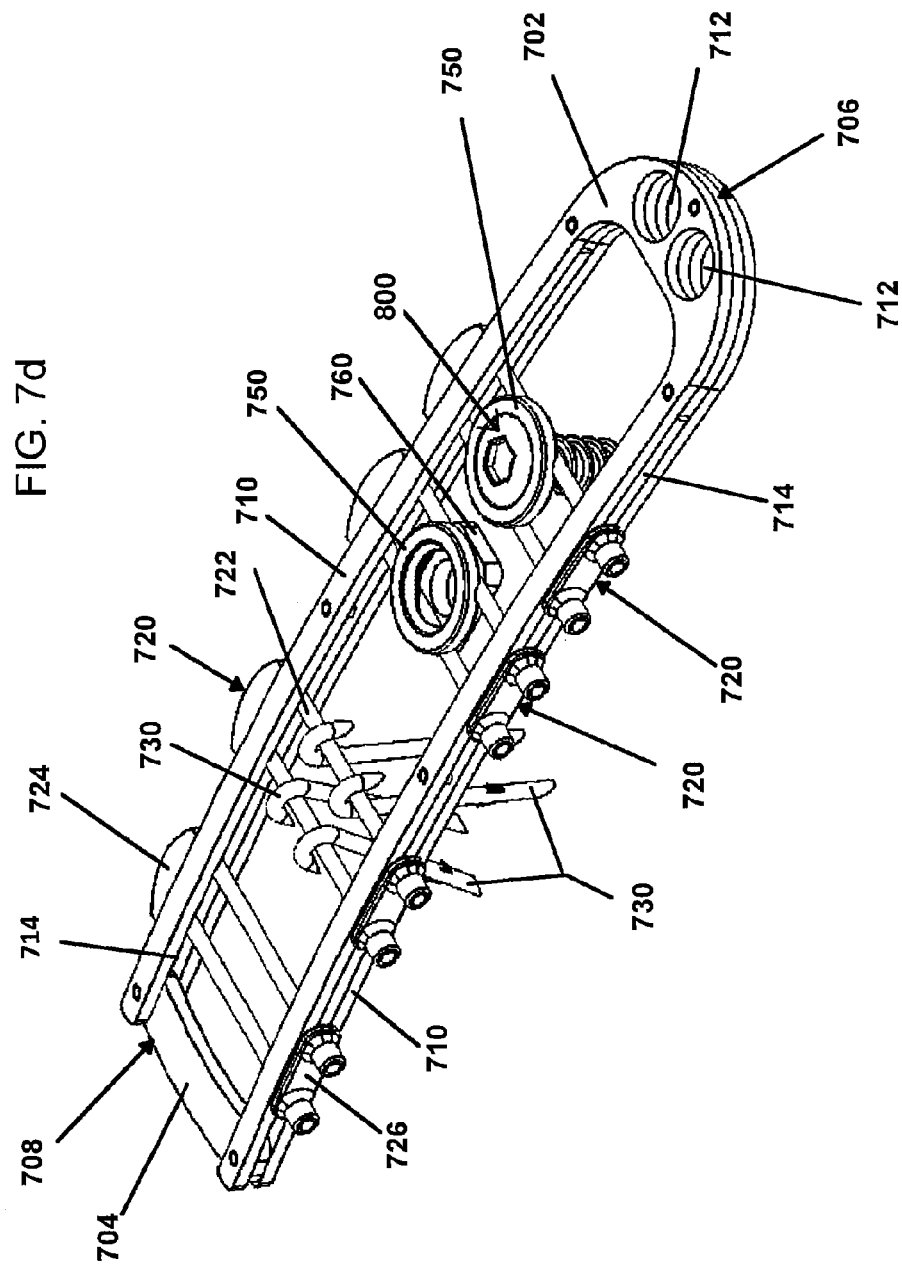
FIG. 7d is a top perspective view of the embodiment of FIG. 7a including three types of fasteners, in accordance with an aspect of the present invention.
Figure 9A:
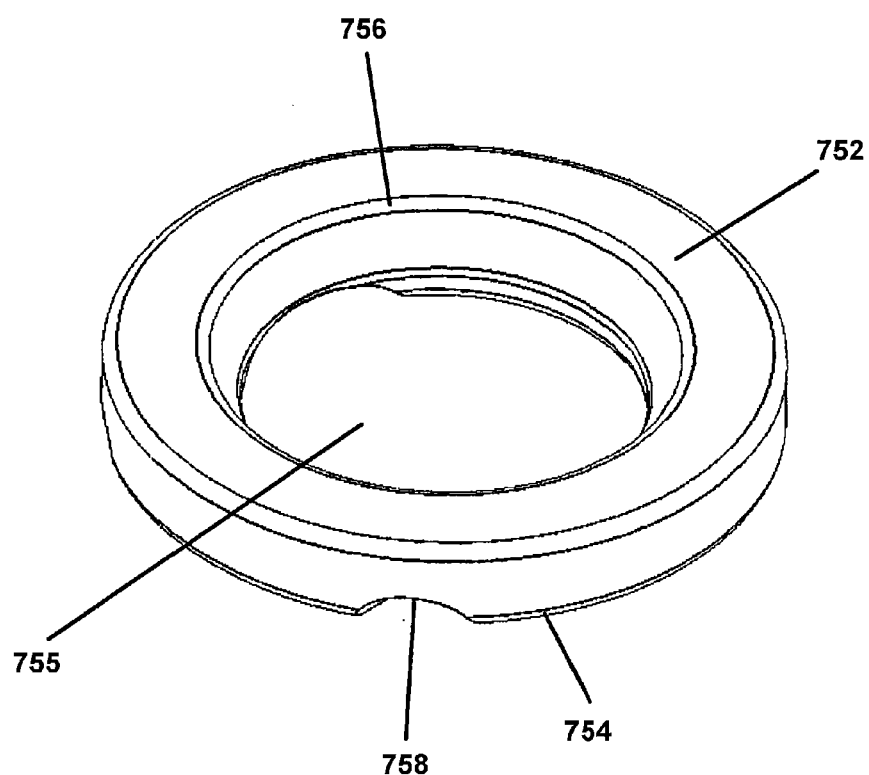
FIG. 9a is a top perspective view of a fastener seat of another one of the fastener embodiments of FIG. 7d, in accordance with an aspect of the present invention.

As illustrated in FIG. 7*d*, a number of different fasteners, including nails 730 and screws 800, may be used to secure the dynamic cervical plating system 700 to the vertebrae. The screws 800 may be used with various screw seats such as a first screw seat 750 and/or a second screw seat 760. The nails 730 as depicted in FIG. 8*a* include a head 732 which may be curved to allow the nails 730 to grasp the cables 722, the head 732 including a point 736 at a first end and a shank 734 at the second end. The shank 734 ending in a point 738 and including at least one barb 739. The nails 730 have two barbs 739 in the depicted embodiments. The points 736 and 738 provide a sharp edge to aid in inserting the nails 730 into a patient's vertebrae. The at least one barb 739 assists in preventing the nails 730 from backing out of the patient's vertebrae after surgery. Depicted in FIG. 8*b* is an alternative nail 780 which may be used in place of nails 730. The nail 780 including a head 782 which may be curved to allow the nails 780 to grasp the cables 722. The head 782 may include a point 784 at a first end and a shank 786 at the second end. The shank 786 ending in a point 788 and including at least one barb 790. In the depicted embodiment the nail has two barbs 790 that are on opposite sides of the shank 786 and offset from each other. The points 784 and 788 provide a sharp edge to aid in inserting the nails 780 into the patient's vertebrae. The at least one barb 790 grasps the patient's vertebra and prevents the nails 780 from backing out of the vertebra after surgery.

Referring now to FIGS. 9*a*-11*b* and with continued reference to FIG. 7*d*, the first screw seat 750 and/or the second screw seat 760 are shown. The first screw seat 750, depicted in FIGS. 9*a*-9*c*, has a generally round shape with a first side 752, a second side 754, and a center screw hole 755. The first side 752 includes a groove 756 to provide a stop for a screw, such as screw 800, as it is inserted into the patient's vertebrae. The second side 754 includes two parallel grooves 758 that mate with the cable 722. The first screw seat 750 provides support for the screw 800 when the dynamic cervical plating system 700 is secured to the vertebrae. The second screw seat 760 may optionally be used with the first screw seat 750 to support a screw, such as screw 800. As depicted in FIGS. 10*a*-10*b*, the second screw seat 760 has a generally rectangular shape with a first side 762, a second side 764, and a center screw hole 765. The first side 762 includes two parallel grooves 768 that correspond with the cable 722.

During a surgery, the second screw seat 760 would be inserted below the cable 722 of the attachment cable system 720 and the second side 764 of the second screw seat 760 would align with the cable 722. Then the first screw seat 750 is placed over the second screw seat 760 and the two parallel grooves 768 of the first screw seat 750 are aligned with the cable 722. A screw, such as screw 800, would then be inserted through screw hole 755 in the first screw seat 750 and screw hole 765 in the second screw seat 760. The screw 800 would be screwed into the patient's vertebra thereby clamping the cable 722 between the first screw seat 750 and the second screw seat 760.

Figure 11A:
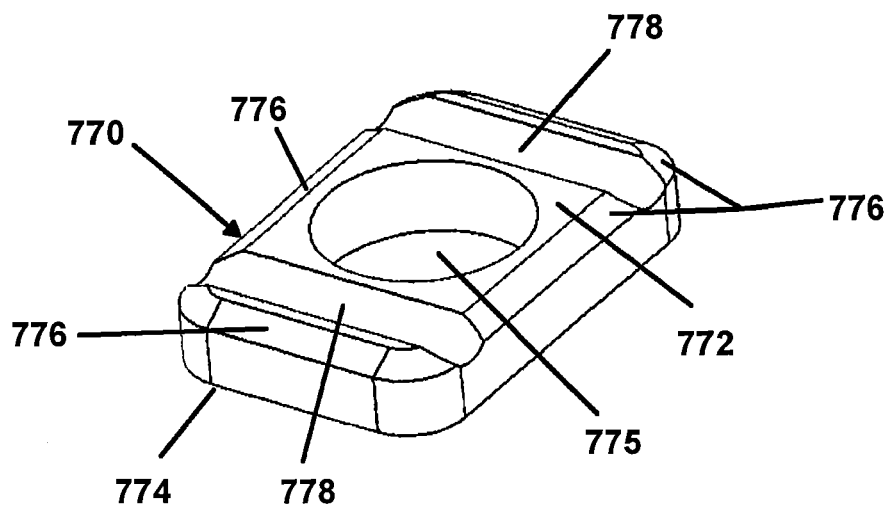
FIG. 11a is a top perspective view of another embodiment fastener seat of another one of the fastener embodiments of FIG. 7d, in accordance with an aspect of the present invention.
Figure 11B:
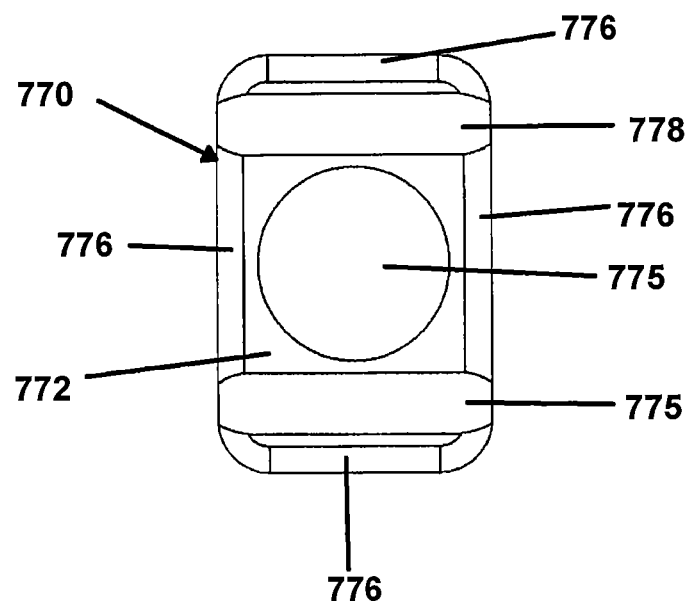
FIG. 11b is a top view of the fastener seat of FIG. 11a, in accordance with an aspect of the present invention.

An alternative to the second screw seat 760 is the third screw seat 770 depicted in FIGS. 11*a*-11*b*. The third screw seat 770 has a generally rectangular shape with a first side 772, a second side 774, and a center screw hole 775. The first side 772 of the third screw seat 770 has angled edges 776. The first side 772 also includes two parallel grooves 778 that correspond with the cable 722. During an anterior cervical discectomy and fusion or a similar procedure the third screw seat 770 may be inserted below the cable 722 of the attachment cable system 720 and the second side 774 of the third screw seat 770 would align with the cable 722. Then the first screw seat 750 may be placed over the third screw seat 770 and the two parallel grooves 778 of the first screw seat 750 are aligned with the cable 722. A screw, such as screw 800, may be inserted through the screw hole 755 in the first screw seat and the screw hole 775 in the third screw seat 760. The screw 800 may then be screwed into the patient's vertebra clamping the cable 722 between the first screw seat 750 and the third screw seat 770.

Figure 12A:
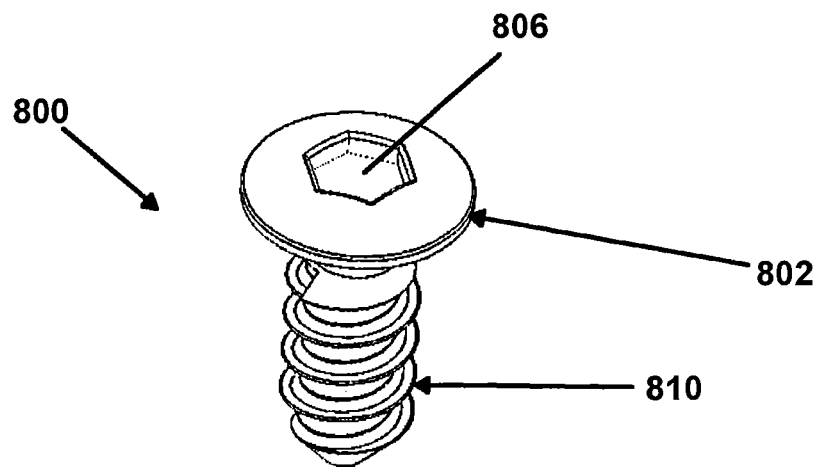
FIG. 12a is a top perspective view of a fastener of FIG. 7d, in accordance with an aspect of the present invention.
Figure 12B:
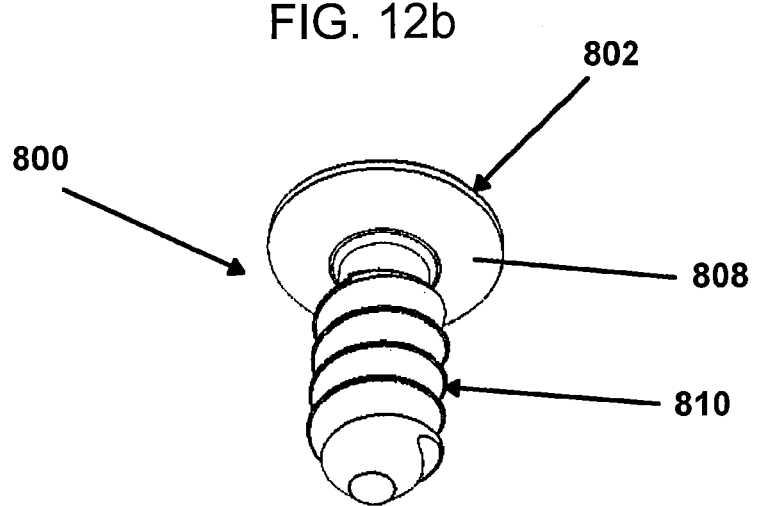
FIG. 12b is a bottom perspective view of the fastener of FIG. 12a, in accordance with an aspect of the present invention.
Figure 13:
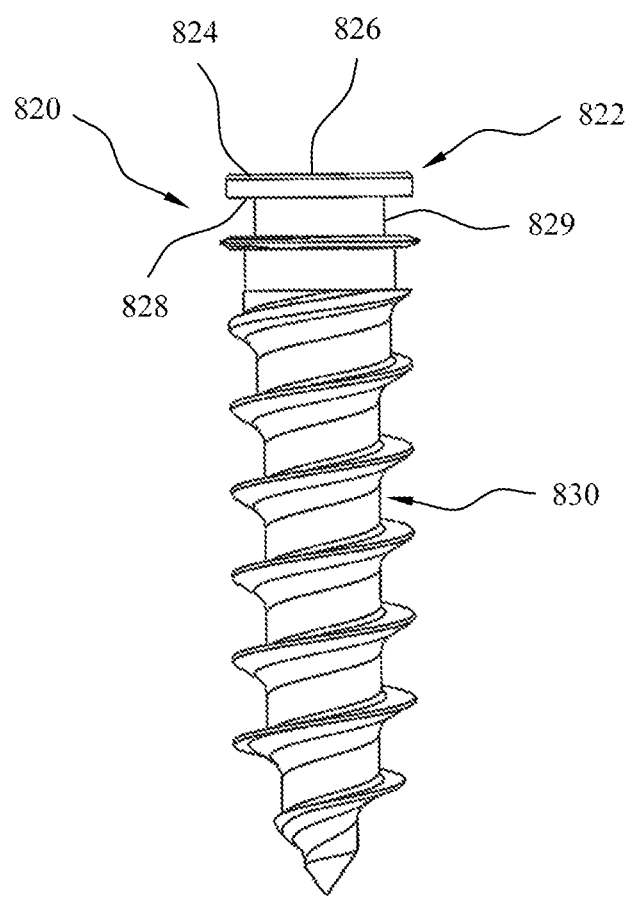
FIG. 13 is a top perspective view of another embodiment fastener, in accordance with an aspect of the present invention.

Referring now to FIGS. 12a-12b, a first screw 800 is shown. The first screw 800 including a head 802 and a threaded end 810. The head 802 including an upper surface 804 with an opening 806 and a lower surface 808. The lower surface 808 of the first screw 800 may sit within the groove 756 of the first screw seat 750. A second screw 820, as seen in FIG. 13, may alternatively be used to secure a dynamic cervical plating system 700 to a patient's vertebra without a screw seat, such as the first screw seat 750, second screw seat 760, or third screw seat 770. The second screw 820 includes a head 822 and a threaded end 830. The head 822 including an upper surface 824 with an opening 826 and a lower surface 828. The lower surface 828 of the first screw including a groove 829 above the threaded end 830. The groove 829 in the screw 820 provides a channel for the cable 722 when the screw 820 is inserted into the patient's vertebra between the cables 722 of an attachment cable system 720.

Figure 14A:
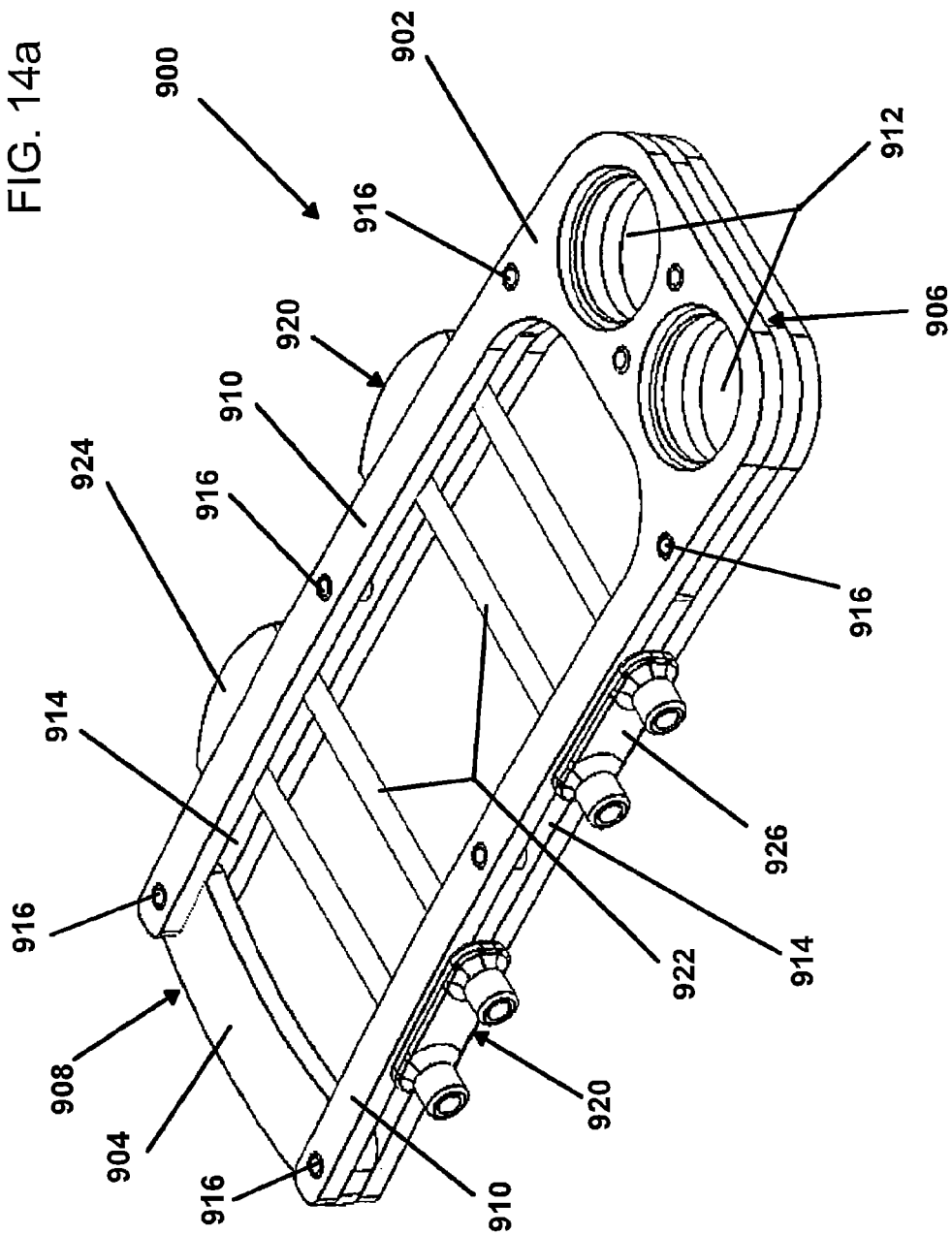
FIG. 14a is another embodiment of a dynamic cervical plating system from a top perspective view, in accordance with an aspect of the present invention.
Figure 14C:
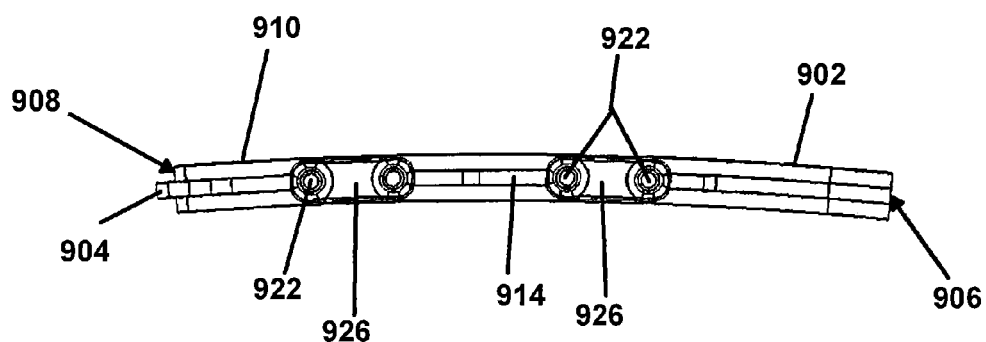
FIG. 14c is a first side view of the plating system of FIG. 14a, in accordance with an aspect of the present invention.
Figure 14D:
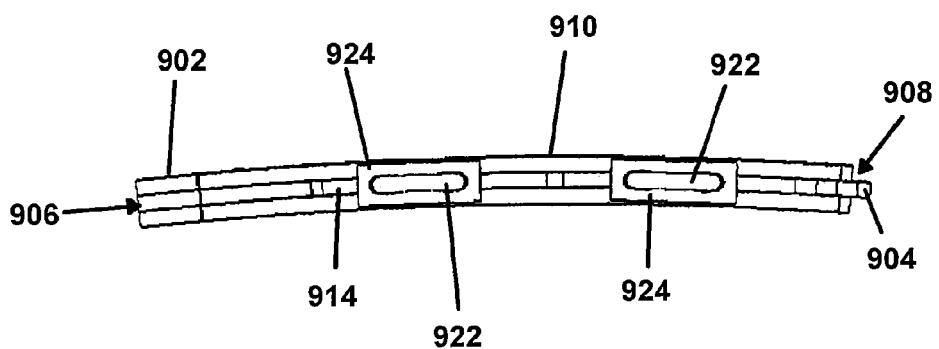
FIG. 14d is a second side view of the plating system of FIG. 14a, in accordance with an aspect of the present invention.

Another dynamic cervical plating system 900 is shown in FIGS. 14a-14f. As best seen in FIGS. 14c and 14d, the dynamic cervical plating system 900 is curved to mimic the lordotic curve of the spinal column. The dynamic cervical plating system 900 includes a head plate 902, an end plate 904, and at least one first attachment cable system 920. The head plate 902 has a proximal end 906 with two proximal end screw holes 912, a distal end 908, and two lateral shafts 910 that enable attachment of the end plate 904 at the distal end of the head plate 902 using fasteners 916. If the head plate 902 is not a single piece, additional fasteners 916 may be used to attach the pieces of the head plate 902. The fasteners 916 may be pins, screws, or the like. There is also a slot 914 along each of the lateral shafts 910. In the depicted embodiment there are two first attachment cable systems 920. The first attachment cable systems 920 mate with the slots 914 in the lateral shafts 910 allowing the first attachment cable systems 920 to slide in a proximal-distal direction while allowing for limited lateral sliding movement. The first attachment cable systems 920 having a cable 922, a first crimp 924, and a second crimp 926, as best seen in FIGS. 15a-15b and described in greater detail below.

Figure 14E:
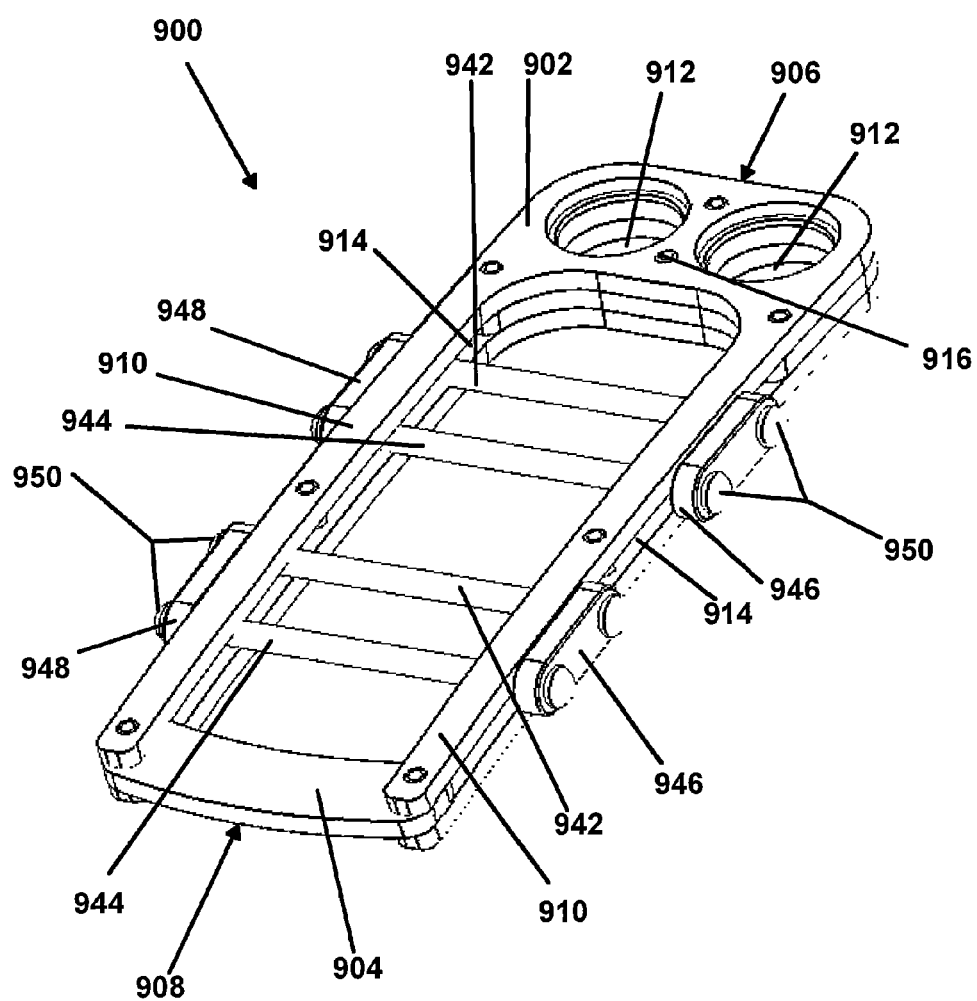
FIG. 14e is a top perspective view of the plating system of FIG. 14a with alternative attachment cable systems, in accordance with an aspect of the present invention.
Figure 14F:
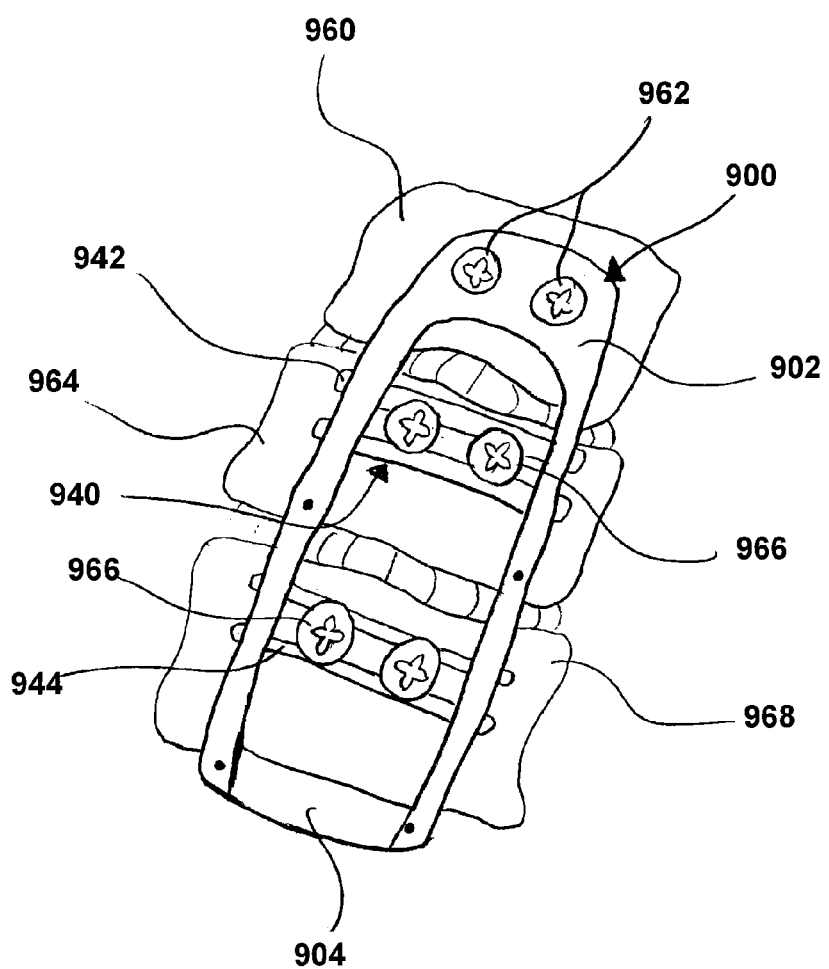
FIG. 14f is a top view of the plating system of FIG. 14e secured to a patient's spine, in accordance with an aspect of the present invention.

Depicted in FIGS. 14e and 14f is the dynamic cervical plating system 900 including a second attachment cable system 940 that is attached to three vertebrae of a patient in FIG. 14f. The dynamic cervical plating system 900 includes the head plate 902, the end plate 904, and at least one second attachment cable system 940. The second attachment cable system 940 is an alternative to the first attachment cable system 920. In the depicted embodiment there are two second attachment cable systems 940. The second attachment cable system 940 having a first cable 942, a second cable 944, a first crimp 946, and a second crimp 948, as best seen in FIGS. 16a-16d and described in greater detail below. During an anterior cervical discectomy and fusion or similar procedure, once the damaged disc has been removed and an interbody spacer has been inserted, the dynamic cervical plating system 900 may then be fastened to the patient's vertebrae. As depicted in FIG. 14f, the plating system 900 may be aligned along the spinal column and secured to a first vertebra 960 through screw holes 912 using fasteners 962. The first vertebra 960 may be, for example, the C3 vertebra. Then a first second attachment cable system 940 may be aligned and secured to a second vertebra 964. The second attachment cable system 940 may be secured to the second vertebra 964 using at least one fastener 966. In the depicted embodiment there are two fasteners 966 securing the cable system 940 to the second vertebra 964 and the at least one fastener 966 may be a screw of the type depicted in FIG. 13. The second vertebra 964 may be, for example, the C4 vertebra. Next another second attachment cable system 940 may be aligned and secured to a third vertebra 968 using at least one fastener 966. In the depicted embodiment two fasteners 966 are used to secure the cable system 940 to the third vertebra 968 and the fasteners 966 may be screws of the type depicted in FIG. 13. The fasteners 966 are inserted between the first and second cables 942 and 944, respectively, and screwed into the second and third vertebrae 964 and 968, respectively. The third vertebra 968 may be, for example, the C5 vertebra.

As discussed above with respect to FIG. 13, the fasteners 966 may be screws including a groove for the first and second cables 942 and 944, respectively, to be secured in when the plating system 900 is secured to the patient's vertebrae. It is also contemplated that the plating system 900 may be secured to a patient's vertebrae in different orders than the one described above, such as attaching the plating system 900 to the first vertebra 960, then attaching a second attachment cable system 940 to the third vertebra 968, and finally attaching a second attachment cable system 940 to the second vertebra 964. Once the plating system 900 is secured to the patient's vertebrae the patient's incision may be closed. The dynamic cervical plating system 900 will provide a degree of movement in the superior-inferior direction providing for a minimal change in length as the patient moves. In addition, as the vertebral body height decreases over time, the dynamic cervical plating system 900 is able to adjust its height to accommodate the vertebral body changes.

Referring now to FIGS. 15a-15b, the first attachment cable system 920 having a cable 922, a first crimp 924, and a second crimp 926 is depicted. The first crimp 924 including two openings 928 for the cable 922 to pass through. The first crimp 924 also having a generally flat surface opposite the second crimp 926 and a generally arced surface to allow the cable 922 to wrap around the outer surface of the first crimp 924. The second crimp 926 including two openings 930 for the ends of cable 922 to pass through. The second crimp 926 also having a generally flat surface opposite the first crimp 924 and two crimping mechanisms 932 for securing the ends of cable 922 in the openings 930. In use, the generally flat surfaces of the first and second crimps 924 and 926, respectively, are aligned with the outer surface of each of the lateral shafts 910 of the plating system 900. When the first attachment cable system 920 is inserted into the head plate 902 the cable 922 becomes taut and is able to support a fastener or a fastener and at least one screw seat.

Figure 17A:
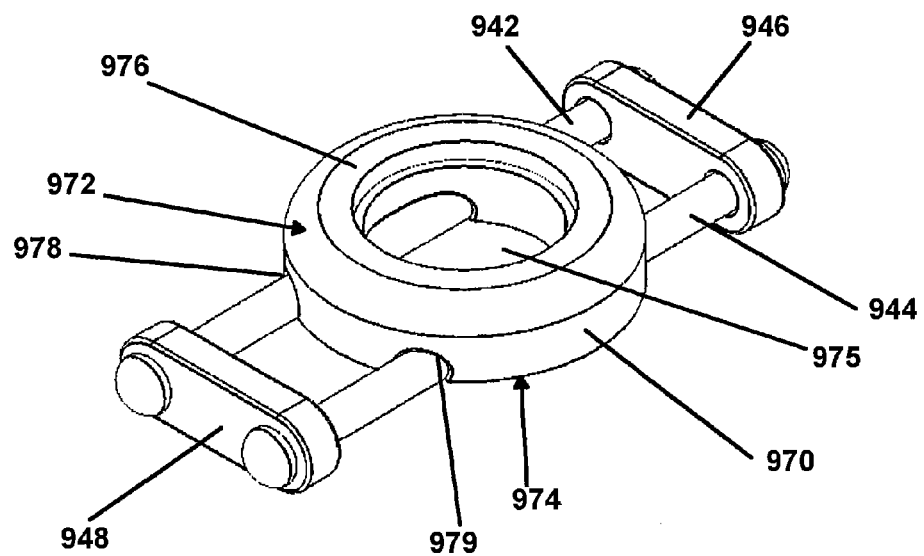
FIG. 17a is a top perspective view of the cable and crimp system of FIG. 16a including a fastener seat, in accordance with an aspect of the present invention.
Figure 17B:
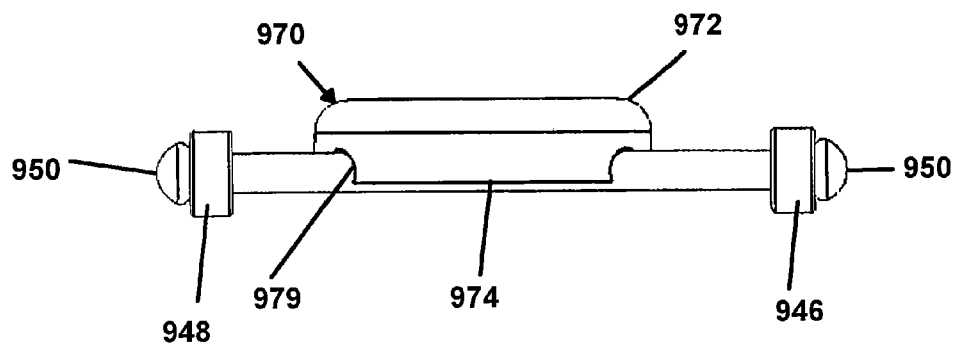
FIG. 17b is a side view of the cable and crimp system and fastener seat of FIG. 17a, in accordance with an aspect of the present invention.
Figure 17C:
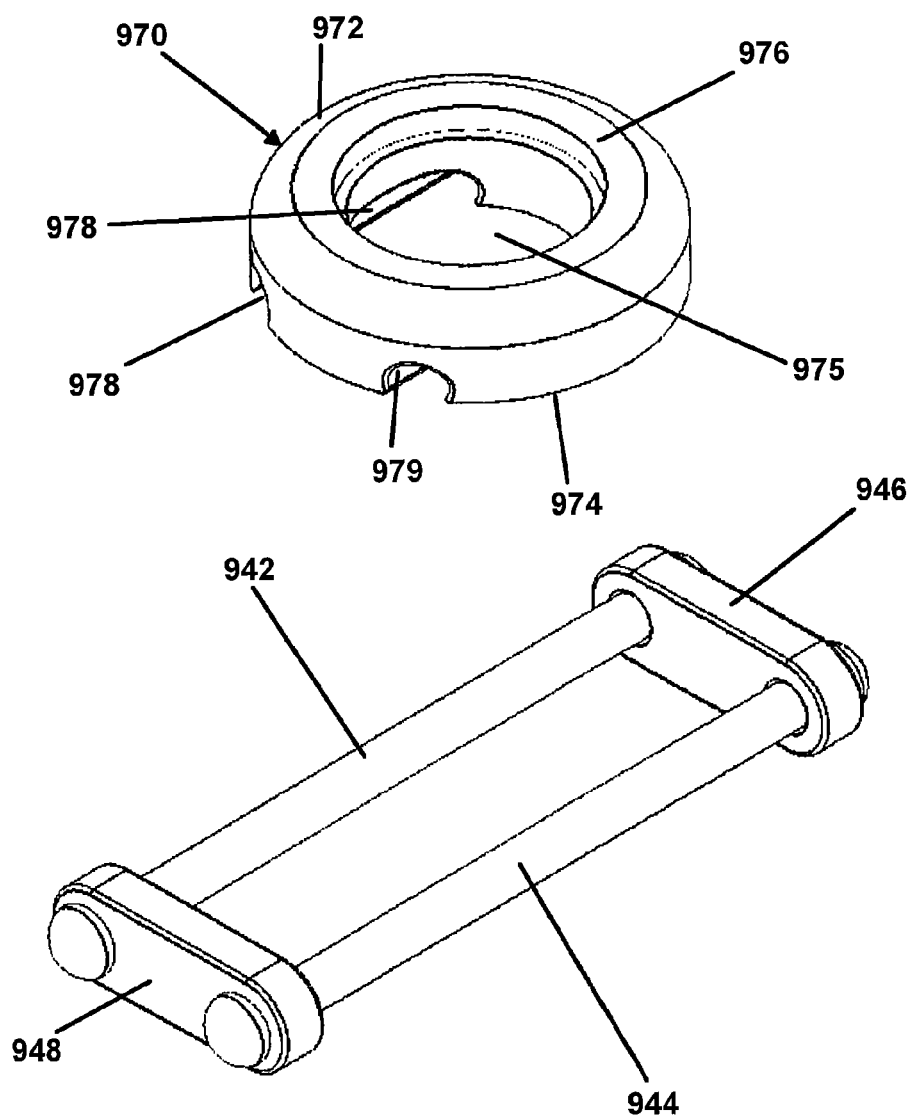
FIG. 17c is an exploded view of the cable and crimp system and fastener seat of FIG. 17a, in accordance with an aspect of the present invention.

Depicted in FIGS. 16a-16d is the second attachment cable system 940. The first crimp 946 and second crimp 948 of the second attachment cable system 940 each including a first opening 952 for the first cable 942 to pass through and a second opening 954 for the second cable 944 to pass through. The first cable 942 and second cable 944 each have two ends 950 that, as depicted, may be larger in diameter than the first cable 942 and second cable 944 as well as the first openings 952 and second openings 954 of the first and second crimps 946 and 948, respectively. The two ends 950 of each of the cables hold the first and second cables 942 and 944, respectively, in place within the second attachment cable systems 940. In use the inner edges of the first and second crimps 946 and 948, respectively, are aligned with the outer surface of each of the lateral shafts 910 of the plating system 900. When the second attachment cable system 940 is inserted into the head plate 902 the first cable 942 and the second cable 944 become taut and are able to support a fastener or a fastener and at least one screw seat, such as screw seat 970 depicted in FIGS. 17a-17c. The screw seat 970 as shown in FIGS. 12a-12c, has a generally round shape with a first side 972, a second side 974, and a screw hole 975. The first side 972 includes a groove 976 to provide a stop for a screw, such as screw 800, as it is inserted into a patient's vertebra. The second side 974 includes two parallel grooves 978 and 979 that mate with the first cable 942 and second cable 944, respectively. The first screw seat 970 provides support for the screw 800 when the dynamic cervical plating system 900 is secured to the vertebrae. A second screw seat, such as screw seat 760, may optionally be used with the first screw seat 970 to support a screw, such as screw 800.

Figure 18A:
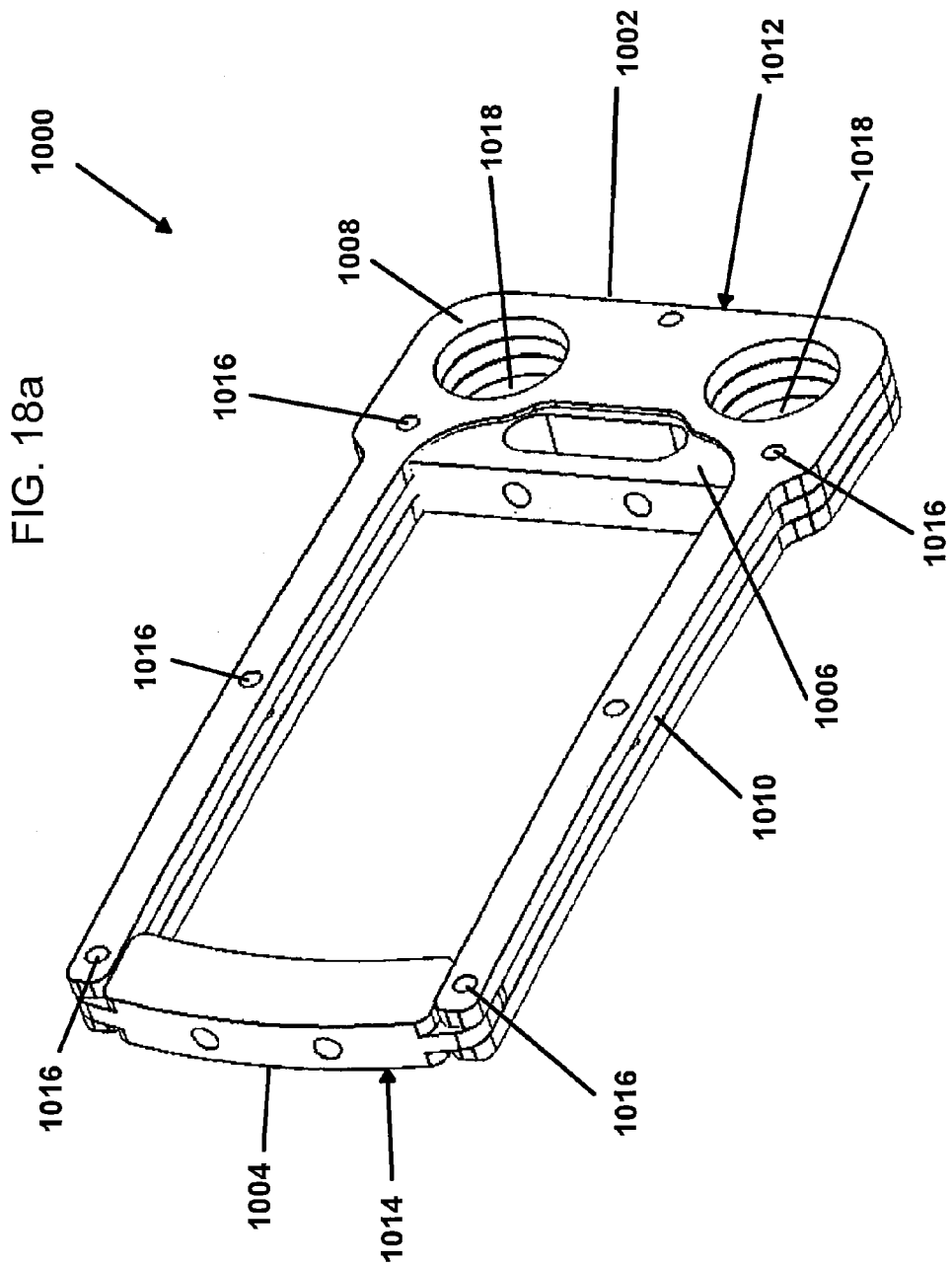
FIG. 18a is a top perspective view of another embodiment of a dynamic cervical plating system, in accordance with an aspect of the present invention.
Figure 18B:
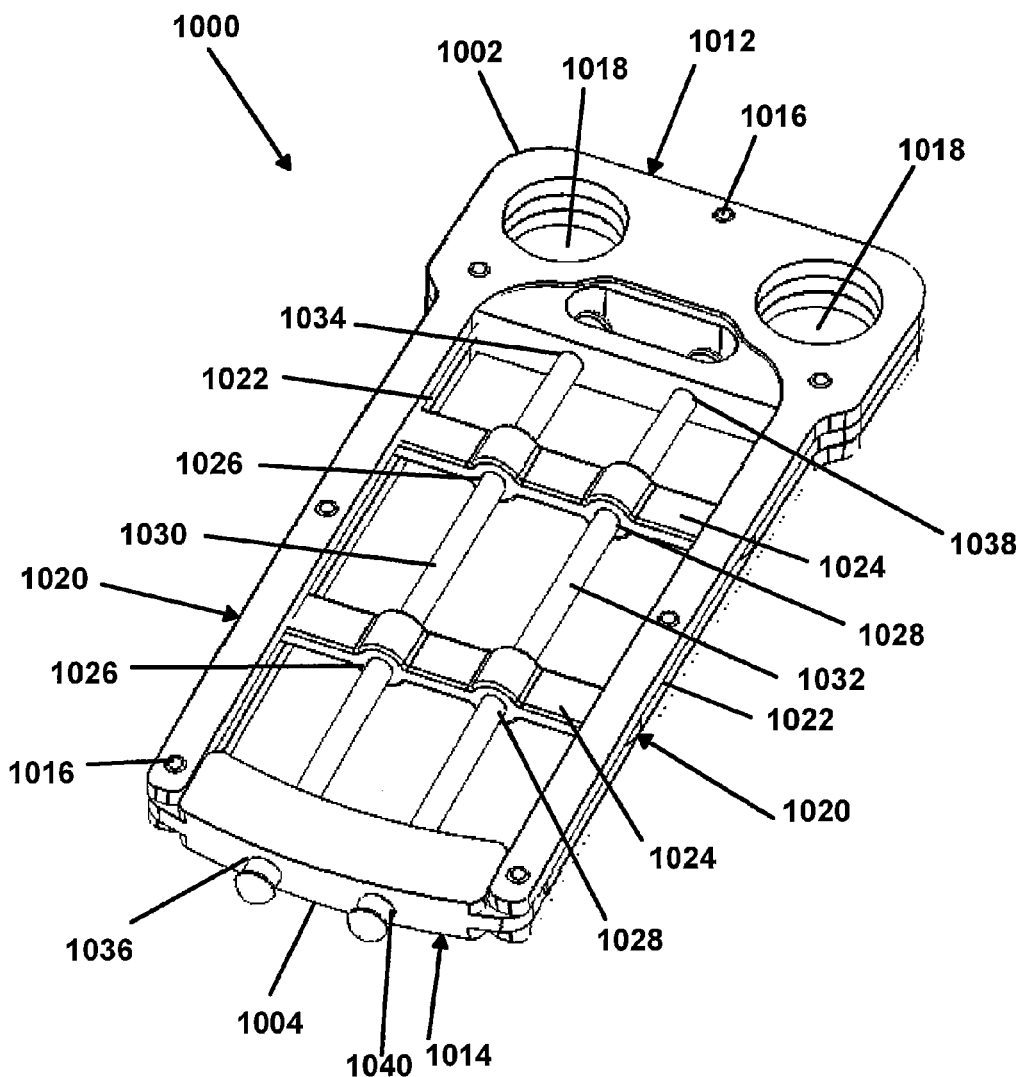
FIG. 18b is a top perspective view of the embodiment of FIG. 18a including two stabilizers, in accordance with an aspect of the present invention.

A dynamic vertical cervical plating system 1000 is depicted in FIGS. 18a-18d. As best seen in FIG. 18c, the dynamic cervical plating system 1000 is curved to mimic the lordotic curve of the spinal column. The dynamic vertical cervical plating system 1000 including a head plate 1002 and an end plate 1004. The head plate 1002 including a base 1006, a first plate 1008, and a second plate 1010. The base 1006 being secured between the first plate 1008 and the second plate 1010 at the proximal end 1012 with fasteners 1016. The base 1006, first plate 1008, and second plate 1010 each include at least one opening which align to create at least one screw hole 1018 in the head plate 1002. In the depicted embodiment the head plate 1002 includes two screw holes 1018. The end plate 1004 being secured at the distal end 1014 between the first plate 1008 and the second plate 1010 of the head plate 1002 with fasteners 1016. The fasteners 1016 may be pins, screws, or the like. The first and second plates 1008 and 1010 of the head plate 1002 create two lateral shafts 1020 between the proximal end 1012 and the distal end 1014 of the plating system 1000. The space between the first plate 1008 and the second plate 1010 creates a slot 1022 along each of the lateral shafts 1020. The ends of at least one stabilizer plate 1024 slidingly engage the slot 1022 allowing for stabilizer plate 1024 to slide along the slot 1022 of the lateral shafts 1020.

Figure 19A:
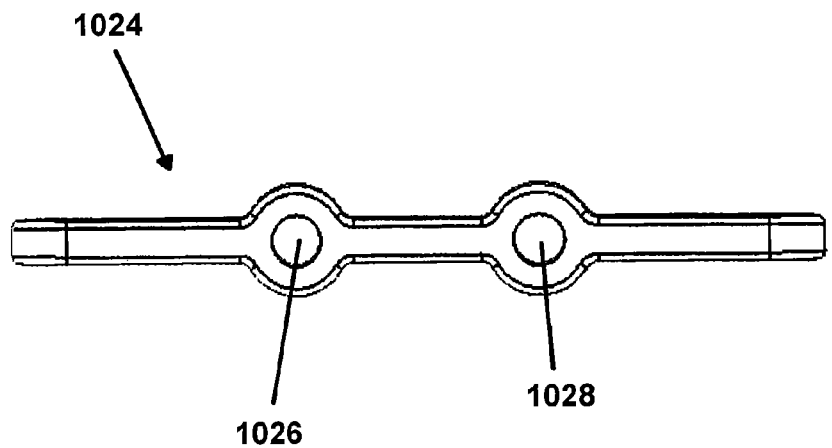
FIG. 19a is a side view of one of the stabilizers of FIG. 18b, in accordance with an aspect of the present invention.
Figure 19B:
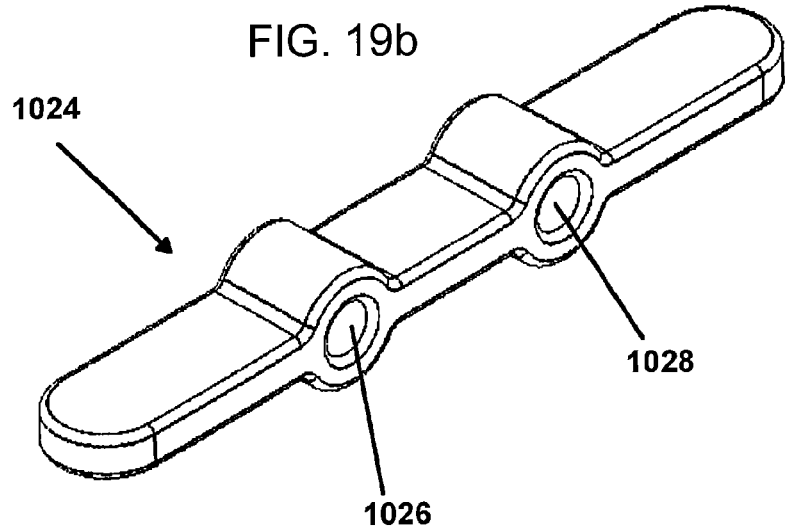
FIG. 19b is a perspective view of the stabilizer of FIG. 19a, in accordance with an aspect of the present invention.

In the depicted embodiment of FIGS. 18a-18d there are two stabilizer plates 1024. As best illustrated in FIGS. 19a-19b, the stabilizer plates 1024 including a first opening 1026 and a second opening 1028 for mating with a first cable 1030 and a second cable 1032. The first cable 1030 may pass through a first opening 1034 in the base 1006, through the first opening 1026 of the stabilizer plates 1024, and finally through a first opening 1036 in the end plate 1004. Similarly, the second cable 1032 may pass through a second opening 1038 in the base 1006, through the second opening 1028 of the stabilizer plates 1024, and finally through a second opening 1040 in the end plate 1004. A fastener, not shown, such as screw 820 depicted in FIG. 13 may be inserted between the first cable 1030 and the second cable 1032 to secure the plating system 1000 to a second vertebra after the plating system 1000 has been secured to a first vertebra superior to the second vertebra. The plating system 1000 is secured to a patient's vertebra using fasteners, not shown, which are inserted through screw holes 1018 and into the patient's vertebra.

Figure 20A:
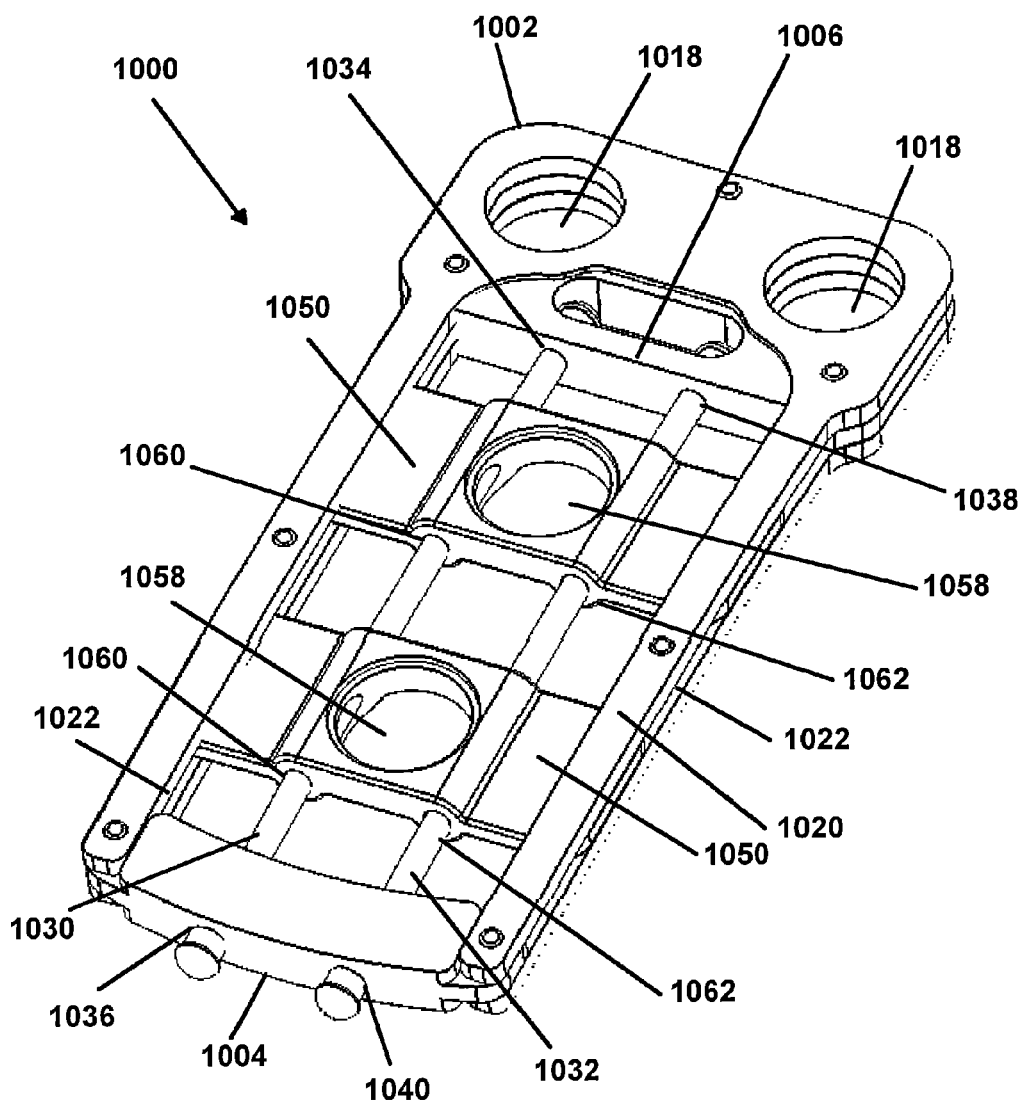
FIG. 20a is a top perspective view of the embodiment of FIG. 18a including two single screw stabilizers, in accordance with an aspect of the present invention.
Figure 21A:
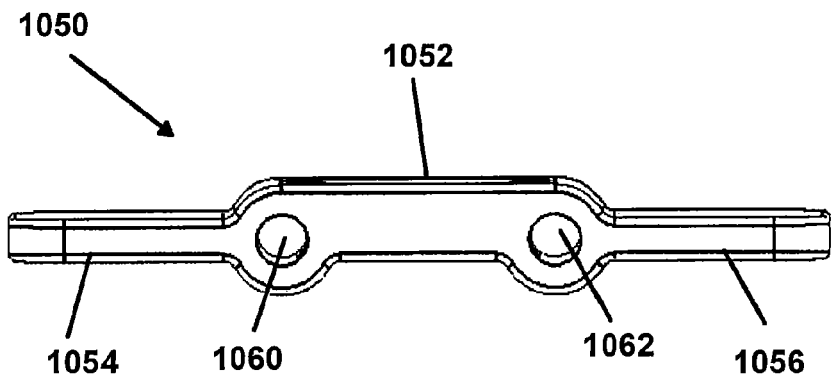
FIG. 21a is a side view of one of the single screw stabilizers of FIG. 20a, in accordance with an aspect of the present invention.
Figure 21B:
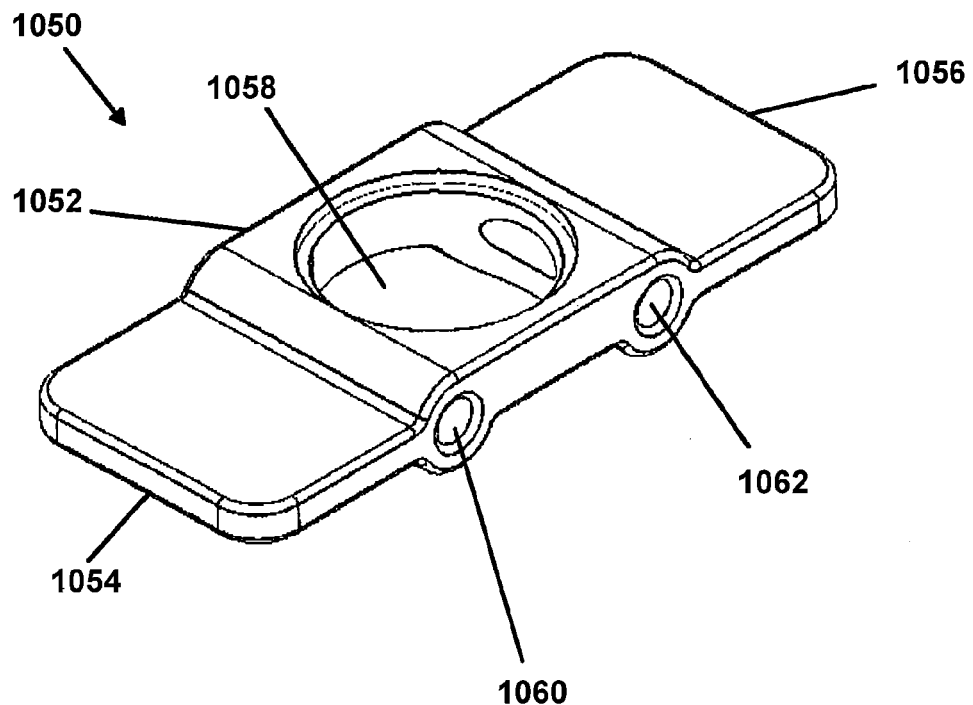
FIG. 21b is a perspective view of the single screw stabilizer of FIG. 21a, in accordance with an aspect of the present invention.

Referring now to FIGS. 20a-20c, the plating system 1000 includes alternative stabilizer plates 1050 is shown. As best seen in FIG. 20b, the dynamic cervical plating system 1000 is curved to mimic the lordotic curve of the spinal column. As best illustrated in FIGS. 21a-21b, the stabilizer plates 1050 include a center base 1052 with a first tab 1054 and a second tab 1056. The center base 1052 including a screw hole 1058, a first channel 1060, and a second channel 1062. The screw hole 1058 runs perpendicular to the first and second channels 1060 and 1062. The first and second channels 1060 and 1062 run parallel to each other and parallel to the lateral shafts 1020 of the plating system 1000. The first channel 1060 allows for the first cable 1030 to pass through the stabilizer plate 1050 and the second channel 1062 allows for the second cable 1032 to pass through the stabilizer plate 1050. The first cable 1030 may pass through a first opening 1034 in the base 1006, through the first channel 1060 in the stabilizer plates 1050, and finally through a first opening 1036 in the end plate 1004. Similarly, the second cable 1032 may pass through a second opening 1038 in the base 1006, through the second channel 1062 in the stabilizer plates 1050, and finally through a second opening 1040 in the end plate 1004.

During an anterior cervical discectomy and fusion or similar procedure and after the damaged disc has been removed and an interbody spacer has been inserted, a dynamic cervical plating system 1000 may be fastened to the patient's vertebrae. The plating system 1000 may first be aligned along the spinal column to cover the inserted spacer and then secured to a first vertebra by inserting fasteners into the screw holes 1018. Then a first stabilizer plate 1050 may be aligned and secured to a second vertebra below the first vertebra. The first stabilizer plate 1050 may be secured to the second vertebra using a fastener, such as screw 800 depicted in FIGS. 12a-12b. Next a second stabilizer plate 1050 may be aligned and secured to a third vertebra using a fastener, such as screw 800. It is also contemplated that the plating system 1000 may be secured to a patient's vertebrae in different orders than the one described above, such as securing the plating system 1000 to the first vertebra, then securing the second stabilizer plate 1050 to the third vertebra, and finally securing the first stabilizer plate 1050 to the second vertebra. Once the plating system 1000 is secured to the patient's vertebrae the patient's incision may be closed. The dynamic cervical plating system 900 will provide a degree of movement in the superior-inferior direction providing for a minimal change in length as the patient moves. In addition, as the vertebral body height decreases over time, the dynamic cervical plating system 1000 is able to adjust its height to accommodate the vertebral body changes.

Figure 22A:
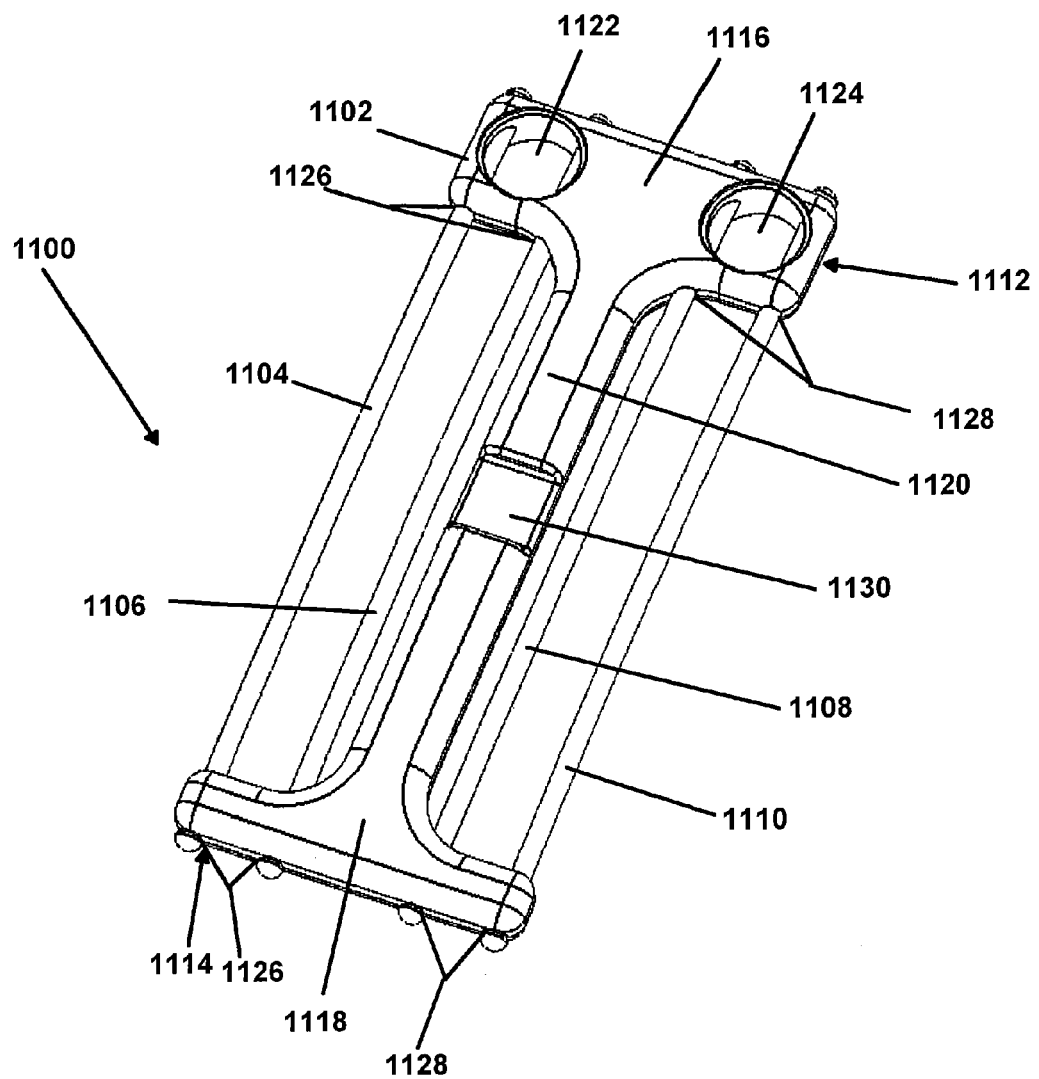
FIG. 22a is another embodiment of a dynamic cervical plating system from a top perspective view, in accordance with an aspect of the present invention.
Figure 22B:
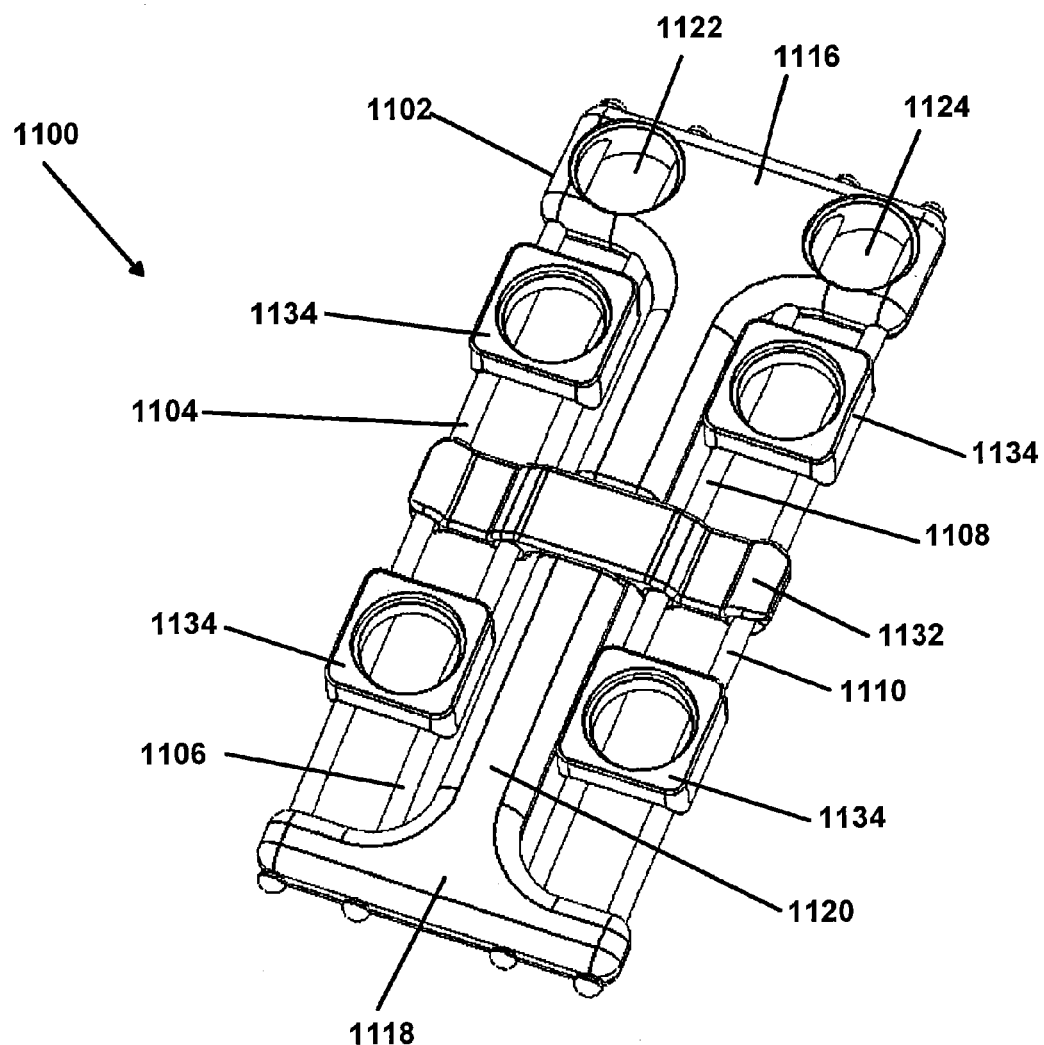
FIG. 22b is a top perspective view of the dynamic cervical plating system of FIG. 15a including a stabilizer bar and four fastener seats, in accordance with an aspect of the present invention.
Figure 22C:
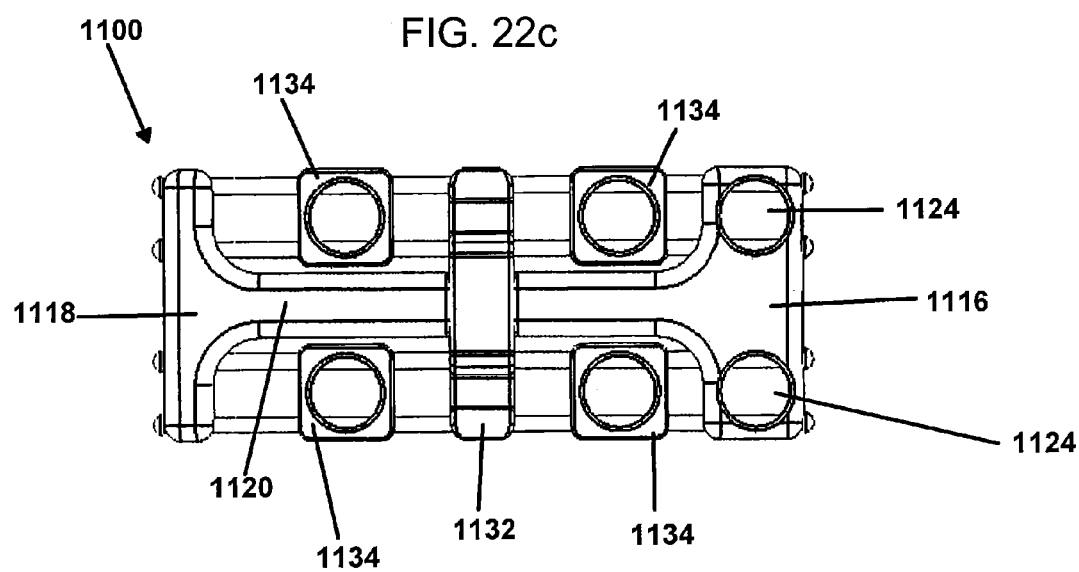
FIG. 22c is a top view of the dynamic cervical plating system of FIG. 15b, in accordance with an aspect of the present invention.
Figure 22D:
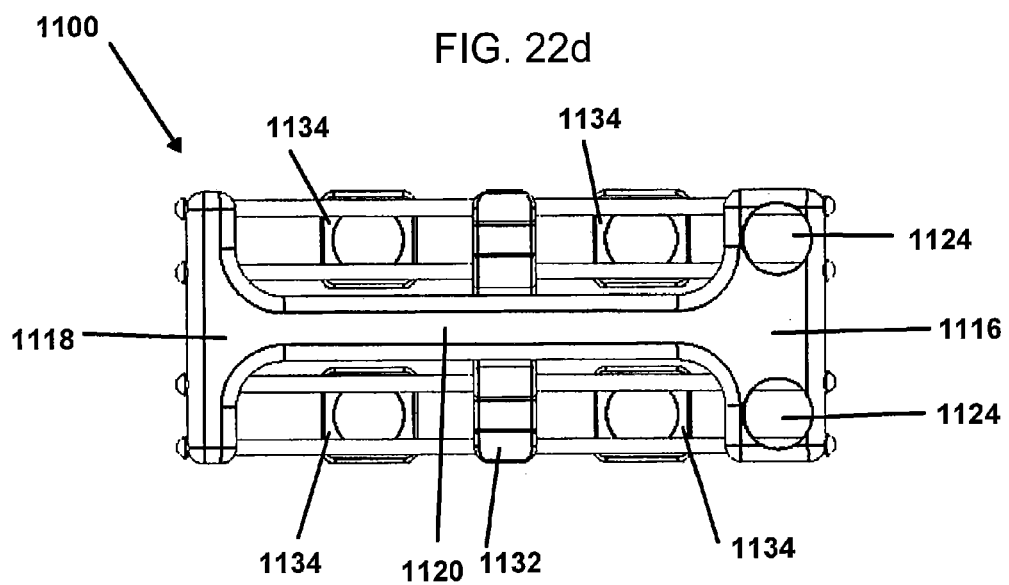
FIG. 22d is a bottom view of the dynamic cervical plating system of FIG. 15b, in accordance with an aspect of the present invention.
Figure 22E:
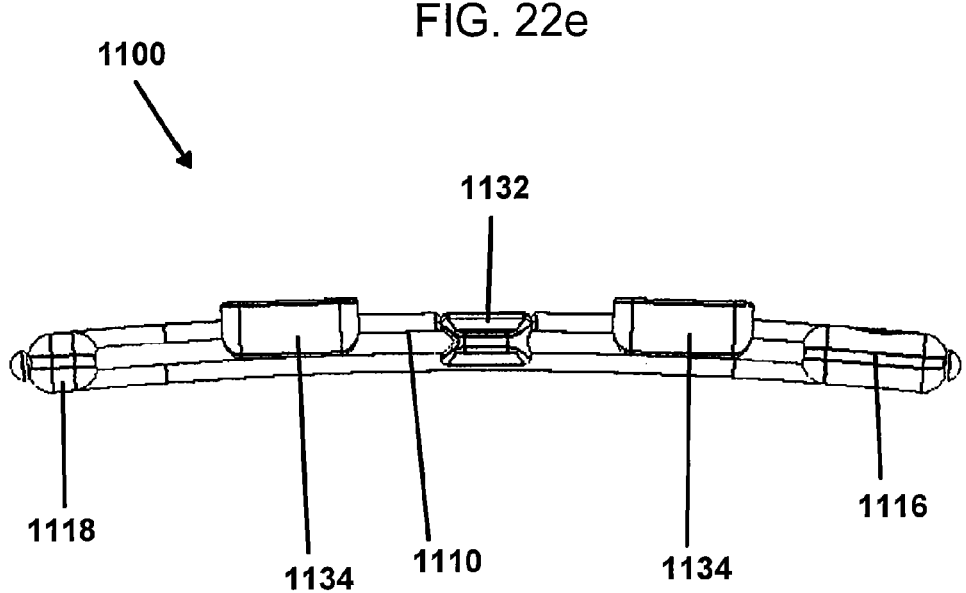
FIG. 22e is a side view of the dynamic cervical plating system of FIG. 15b, in accordance with an aspect of the present invention.

Another embodiment of dynamic vertical cervical plating system 1100 is depicted in FIGS. 22a-22e. As best seen in FIG. 22e, the dynamic cervical plating system 1100 is curved to mimic the lordotic curve of the spinal column. The dynamic vertical cervical plating system 1100 including a base plate 1102 and a double cable system. The base plate 1102 being generally "I" shaped and including a proximal end 1112 and a distal end 1114. The base plate 1102 also including a first end plate 1116 at the proximal end 1112, a second end plate 1118 at the distal end 1114, and an intervening shaft 1120 connecting the first end plate 1116 and the second end plate 1118. The first end plate 1116 including a first screw hole 1122 and a second screw hole 1124. The first end plate 1116 and the second end plate 1118 having a first set of parallel channels 1026 and a second set of parallel channels 1028. The first set of parallel channels 1026 and second set of parallel channels 1028 are also parallel with the intervening shaft 1120. The double cable system including a first cable 1104 and a second cable 1106 on a first side of the intervening shaft 1120 and a third cable 1108 and fourth cable 1110 on a second side of the intervening shaft 1120. The first and second cables 1104 and 1106, respectively, mate with the first set of parallel channels 1026. The third and fourth cables 1108 and 1110, respectively, mate with the second set of parallel channels 1028. The intervening shaft 1120 including a groove 1130 approximately centered along the intervening shaft 1120.

Figure 23A:
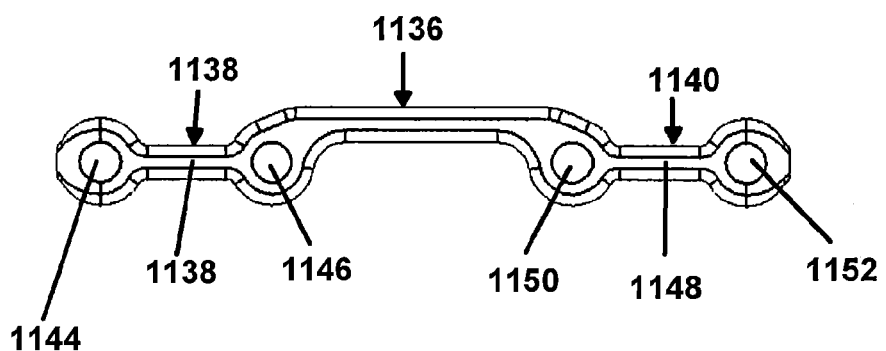
FIG. 23a is a side view of the stabilizer bar of FIG. 15b, in accordance with an aspect of the present invention.
Figure 23B:
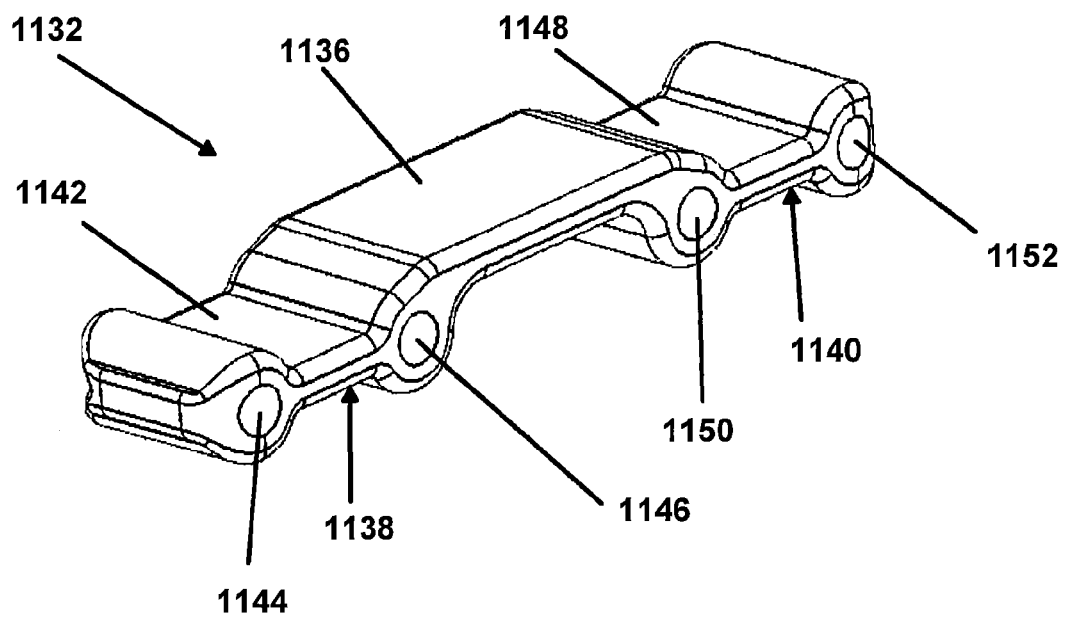
FIG. 23b is a top perspective view of the stabilizer bar of FIG. 16a, in accordance with an aspect of the present invention.
Figure 24C:
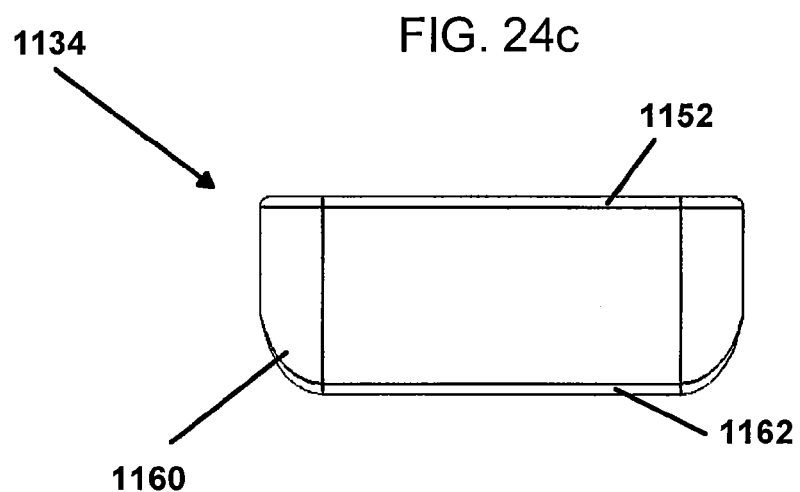
FIG. 24c is a front view of the fastener seat of FIG. 17a, in accordance with an aspect of the present invention.
Figure 24D:
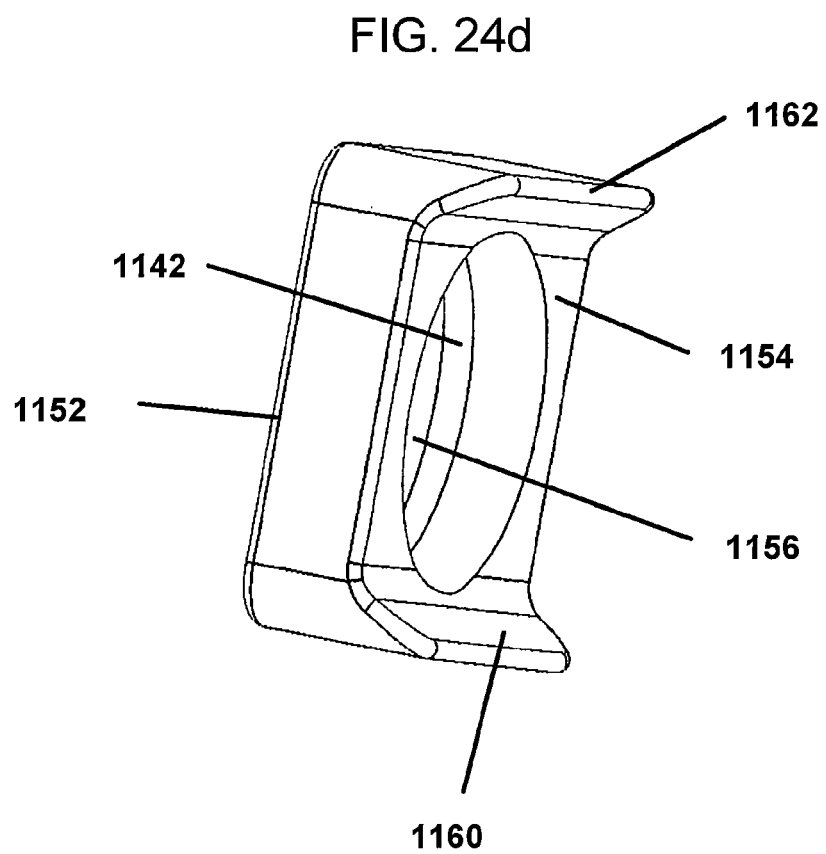
FIG. 24d is a bottom perspective view of the fastener seat of FIG. 17a, in accordance with an aspect of the present invention.

As best illustrated in FIGS. 22b-22e, the dynamic vertical cervical plating system 1100 may have a stabilizer plate 1132 and at least one screw seat 1134. The stabilizer plate 1132, as shown in FIGS. 23a-23b, including a center base 1136 with a first tab 1138 and a second tab 1140. The center base 1136 shaped to match the shape of the groove 1130. The first tab 1138 including a center portion 1142 with a first channel 1144 on one side of the center portion 1142 and a second channel 1146 on a second side of the center portion 1142. The second tab 1140 including a center portion 1148 with a first channel 1150 on one side of the center portion 1148 and a second channel 1152 on a second side of the center portion 1148. When the stabilizer plate 1132 is inserted onto the intervening shaft 1120, the first channel 1144 aligns with the first cable 1104, the second channel 1146 aligns with the second cable 1106, the first channel 1150 aligns with the third cable 1108, and the second channel 1152 aligns with the fourth cable 1110.

In the depicted embodiments of FIGS. 22b-22e, there are four screw seats 1134 shown. The screw seat 1134, as depicted in FIGS. 24a-24d, has a generally square shape with a first side 1152, a second side 1154, and a screw hole 1156. Where the screw hole 1156 meets the first side 1152 there is a groove 1158 which provides a stop for a screw, such as screw 800 described above, when the screw 800 is inserted into the patient's vertebra. The second side 1154 includes a first lip 1160 and a second lip 1162 for mating with the first and second cables 1104 and 1106, respectively, or the third and fourth cables 1108 and 1110, respectively. The screw seat 1134 provides support for the screw 800 when the dynamic cervical plating system 1100 is secured to the patient's vertebrae.

During an anterior cervical discectomy and fusion or similar procedure and after the damaged disc has been removed and an interbody spacer has been inserted, a dynamic cervical plating system 1100 including the stabilizer plate 1132 may be fastened to the patient's vertebrae. The plating system 1100 may first be aligned along the spinal column to cover the inserted spacer and then secured to a first vertebra by inserting fasteners into the screw holes 1122 and 1124. Then a first pair of screw seats 1134 may be aligned over a second vertebra below the first vertebra and over the first and second cables 1104 and 1106, respectively, and the third and fourth cables 1108 and 1110, respectively. The first pair of screw seats 1134 may be secured to the second vertebra using a fastener for each screw seat 1134, such as screw 800 depicted in FIGS. 12a-12b. Next a second pair of screw seats 1134 may be aligned and secured to a third vertebra using a fastener, such as screw 800, over the first and second cables 1104 and 1106, respectively, and the third and fourth cables 1108 and 1110, respectively. It is also contemplated that the plating system 1100 and screw seats 1134 may be secured to a patient's vertebrae in different orders than the one described above, such as being secured first to the first vertebra, then to the third vertebra, and finally to the second vertebra between the first and third vertebrae. Once the plating system 1100 is secured to the patient's vertebrae the patient's incision may be closed. The dynamic cervical plating system 1100 will provide a degree of movement in the superior-inferior direction providing for a minimal change in length as the patient moves. In addition, as the vertebral body height decreases over time, the dynamic cervical plating system 1100 is able to adjust its height to accommodate the vertebral body changes.

The description of the various embodiments is merely exemplary in nature and, thus, variations that do not depart from the gist of the various embodiments are intended to be within the scope of the present disclosure and appended claims. Such variations are not to be regarded as a departure from the spirit and scope of the present disclosure and appended claims.

What is claimed is:

1. A dynamic spinal plating system comprising:
   a plate with a superior end, an inferior end, and first and second lateral sides that connect the superior end and inferior end and form an opening therebetween that is elongated along a first direction extending between the superior and inferiors ends, wherein the superior end includes at least one through hole, and wherein the first and second lateral sides each include a slot that extends therethrough and along the first direction; and
   at least one bone attachment mechanism extending transverse to and within the opening between the first and second lateral sides of the plate,
   wherein the at least one bone attachment mechanism comprises:
      a pair of transverse members;
      a first locking mechanism coupled to a first end of the pair of transverse members and positioned on a side of the first lateral side opposite the opening; and
      a second locking mechanism coupled to a second end of the pair of transverse members and positioned on a side of the second lateral side opposite the opening;
   wherein the pair of transverse members is spaced along the first direction and the pair of transverse members pass through the slots of the first and second lateral sides to allow the pair of transverse members to slide along the first direction within the opening.

2. The dynamic spinal plating system of claim 1, wherein the pair of transverse members pass through the slots of the first and second lateral sides and each include a first end and a second end, the first end of the transverse members being positioned adjacent to an outer side surface of the first lateral side that substantially opposes the opening, and the second end of the transverse members being positioned adjacent to an outer side surface of the second lateral side that substantially opposes the opening.

3. The dynamic spinal plating system of claim 1, wherein the pair of transverse members are secured to the first lateral side with the first locking mechanism and to the second lateral side with the second locking mechanism.

4. The dynamic spinal plating system of claim 3, wherein the locking mechanisms may comprise a clamp, bolt, crimp, nut, tap, or rivet.

5. The dynamic spinal plating system of claim 1, wherein the pair of transverse members are comprised of a rigid material, selected from the group consisting of steel, titanium, chrome, and cobalt.

6. The dynamic spinal plating system of claim 1, wherein the pair of transverse members are comprised of a flexible material, selected from the group consisting of cable, wire, composite, and polymer.

7. The dynamic spinal plating system of claim 1, wherein the pair of transverse members are comprised of a continuous flexible material.

8. The dynamic spinal plating system of claim 1, further comprising:
   at least one center hole plate with a superior side and an inferior side, wherein a center hole passes from the superior side to the inferior side and the inferior side includes two channels that mate with the pair of transverse members.

9. The dynamic spinal plating system of claim 1, wherein the at least one bone attachment mechanism is configured to be fixed to a vertebral body with a bone fastener.

10. The dynamic spinal plating system of claim 9, wherein the bone fastener is a screw comprising a head, a threaded end, and a groove, wherein the groove is sized to receive the pair of transverse members.

11. The dynamic spinal plating system of claim 9, wherein the bone fastener is a screw comprising a head and a shaft, wherein the head comprises a convex top surface with an opening and a planar bottom surface, and wherein the shaft comprises a top portion adjacent the head and a threaded portion offset from the head and below the top portion of the shaft.

12. The dynamic spinal plating system of claim 9, wherein the bone fastener is a nail including a hook portion to receive at least one of the pair of transverse members and a shank portion with at least one barb to secure the nail into the vertebral body.

13. The dynamic spinal plating system of claim 1, wherein the plate is curved along the sagittal plane to correspond to the shape of a patient's spine.

14. The dynamic spinal plating system of claim 1, wherein the slot of each of the first and second lateral sides of the plate extends therethrough along a second direction that extends substantially perpendicular to the first direction.

15. The dynamic spinal plating system of claim 1, wherein the pair of transverse members of the at least one bone attachment mechanism form a second opening therebetween that is positioned within the opening of the plate.

16. The dynamic spinal plating system of claim 15, wherein the second opening extends between the transverse members and the first and second lateral sides of the plate.

17. The dynamic spinal plating system of claim 1, wherein the pair of transverse members of the at least one bone attachment mechanism are spaced along the first direction a fixed distance at least at the first and second lateral sides.

18. The dynamic spinal plating system of claim 1, wherein at least each of the first and second lateral sides of the plate define a bone engagement surface and a top surface opposing the bone engagement surface, and wherein the pair of transverse members of the at least one bone attachment mechanism are positioned intermediate of the bone engagement surfaces and the top surfaces of the first and second lateral sides of the plate.

19. A surgical method for fusing a spine, comprising:
   obtaining a dynamic spinal plating system, comprising:
      a plate with a superior end, an inferior end, and first and second lateral sides that connect the superior end and inferior end and form an opening therebetween that is elongated along a first direction extending between superior and inferiors ends, wherein the superior end includes at least one screw hole, and wherein the first and second lateral sides each include a slot that extends therethrough and along the first direction; and
      at least one bone attachment mechanism extending transverse to and within the opening between the first and second lateral sides of the plate,
      wherein the at least one bone attachment mechanism includes a pair of transverse members spaced along the first direction that pass through the slots of the first and second lateral sides to allow the pair of transverse members to slide along the first direction within the opening, a first locking mechanism coupled to a first end of the pair of transverse members and positioned on a side of the first lateral side opposite the opening, and a second locking mechanism coupled to a second end of the pair of transverse members and positioned on a side of the second lateral side opposite the opening; and
   fixing the dynamic spinal plating system to an anterior aspect of a spine using a bone fastener.

* * * * *